US012193687B2

(12) United States Patent
Sikora et al.

(10) Patent No.: US 12,193,687 B2
(45) Date of Patent: Jan. 14, 2025

(54) GLENOID REPAIR SYSTEM AND METHODS OF USE THEREOF

(71) Applicant: Arthrosurface Incorporated, Franklin, MA (US)

(72) Inventors: George Sikora, Bridgewater, MA (US); Steven W. Ek, Bolton, MA (US); Nikhil T. Jawrani, Bellingham, MA (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 114 days.

(21) Appl. No.: 17/202,570

(22) Filed: Mar. 16, 2021

(65) Prior Publication Data

US 2021/0378686 A1 Dec. 9, 2021

Related U.S. Application Data

(63) Continuation of application No. 15/079,342, filed on Mar. 24, 2016, now Pat. No. 10,945,743, which is a
(Continued)

(51) Int. Cl.
*A61B 17/16* (2006.01)
*A61B 17/17* (2006.01)
*A61F 2/40* (2006.01)
*A61F 2/46* (2006.01)
*A61F 2/30* (2006.01)

(52) U.S. Cl.
CPC ...... *A61B 17/1684* (2013.01); *A61B 17/1778* (2016.11); *A61F 2/4081* (2013.01); *A61F 2/4612* (2013.01); *A61B 17/1604* (2013.01); *A61F 2002/30233* (2013.01); *A61F 2002/30818* (2013.01); *A61F 2002/30879* (2013.01);
(Continued)

(58) Field of Classification Search
CPC .......... A61F 2002/30233; A61F 2/4081; A61F 2/4612; A61B 17/17; A61B 17/1778; A61B 17/1764; A61B 17/1714; A61B 17/1739; A61B 17/1684
See application file for complete search history.

(56) References Cited

U.S. PATENT DOCUMENTS 3,664,345 A 5/1972 Dabbs et al.
3,910,281 A 10/1975 Kletschka et al.
(Continued)

FOREIGN PATENT DOCUMENTS

FR 2567019 A1 1/1986
FR 2695313 A1 3/1994

OTHER PUBLICATIONS

Vilex—Restoring Mobility, Cannulated Implants for Forefoot Joints, QSD 8.12-11 Rev D, 2010, 4 pages.
(Continued)

*Primary Examiner* — Sameh R Boles
(74) *Attorney, Agent, or Firm* — Grossman, Tucker, Perreault & Pfleger, PLLC

(57) ABSTRACT

The present disclosure provides systems and methods for repairing a defect on a portion of an articular surface of a human body, particularly of the glenoid. More particularly, the present disclosure provides systems and methods for repairing both a glenoid cavity and a glenoid rim of the glenoid using a single implant.

26 Claims, 45 Drawing Sheets

Related U.S. Application Data continuation-in-part of application No. 12/762,948, filed on Apr. 19, 2010, now Pat. No. 9,662,126.

(60) Provisional application No. 62/137,581, filed on Mar. 24, 2015, provisional application No. 61/170,290, filed on Apr. 17, 2009.

(52) U.S. Cl.
CPC ............... *A61F 2002/30881* (2013.01); *A61F 2002/30884* (2013.01)

(56) References Cited

U.S. PATENT DOCUMENTS

| | | |
|---|---|---|
| 3,976,079 A | 8/1976 | Samuels et al. |
| 4,662,891 A * | 5/1987 | Noiles .................. A61F 2/4609 623/22.25 |
| 4,741,330 A | 5/1988 | Hayhurst |
| 4,964,865 A | 10/1990 | Burkhead et al. |
| 5,078,731 A | 1/1992 | Hayhurst |
| 5,306,290 A | 4/1994 | Martins et al. |
| 5,306,301 A | 4/1994 | Graf et al. |
| 5,489,310 A | 2/1996 | Mikhail |
| 5,529,075 A | 6/1996 | Clark |
| 5,769,894 A | 6/1998 | Ferragamo |
| 5,782,866 A | 7/1998 | Wenstrom, Jr. |
| 5,921,986 A | 7/1999 | Bonutti |
| 5,928,285 A | 7/1999 | Bigliani et al. |
| 6,007,566 A | 12/1999 | Wenstrom, Jr. |
| 6,099,568 A | 8/2000 | Simonian et al. |
| 6,110,207 A | 8/2000 | Eichhorn et al. |
| 6,228,119 B1 | 5/2001 | Ondrla et al. |
| 6,478,178 B2 | 11/2002 | Montgomery |
| 6,517,578 B2 | 2/2003 | Hein |
| 6,537,274 B1 | 3/2003 | Katz |
| 6,638,279 B2 | 10/2003 | Bonutti |
| 7,169,184 B2 | 1/2007 | Dalla Pria |
| 7,235,091 B2 | 6/2007 | Thornes |
| 7,455,683 B2 | 11/2008 | Geissler |
| 7,875,058 B2 | 1/2011 | Holmes, Jr. |
| 7,901,431 B2 | 3/2011 | Shurnas |
| 7,927,335 B2 | 4/2011 | Deffenbaugh et al. |
| 8,147,514 B2 | 4/2012 | Bonutti |
| 8,277,459 B2 | 10/2012 | Sand et al. |
| 8,337,563 B2 | 12/2012 | Roche et al. |
| 8,690,952 B2 | 4/2014 | Dallmann |
| 8,870,962 B2 | 10/2014 | Roche et al. |
| 8,888,855 B2 | 11/2014 | Roche et al. |
| 8,920,508 B2 | 12/2014 | Iannotti et al. |
| 9,233,003 B2 | 1/2016 | Roche et al. |
| 9,278,413 B2 | 3/2016 | Sperling |
| 9,289,221 B2 | 3/2016 | Gelaude et al. |
| 9,351,743 B2 | 5/2016 | Kehres et al. |
| 9,421,106 B2 | 8/2016 | Splieth et al. |
| 9,498,344 B2 | 11/2016 | Hodorek et al. |
| 9,512,445 B2 | 12/2016 | Iannotti |
| 9,603,712 B2 | 3/2017 | Bachmaier |
| 9,622,869 B2 | 4/2017 | Nerot et al. |
| 9,629,725 B2 | 4/2017 | Gargac et al. |
| 9,724,168 B2 | 8/2017 | Yeung |
| 9,763,798 B2 | 9/2017 | Chavarria et al. |
| 9,839,438 B2 | 12/2017 | Eash |
| 9,956,083 B2 | 5/2018 | Humphrey |
| 10,034,759 B2 | 7/2018 | Deransart et al. |
| 10,143,558 B2 | 12/2018 | Frankle |
| 10,172,714 B2 | 1/2019 | Hatzidakis et al. |
| 10,271,858 B2 | 4/2019 | Guilloux et al. |
| 10,398,514 B2 | 9/2019 | Ryan et al. |
| 10,420,649 B2 | 9/2019 | Overes et al. |
| 10,426,495 B2 | 10/2019 | Bonnin, Jr. et al. |
| 10,441,298 B2 | 10/2019 | Eash |
| 10,478,200 B2 | 11/2019 | Sikora et al. |
| 10,485,670 B2 | 11/2019 | Maale et al. |
| 10,537,390 B2 | 1/2020 | Varadarajan et al. |
| 10,548,737 B2 | 2/2020 | Hodorek et al. |
| 10,583,012 B1 | 3/2020 | Longobardi |
| 10,595,886 B2 | 3/2020 | Termanini |
| 10,624,748 B2 | 4/2020 | Ek et al. |
| 10,631,992 B2 | 4/2020 | Hopkins |
| 10,709,565 B2 | 7/2020 | Humphrey et al. |
| 10,736,751 B2 | 8/2020 | Hodorek |
| 10,945,743 B2 | 3/2021 | Sikora et al. |
| 10,959,740 B2 | 3/2021 | Sikora et al. |
| 10,966,814 B2 | 4/2021 | Hansen et al. |
| 10,973,645 B2 | 4/2021 | Deransart et al. |
| 10,987,176 B2 | 4/2021 | Poltaretskyi et al. |
| 11,020,128 B2 | 6/2021 | Guilloux et al. |
| 11,033,399 B2 | 6/2021 | Hatzidakis et al. |
| 11,065,125 B2 | 7/2021 | Ball et al. |
| 11,071,596 B2 | 7/2021 | Ryan et al. |
| 11,083,525 B2 | 8/2021 | Varadarajan et al. |
| 11,090,123 B2 | 8/2021 | Yeung |
| 11,103,357 B2 | 8/2021 | Gargac et al. |
| 11,129,724 B2 | 9/2021 | Knox et al. |
| 11,166,733 B2 | 11/2021 | Neichel et al. |
| 11,173,037 B2 | 11/2021 | Deransart et al. |
| 11,197,764 B2 | 12/2021 | Mutchler et al. |
| 11,229,522 B2 | 1/2022 | Nerot et al. |
| 11,234,721 B2 | 2/2022 | Gargac |
| 2002/0082702 A1 | 6/2002 | Resch et al. |
| 2003/0125809 A1 | 7/2003 | Iannotti et al. |
| 2004/0260298 A1 | 12/2004 | Kaiser et al. |
| 2005/0085915 A1 | 4/2005 | Steinberg |
| 2007/0016208 A1 | 1/2007 | Thornes |
| 2007/0179531 A1 | 8/2007 | Thornes |
| 2008/0046009 A1 | 2/2008 | Albertorio et al. |
| 2008/0077182 A1 | 3/2008 | Geissler et al. |
| 2009/0036893 A1 | 2/2009 | Kartalian et al. |
| 2010/0152752 A1 | 6/2010 | Denove et al. |
| 2010/0211071 A1 | 8/2010 | Lettmann et al. |
| 2010/0268273 A1 | 10/2010 | Albertorio et al. |
| 2011/0118780 A1 | 5/2011 | Holmes, Jr. |
| 2011/0137341 A1 | 6/2011 | Thornes et al. |
| 2011/0178557 A1 | 7/2011 | Rush et al. |
| 2011/0224729 A1 | 9/2011 | Baker et al. |
| 2011/0301648 A1 | 12/2011 | Lofthouse et al. |
| 2012/0016428 A1 | 1/2012 | White et al. |
| 2012/0071935 A1 | 3/2012 | Keith et al. |
| 2012/0101502 A1 | 4/2012 | Kartalian et al. |
| 2012/0150203 A1 | 6/2012 | Brady et al. |
| 2012/0330322 A1 | 12/2012 | Sand et al. |
| 2016/0038161 A1 * | 2/2016 | Gibson .................. A61F 2/4609 606/86 R |
| 2016/0287266 A1 | 10/2016 | Sikora et al. |
| 2017/0128220 A1 | 5/2017 | Iannotti |
| 2021/0022877 A1 | 1/2021 | Ek |
| 2021/0030549 A1 | 2/2021 | Ek et al. |
| 2021/0030550 A1 | 2/2021 | Ek et al. |
| 2021/0038395 A1 | 2/2021 | Ek et al. |
| 2021/0038398 A1 | 2/2021 | Sikora et al. |

OTHER PUBLICATIONS

Tornier Implants Chirurgicaux—Aequalis Reversed Shoulder Prosethesis, K132285, Dec. 5, 2013, 8 pages.
Tornier, Aequalis Reversed II Shoulder, Nov. 2014, 3 pages.
Johnson & Johnson Medical Devices Companies—Global PA Shoulder System, https://www.depuysynthes.com/hcp/shoulder/products/qs/DELTAXTEND-Reverse-Shoulder-System, Nov. 2014, 7 pages.
Zimmer Biomet—Joint Replacement Orthopaedic Devices_Hip_Knee_Shoulder, http://www.biomet.com/orthopedics/getfile.cfm?id=2905&rt=inline, Nov. 2014, 3 pages.

* cited by examiner

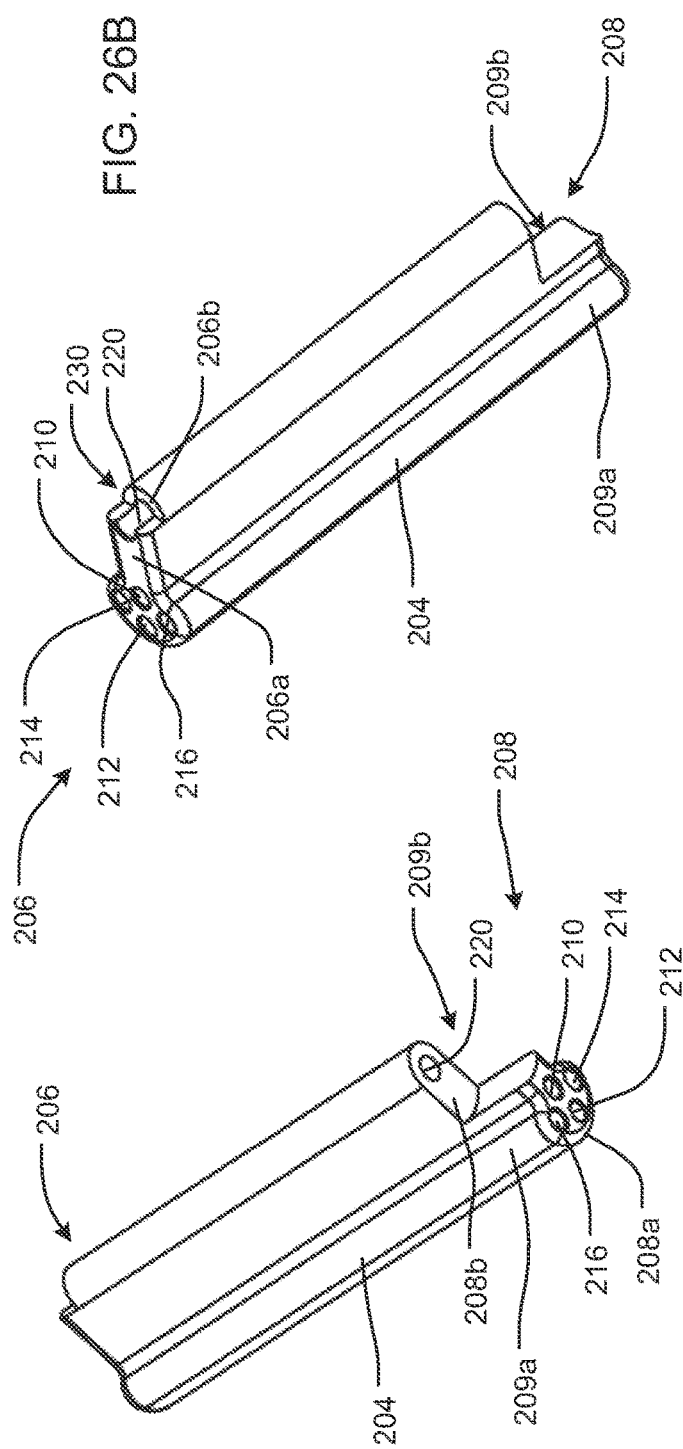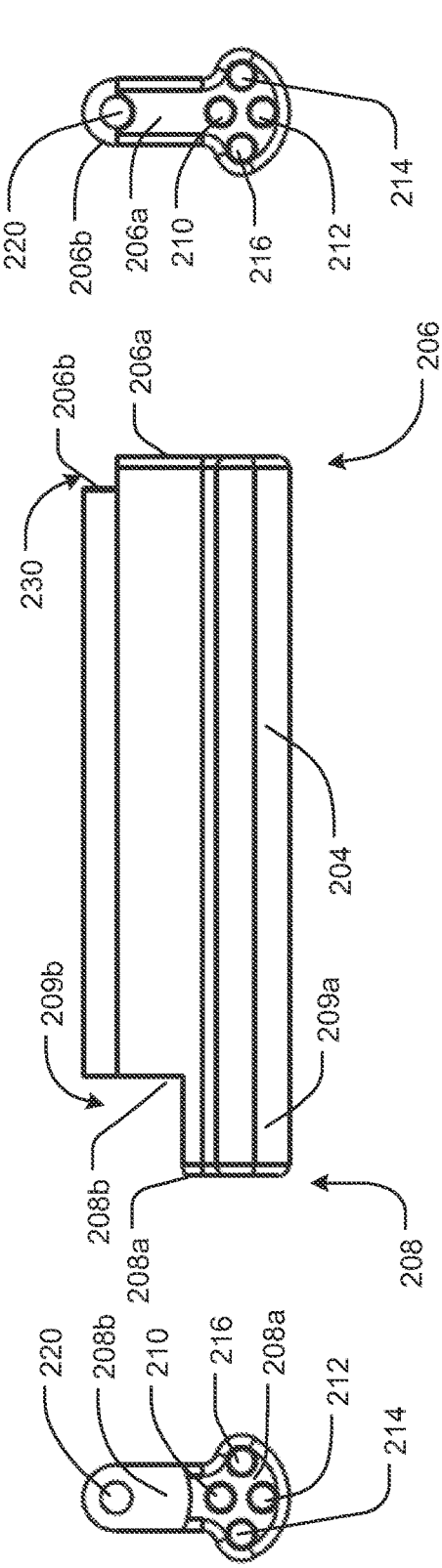

FIG. 30A
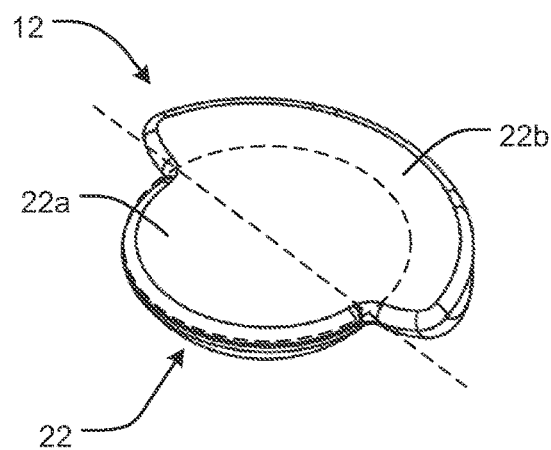
FIG. 30B
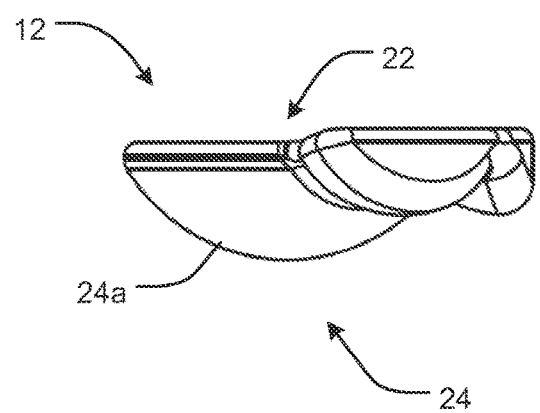
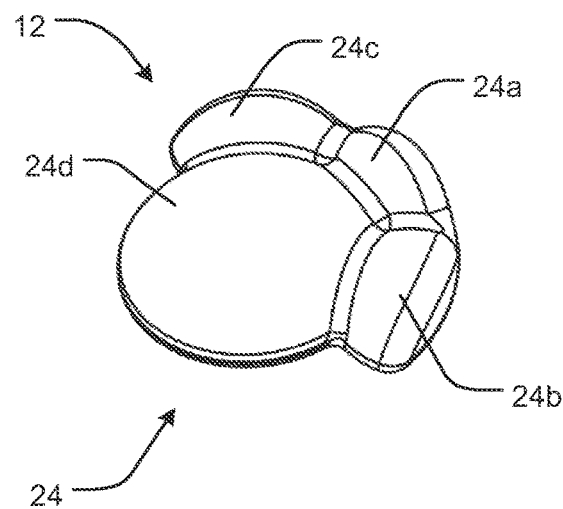
FIG. 30C
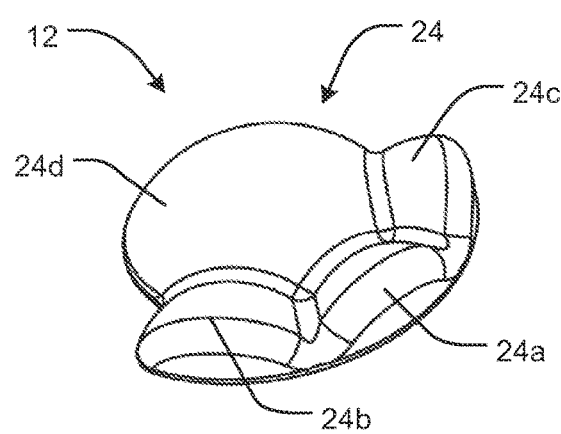
FIG. 30D

GLENOID REPAIR SYSTEM AND METHODS OF USE THEREOF

CROSS-REFERENCE TO RELATED APPLICATIONS

This application is a continuation of U.S. patent application Ser. No. 15/079,342, (now U.S. Pat. No. 10,945,743), filed Mar. 24, 2016, which claims the benefit of U.S. Provisional Patent Application Ser. No. 62/137,581, filed Mar. 24, 2015, the contents of which are hereby incorporated by reference herein. This application is also a continuation-in-part of U.S. Ser. No. 12/762,948, (now U.S. Pat. No. 9,662,126), filed on Apr. 19, 2010, which claims the benefit of U.S. Provisional No. 61/170,290, filed on Apr. 17, 2009, the teachings both of which are incorporated herein by reference.

FIELD

This disclosure relates to systems and methods for the repair of defects that occur in articular cartilage on the surface of bones, particularly the shoulder.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF DRAWINGS

The above-mentioned and other features of this disclosure, and the manner of attaining them, may become more apparent and better understood by reference to the following description of embodiments described herein taken in conjunction with the accompanying drawings, wherein:

FIG. 26A illustrates a first perspective view of the guide body of the excision apparatus of FIG. 25;

FIG. 26B illustrates a second perspective view of the guide body of the excision apparatus of FIG. 25;

FIG. 26C illustrates a side view of the guide body of the excision apparatus of FIG. 25;

FIG. 26D illustrates a proximal end view of the guide body of the excision apparatus of FIG. 25;

FIG. 26E illustrates a distal end view of the guide body of the excision apparatus of FIG. 25;

FIG. 30A illustrates a top perspective view of the implant of FIGS. 25 and 29G;

FIG. 30B illustrates a side view of the implant of FIGS. 25 and 29G;

FIG. 30C illustrates a first bottom perspective view of the implant of FIGS. 25 and 29G;

FIG. 30D illustrates a first bottom perspective view of the implant of FIGS. 25 and 29G;

DETAILED DESCRIPTION

The present disclosure may feature a systems and methods for resurfacing at least a portion of an articular surface having one or more defects by replacing a portion of the articular surface with an implant. The implant may comprise a load bearing surface having a contour and/or shape substantially corresponding to the patient's original articular surface about the defect site which may be configured to engage and cooperate with an adjacent articular surface. The present disclosure will describe a systems and methods for replacing a portion of the articular surface of the glenoid; however, it should be understood that the systems and methods according to the present disclosure may also be used to resurface articular surfaces other than the glenoid.

As an initial matter, many of the devices described herein comprise cannulated components configured to be arranged over other components. The degree to which the cannulated passageway (i.e., internal diameter of the passageway/cavity) of a first component corresponds to the external diameter of the component over which it is being placed may be close enough to generally eliminate excessive movement. Excessive movement may be defined as an amount of movement that may result in surgically relevant misalignment of the implant relative to the articular surface.

Figure 1:
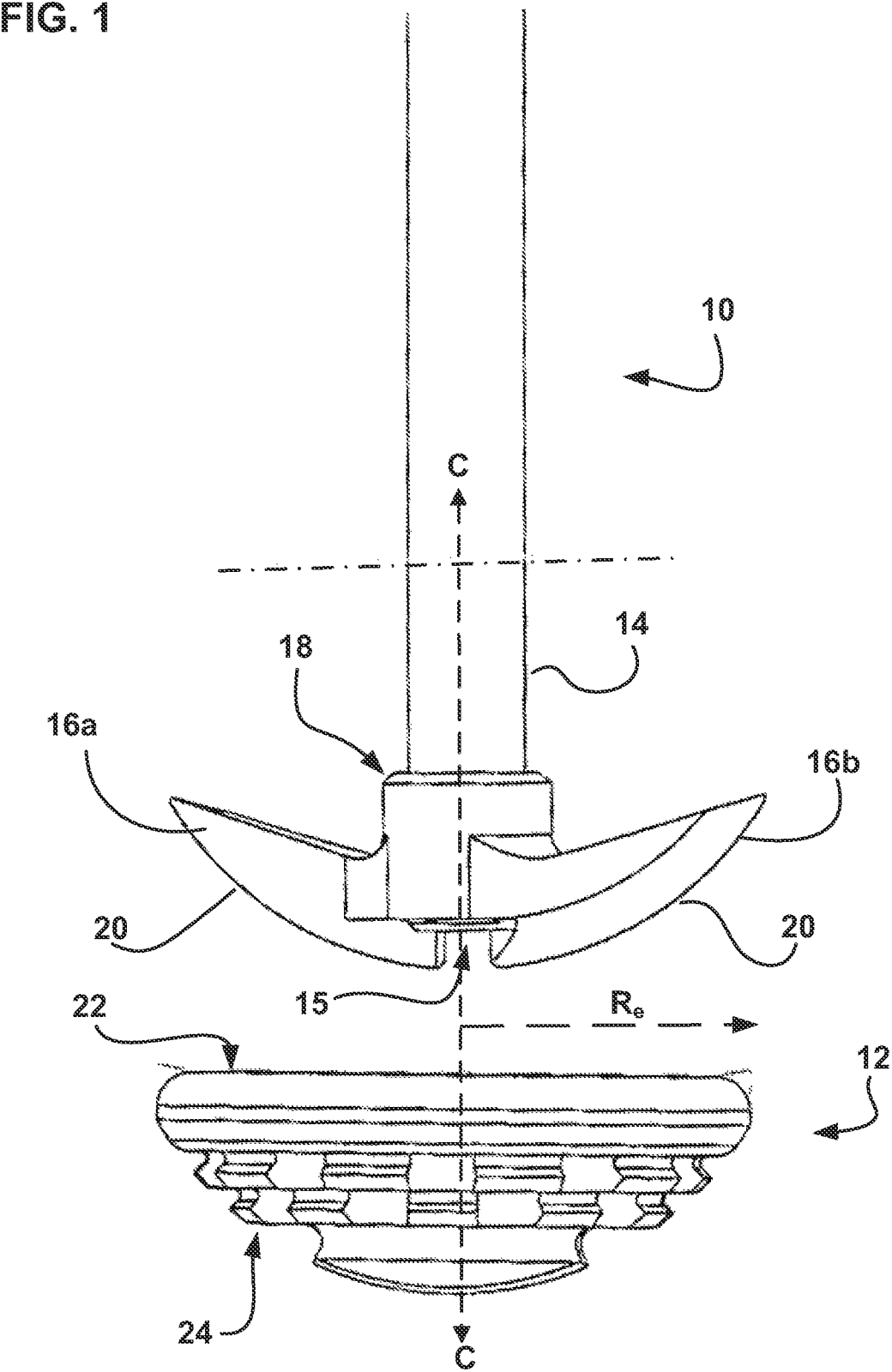
FIG. 1 illustrates a side view of an example of an excision device and an implant.

Referring now to FIG. 1, one embodiment of an excision device 10 and an implant 12 are generally illustrated. As will be explained in greater detail herein, the excision device 10 may be configured to form an excision site within the articular surface (e.g., the glenoid) configured to receive at least a portion of the implant 12. The implant 12 may be configured to replace the articular surface in an area proximate one or more defects. The system and method consistent with the present disclosure may repair a defect on the articular surface of a glenoid without having to replace the entire glenoid.

Accordingly to at least one embodiment, the implant 12 may be configured to replace only a portion of the articular surface proximate the defect site rather than the entire articular surface. As such, the implant 12 may minimize the amount of the articular surface which is operated on thus allowing more of the patient's original articular surface to be unaffected and providing a more physiologically normal joint. The system and method consistent with one embodiment of the present disclosure may allow for "key-hole" surgery in which a minimum number and size of incisions are made. As may be appreciated, "key-hole" surgery may reduce the amount of pain and/or discomfort experienced by the patient and may reduce healing times.

The excision device 10 may include a cannulated shaft 14 defining a passageway 15 configured to be received over at least a portion of a guide pin or the like (not shown). The excision device 10 may also include at least one cutter 16a, 16b extending radially outwardly (transversely) and away from a distal end 18 of the shaft 14. Each cutter 16a, 16b may have a cutting surface 20 configured to create a hemi-spherical implant site, i.e., an excision site to receive the implant. For example, the cutting surface 20 may have a generally arcuate shape which sweeps towards the proximal end of the shaft 14 as the radius $R_e$ from the shaft 14 increases on the cutter 16a, 16b. It may be appreciated that the hemi-spherical excision site may exhibit some degree of deviation and the hemi-spherical excision site may be, in some examples, teardrop shaped or pyriform.

The contour of the cutting surfaces 20 may define the contours of the excision site as the cutters 16a, 16b are rotated about the central axis of the excision site. While the cutting surfaces 20 are illustrated having a generally constant arc or curvature, the cutting surfaces 20 may include one or more protrusions and/or recesses configured to create corresponding radial groove and/or lips/protrusions within the excision site. These radial grooves and/or lips/protrusions on the cutting surfaces 20 may facilitate alignment of the implant 12 and/or may increase the mechanical coupling of the implant 12 within the excision site.

Figure 2:
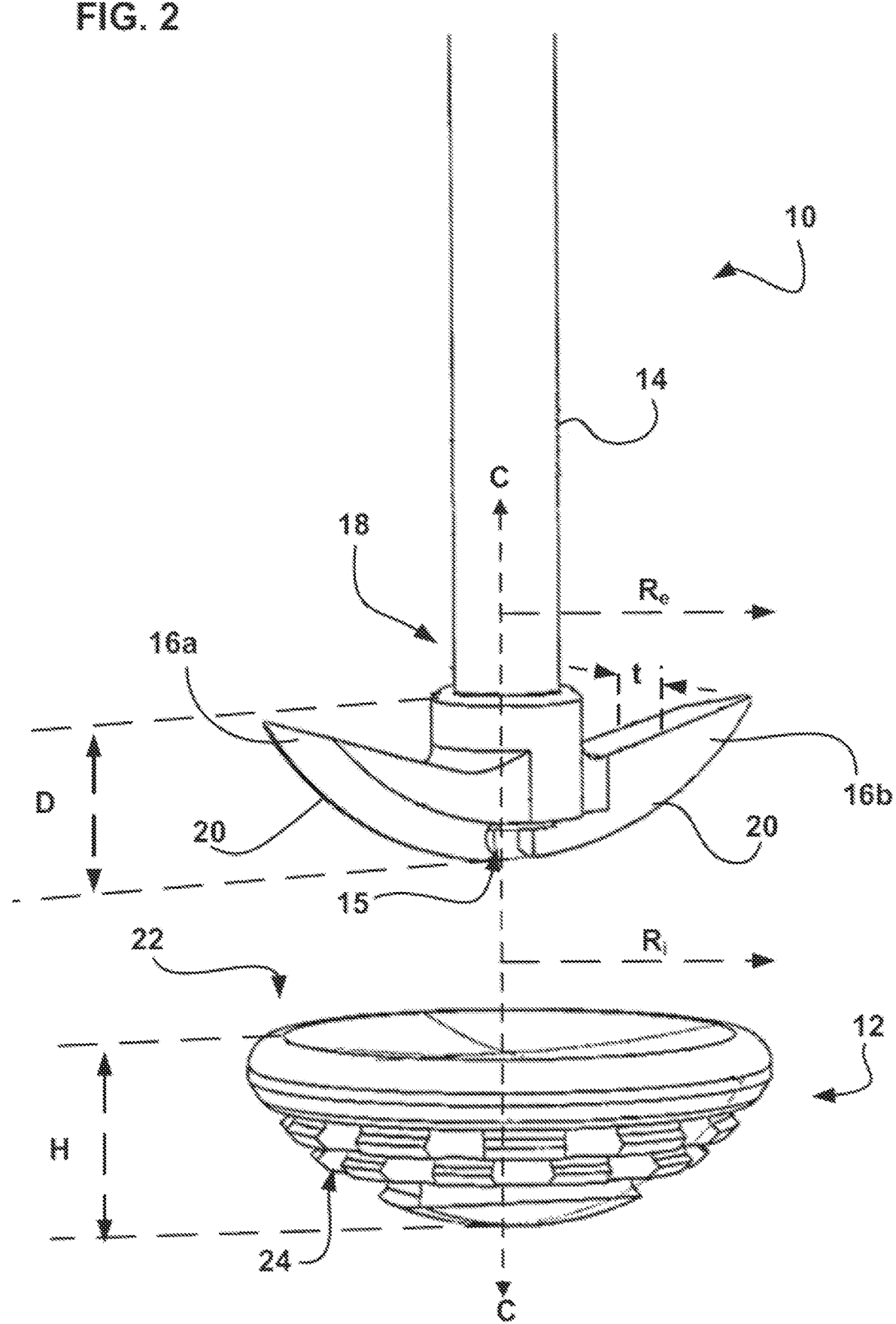
FIG. 2 illustrates a perspective view of an example of an excision device and an implant.

Turning now to FIG. 2, the overall radius $R_e$ of the cutters 16a, 16b may define the radius of the implant site created by the excision device 10 within the articular surface and may also substantially correspond to the radius $R_i$ of the implant 12. In addition, the depth D of the cutters 16a, 16b may also define the height of the excision site created by the excision device 10 and may also substantially correspond to the height H of the implant 12. For example, the overall radius $R_e$ of the cutters 16a, 16b may be between 7.0 mm to 20.0 mm, for example, 7.0 mm to 15.0 mm and/or 10.0 mm to 12.5 mm (including all values and ranges therein) and the depth D may be between 4.0 mm to 10.0 mm, for example, 5 mm (including all values and ranges therein).

According to at least one embodiment, the excision device 10 may include a first and a second cutter 16a, 16b which may be disposed approximately 180 degrees relative to each other. For example, the cutters 16a, 16b may extend generally radially outwardly from the shaft about a first and a second generally opposite side of the distal end 18 of the shaft 14. The cutters 16a, 16b may also have a generally slim profile configured to be disposed between two adjacent articular surfaces as explained further herein. For example, the cutters 16a, 16b may have a cross-sectional thickness (t) of 0.5 mm to 3.0 mm, for example, 2.0 mm (including all values and ranges therein). In one embodiment the at least one cutter may provide a generally hemispherical excision site regardless of the angle which the guide pin is disposed relative to the articular surface 54.

Figure 3:
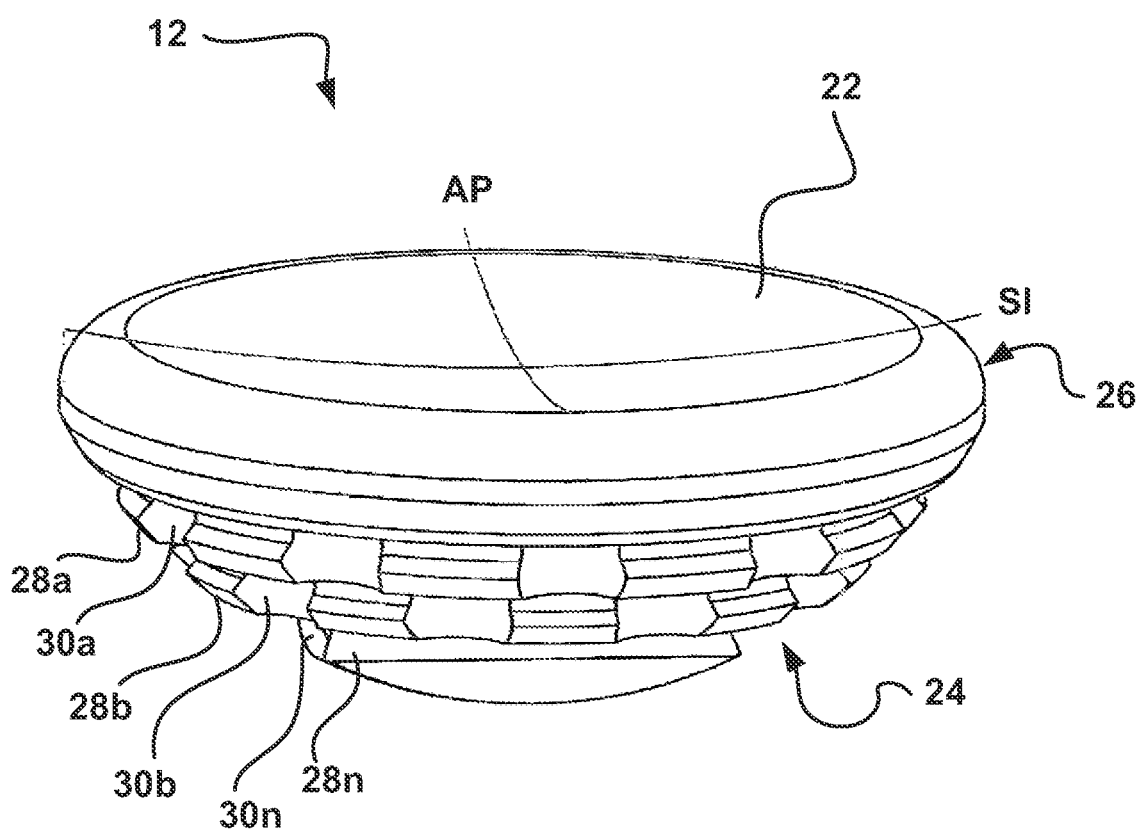
FIG. 3 illustrates an example of an implant.

The implant 12 may include a load bearing surface 22 and a bone facing surface 24. Turning now to FIG. 3, a top perspective view of an implant 12 consistent with at least one embodiment herein is generally illustrated. The load bearing surface 22 may have a contour substantially corresponding to or based on the contour of the patient's articular surface being replaced (i.e., the articular surface which is removed by the excision device 10). The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior (AP) curvature and the superior-inferior (SI) curvature. One or more of the AP and/or SI curvatures may themselves be based on multiple curves, (for example, as generally described in U.S. patent application Ser. No. 12/027,121, filed Feb. 6, 2008 and entitled SYSTEM AND METHOD FOR JOINT RESURFACE REPAIR, which is fully incorporated herein by reference). The load bearing surface 22 may be generally concaved. For example, the load bearing surface 22 may have a generally hemi-spherical shape.

The load bearing surface 22 may also include a beveled region 26 disposed about the perimeter of the load bearing surface 22. The beveled region 26 may reduce the potential of further damage to the surrounding articular surface by eliminating a hard transition between the load bearing surface 22 and the remaining articular surface. The beveled region 26 may be particularly helpful if a portion of the implant 12 is slightly proud with respect to the remaining articular surface.

The bone facing surface 24 may be configured to be generally received in the excision site created by the excision device 10. For example, the bone facing surface 24 may have a generally hemi-spherical shape substantially corresponding to the contour of the cutting surfaces 20 of the cutters 16a, 16b. The bone facing surface 24 may also include one or more lips, protrusions, ribs or the like 28a-28n configured to increase the mechanical connection between the implant 12 and the patient's bone within the excision site. Again, these lips or the like 28a-28n may generally correspond to the contours of the cutting surfaces 20 of the cutters 16a, 16b. The voids or space 30a-30n between the lips 28a-28n may create pockets for bone in-growth and/or bone cement.

Figure 4:
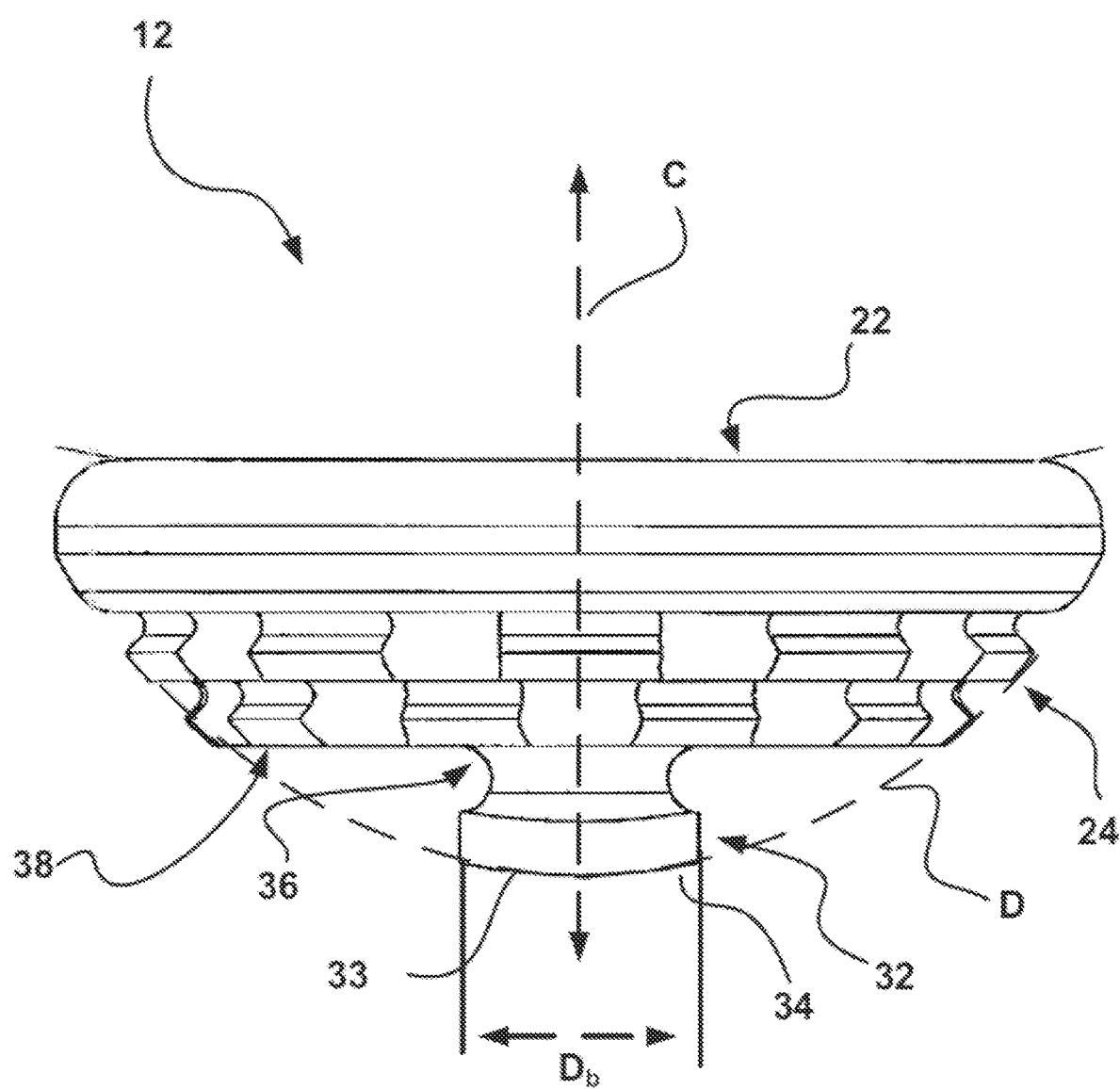
FIG. 4 illustrates a side view of an example of an implant.
Figure 5A:
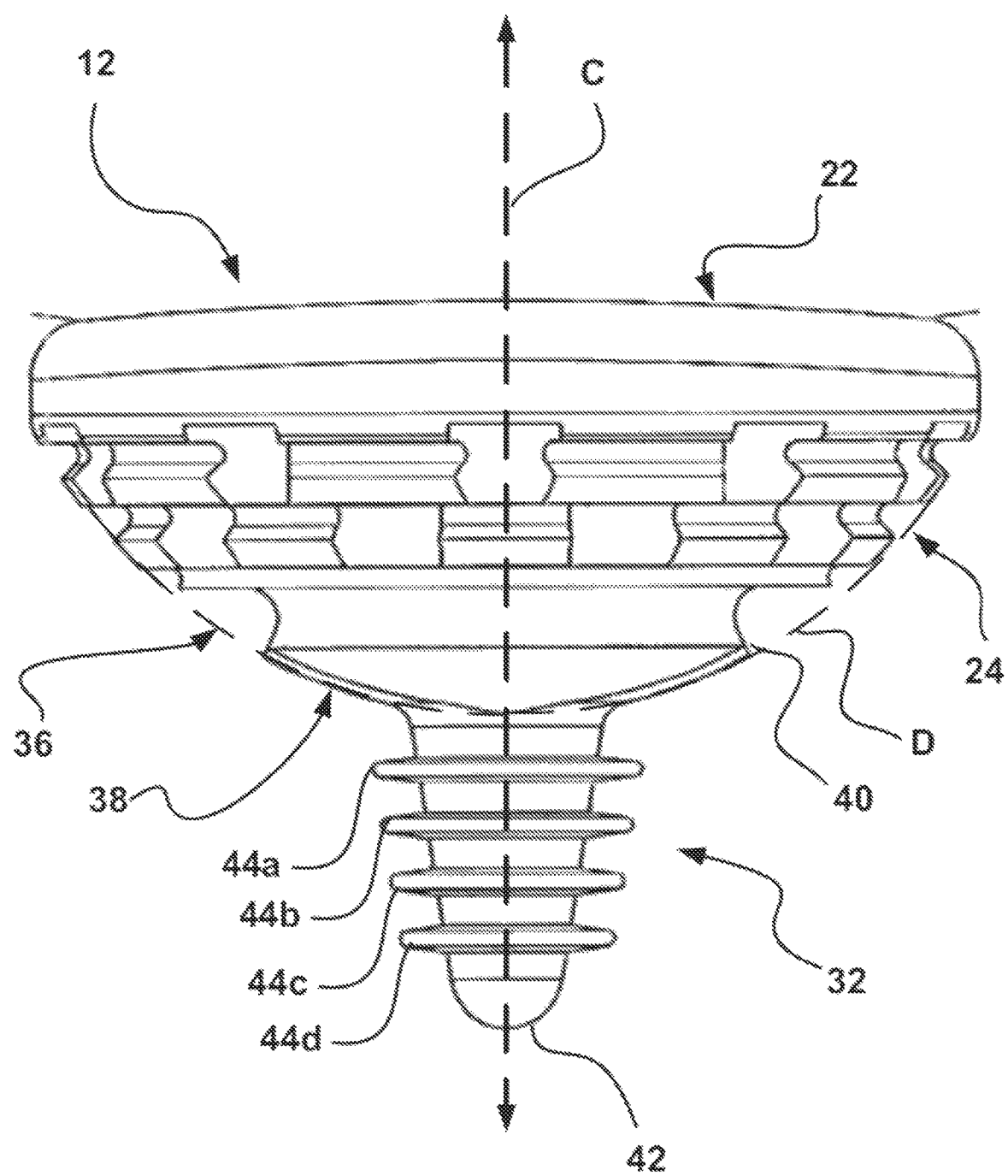
FIG. 5a illustrates a side view of another example of an implant.
Figure 5B:
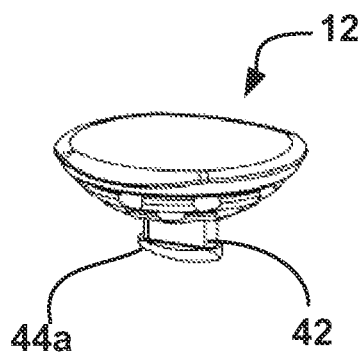
FIG. 5b illustrates a perspective view of an example of an implant.
Figure 5C:
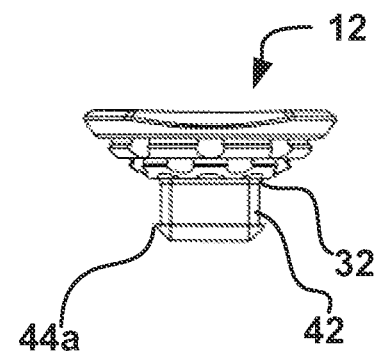
FIG. 5c illustrates a side view of an example of the implant of FIG. 5b.
Figure 5D:
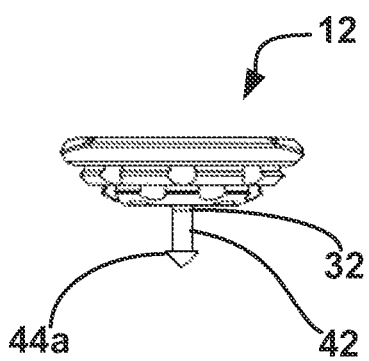
FIG. 5d illustrates another side view of an example of the implant of FIG. 5b.
Figure 5E:
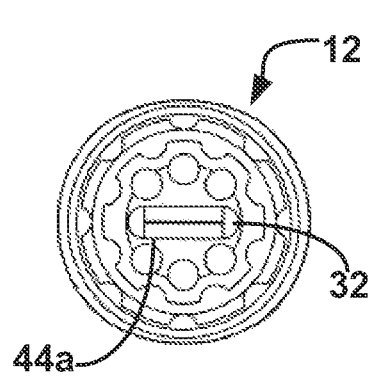
FIG. 5e illustrates a bottom view of an example of the implant FIG. 5b.
Figure 5F:
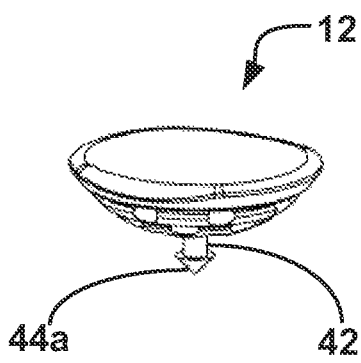
FIG. 5f illustrates a side perspective view of an example of the implant of FIG. 5b.

Turning now to FIGS. 4 and 5a, the implant 12 may optionally include at least one keel or tail 32 extending generally outwardly from the bone facing surface 24. For example, the implant 12 may include at least one keel 32 including a protrusion or button 34 disposed about a distal end of a base region 36 as generally illustrated in FIG. 4. For example, the implant 12 may include a single keel 32 extending generally downwardly and away from the bottom surface 38 of the bone facing surface 24 generally along the central axis C of the implant 12. The base region 36 may be coupled to the bottom surface 38 of the bone facing surface 24 and may have an hour-glass shape which may initially taper radially inwardly and then taper radially outwardly. The bottom surface 33 of the button 34 may have a curvature substantially corresponding to the curvature of the implant site. For example, the bottom surface of the button 34 may have a curvature (generally illustrated by dotted curve D) substantially corresponding to the curvature of the cutting surfaces 20.

The button 34 may extend generally radially outwardly from a distal end of the base region 36. As such, the button 34 may have a diameter Db greater than at least a portion of the base region 36, for example, the portion of the base region adjacent to the button 34. According to one embodiment, the diameter Db of the button 34 may be the same as or slightly larger than the diameter of the cavity in the excision site in which it is configured to be received. As such, the button 34 may form an interference fit with the cavity in the excision site which may secure the implant 12 to the bone and may also facilitate alignment of the implant 12 with respect to the articular surface and the excision site. Alternatively, the diameter Db of the button 34 may be slightly smaller than the diameter of the cavity in which it is configured to be received. As such, the button 34 may also facilitate alignment of the implant 12 with respect to the articular surface and the excision site. In addition, bone cement or the like may be disposed around the keel within the cavity to increase the mechanical connection between the keel 32 and the bone.

FIG. 5*a* illustrates another embodiment of a keel 32. The keel 32 may include a base region 36 extending generally outwardly/downwardly and away from the bottom surface 38 of the bone facing surface 24 generally along the central axis C of the implant 12. For example, the keel 32 may extend outwardly/downwardly and away from the bottom surface 38 of the bone facing surface 24 beyond the curvature D substantially corresponding to the curvature of the cutting surfaces 20. The keel 32 may be configured to be received in an additional cavity, pocket or the like formed within the excision site. The additional cavity may be formed subsequent to the formation of the excision site using an additional cutter, chisel, drill or the like (not shown).

The base region 36 may include one or more radial lips, grooves, protrusions or the like 40. The keel 32 may also include a protrusion 42 extending generally downwardly and away from the base portion 36 generally along the central axis C of the implant 12. The protrusion 42 may include one or more radial lips, grooves, protrusions or the like 44*a*-44*n*. As discussed herein, the keel 32 may be configured to engage a cavity or the like disposed within the excision site and may be configured align the implant 12 with respect to the articular surface and/or the excision site and may also increase the mechanical coupling of the implant 12 to the bone.

Figure 5G:
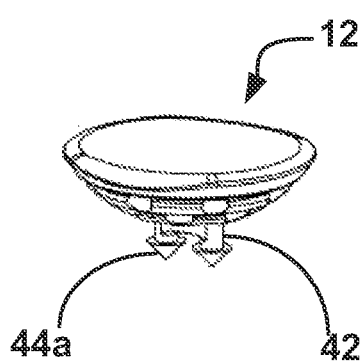
FIG. 5g illustrates a side perspective view of another example of an implant.

While the keels 32 illustrated in FIGS. 4 and 5*a* are shown having a generally concentric shape, the keel 32 may have other configurations. For example, in the embodiment illustrated in FIG. 5*b* through 5*f* the keel 32 and/or the protrusion 42 extending from the keel 32 may have a shape configured to prevent rotations of the implant 12 with respect to the articular surface. The keel 32 may have a non-circular shape configured to be received in the excision site in a lock-and-key configuration. By way of example, the keel 32 may have a generally multifaceted geometry (such as, but not limited to, rectangular, pentagonal, hexagonal or the like) configured to received in the excision site. Similarly, the protrusion 42 may exhibit a multifaceted geometry such as generally oblong or rectangular, pentagonal, hexagonal, or the like. The protrusion 42 may also exhibit an additional (or second) protrusion 44*a* extending outwardly in a radial direction from the central axis of the implant 12, which may form a raised edge or surface around the perimeter of the protrusion 42. As illustrated, protrusion 42 may end in a relatively pointed tip, or may exhibit a curvature as illustrated in FIG. 5*a*. FIG. 5*g* illustrates a further embodiment of protrusion 42, wherein the protrusion 42 may be formed from a variety of features, such as circular, rectangular, etc. It may be appreciated that, the implant 12 and the keel 32 may be a single, integral or unitary component or may be formed from two or more pieces which may be secured to each other (either permanently or removably secured).

Turning now to FIGS. 6-10, one method of installing an implant 12 consistent with the present disclosure is generally illustrated. One or more incisions 49 may be created proximate the patient's shoulder 50 to provide access to the defect 52 on the patient's articular surface 54, for example, using a scalpel or the like. The incision 49 may be made through the anterior portion of the patient. Again, the present disclosure will describe a system and method for replacing a portion of the articular surface of the glenoid; however, it should be understood that the system and method according to the present disclosure may also be used to resurface articular surfaces other than the glenoid. The system and method consistent with one embodiment of the present disclosure may allow for "key-hole" surgery in which a minimum number and size of incisions are made. As may be appreciated, "key-hole" surgery may reduce the amount of pain and/or discomfort experienced by the patient and may reduce healing times.

Figure 6:
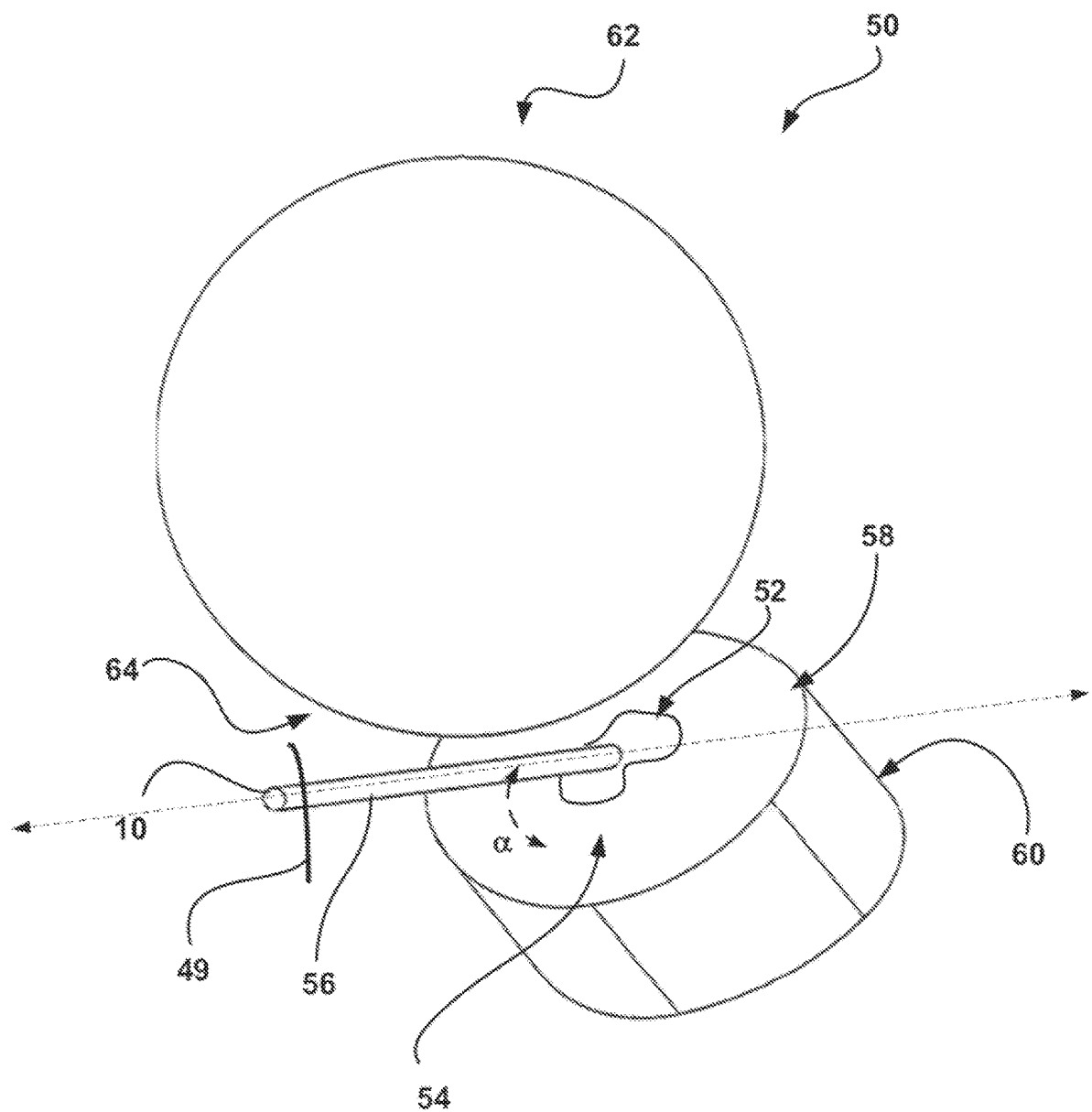
FIG. 6 illustrates an example of a guide pin positioned in the glenoid surface of a scapula.

Once the incision is created, a guide pin 56, FIG. 6, may be positioned about the glenoid 58 on the scapula 60 to provide an access passageway to the glenoidal articular surface 54 as will be described herein. Consistent with one embodiment, the guide pin 56 may comprise threaded and/or self-tapping tip (not shown) configured to be secured to the patient's bone. The guide pin 56 may be secured to the bone using a drill or the like (not shown) and at least a portion of which may be disposed proximate to and/or within the defect site 52 on the articular surface 54. Optionally, a drill guide (not shown) may be used to facilitate alignment of the guide pin 56 with respect to the articular surface 54.

The guide pin 56 may be disposed at an angle α relative to the articular surface 54. Angle α may be less than or equal to 90 degrees, wherein α≤90 degrees with respect to the articular surface 54. In some examples, angle α may be less or equal to 90 degrees and greater than or equal to 45 degrees with respect to the articular surface 54, wherein 45 degrees≤α≤90 degrees with respect to the articular surface 54. In further examples, 90 degrees>α>45 degrees and/or 90 degrees>α≥45 degrees, with respect to the articular surface 54. The degree of the angle α may depend on the location and/or size of the defect 52 and may be selected to avoid contact with the humerus 62. In some circumstances, the degree of the angle α may also be selected to avoid contact with the perimeter of the articular surface 54.

Figure 7:
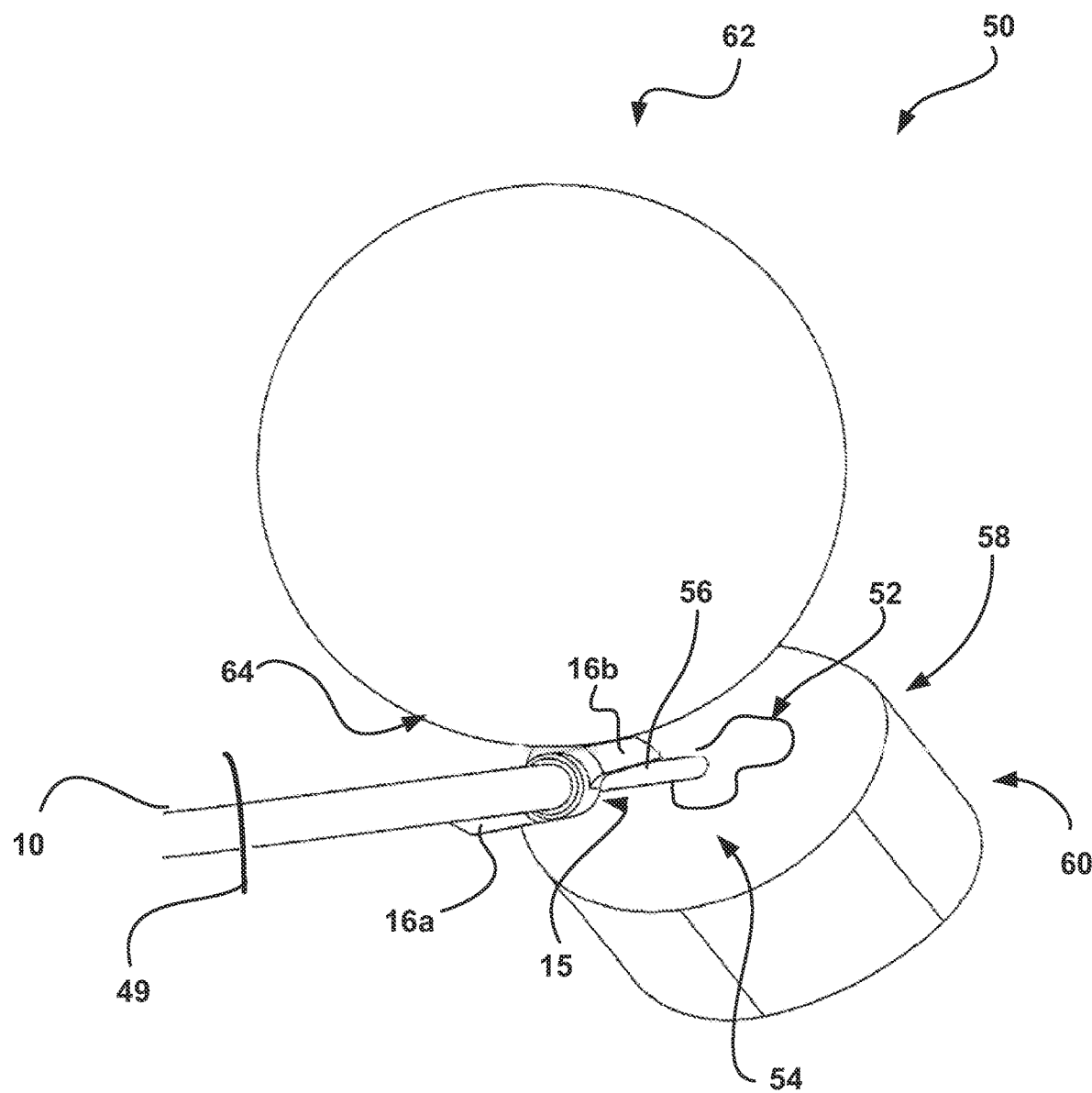
FIG. 7 illustrates an example of an excision device including a cannulated shaft and a cutter positioned at the distal end of the cannulated shaft passing over the guide pin positioned in the glenoid surface of a scapula.

Once the guide pin 56 is secured to the articular surface 54, the excision device 10 may be advanced over the guide pin 56 as generally illustrated in FIG. 7. For example, the guide pin 56 may be received within the passageway 15 defined by the cannulated shaft 14. According to at least one embodiment, the cutters 16*a*, 16*b* may be generally aligned in a single plane extending along the longitudinal axis of the excision device 10.

Figure 8:
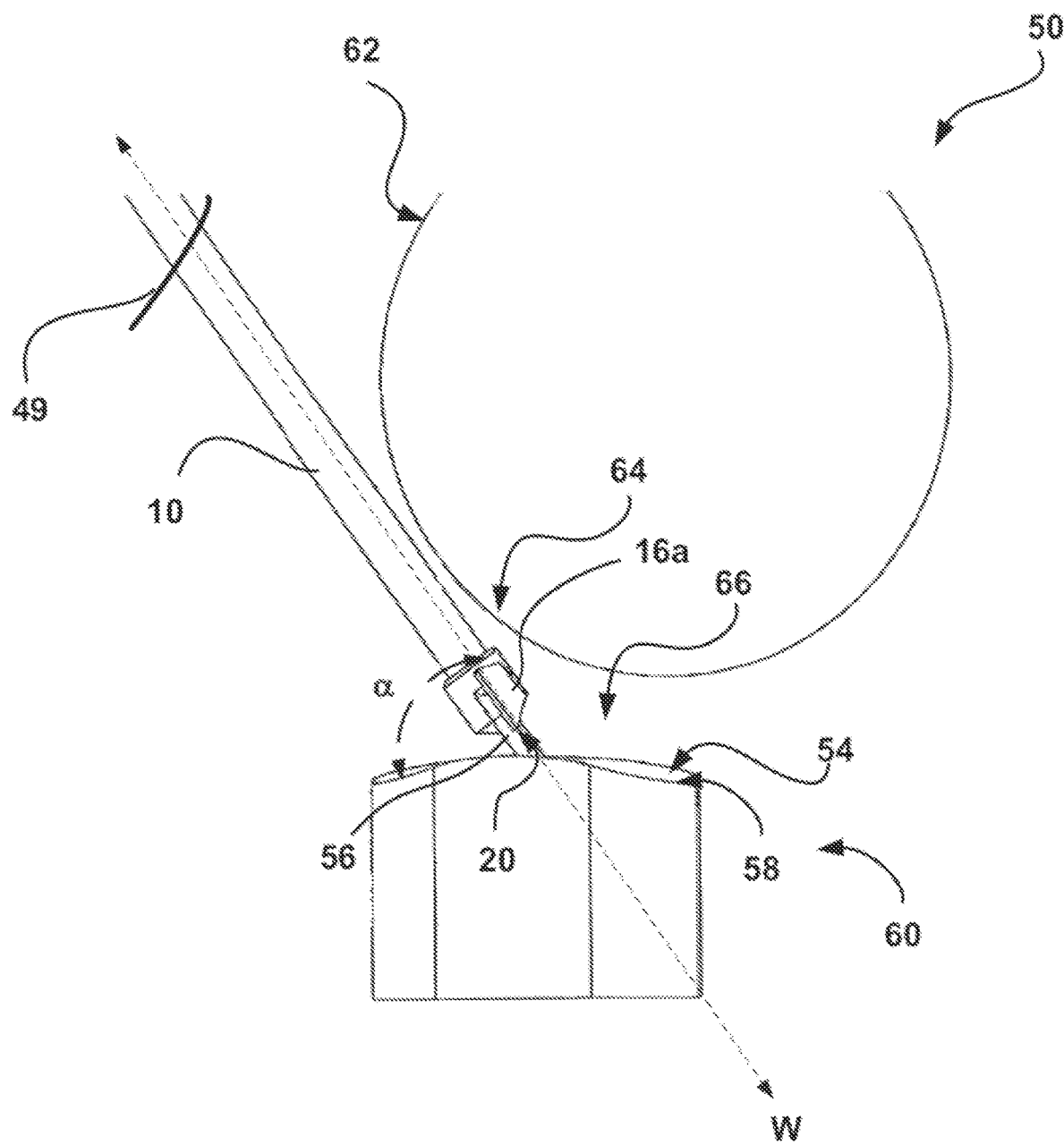
FIG. 8 illustrates a side view of an example of an excision device including a cannulated shaft and a cutter positioned at the distal end of the cannulated shaft passing over the guide pin positioned in the glenoid surface of a scapula.

The plane of the cutters 16*a*, 16*b* may be orientated generally tangential to the articular surface 64 of the humerus 62 such that the cutters 16*a*, 16*b* may slide by the articular surface 64 of the humerus 62 and between the humerus 62 and the scapula 60 as generally illustrated in FIGS. 7 and 8.

Once the cutters 16*a*, 16*b* are advanced over the guide pin 56 to the articular surface 54, the excision device 10 may be rotated about the guide pin 56. As may be best seen in FIG. 8, a pocket of cavity 66 may be present between the articular surface 54 of the glenoid 58 and the articular surface 64 of the humerus 62. The cutters 16*a*, 16*b* of the excision device 10 may therefore rotate about the guide pin 56 without contacting the articular surface 64 of the humerus 62. The cutters 16*a*, 16*b* may have generally flat cutting surfaces 20, forming a point along the length thereof, or may have serrated cutting surfaces.

Figure 9:
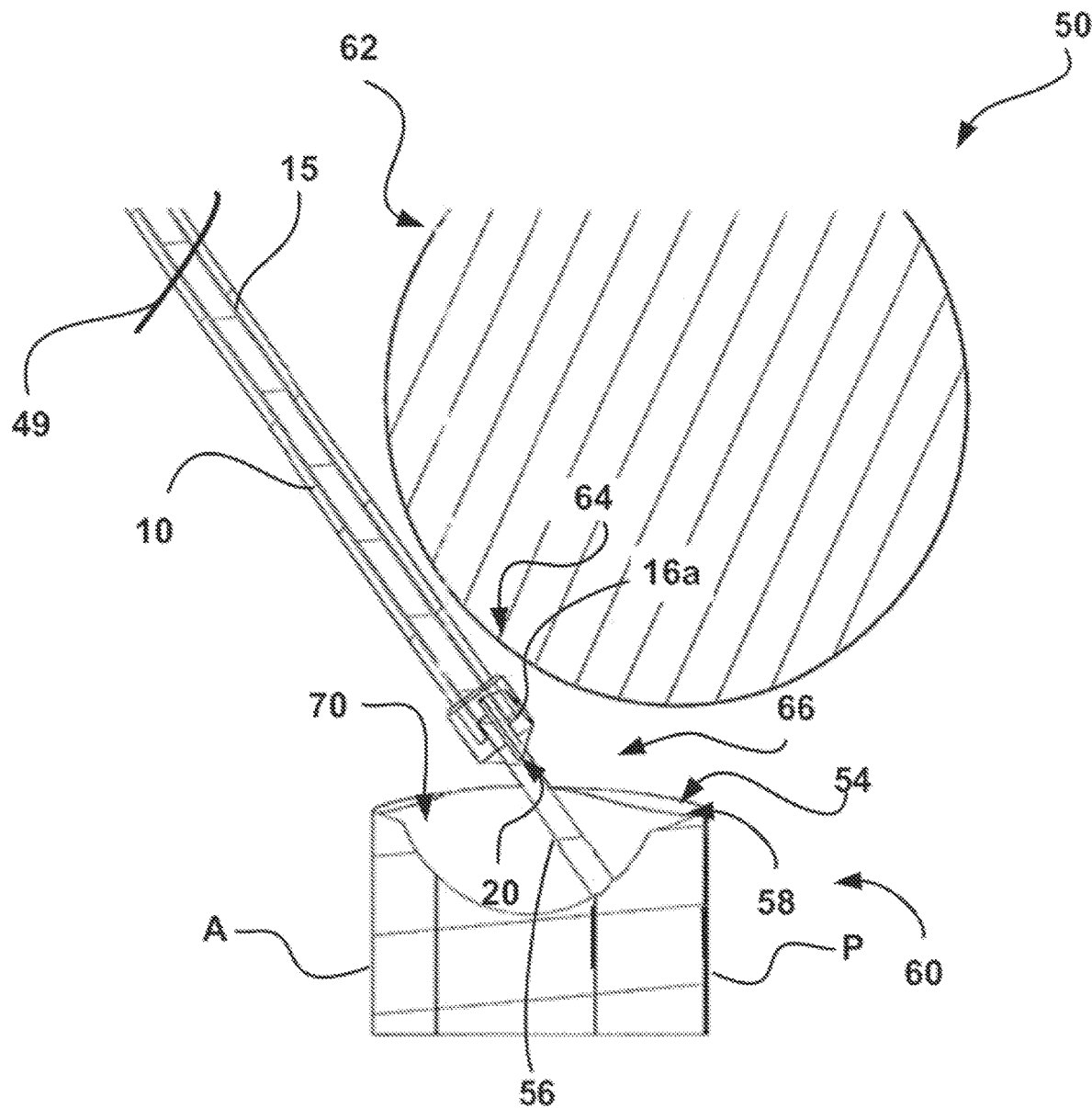
FIG. 9 illustrates a side-cross sectional view of an excision device including a cannulated shaft and a cutter positioned at the distal end of the cannulated shaft passing over the guide pin positioned in the glenoid surface of a scapula.

The excision device 10 may thus be rotated about the guide pin 56 to form an excision site 70 within the articular surface 54 of the glenoid 60 as generally illustrated in FIG. 9. Due to the contour of the cutting surfaces 20 of the cutters 16*a*, 16*b*, the excision site 70 created by the excision device 10 may have a generally hemi-spherical configuration regardless of the angle α of the guide pin 56.

Figure 10:
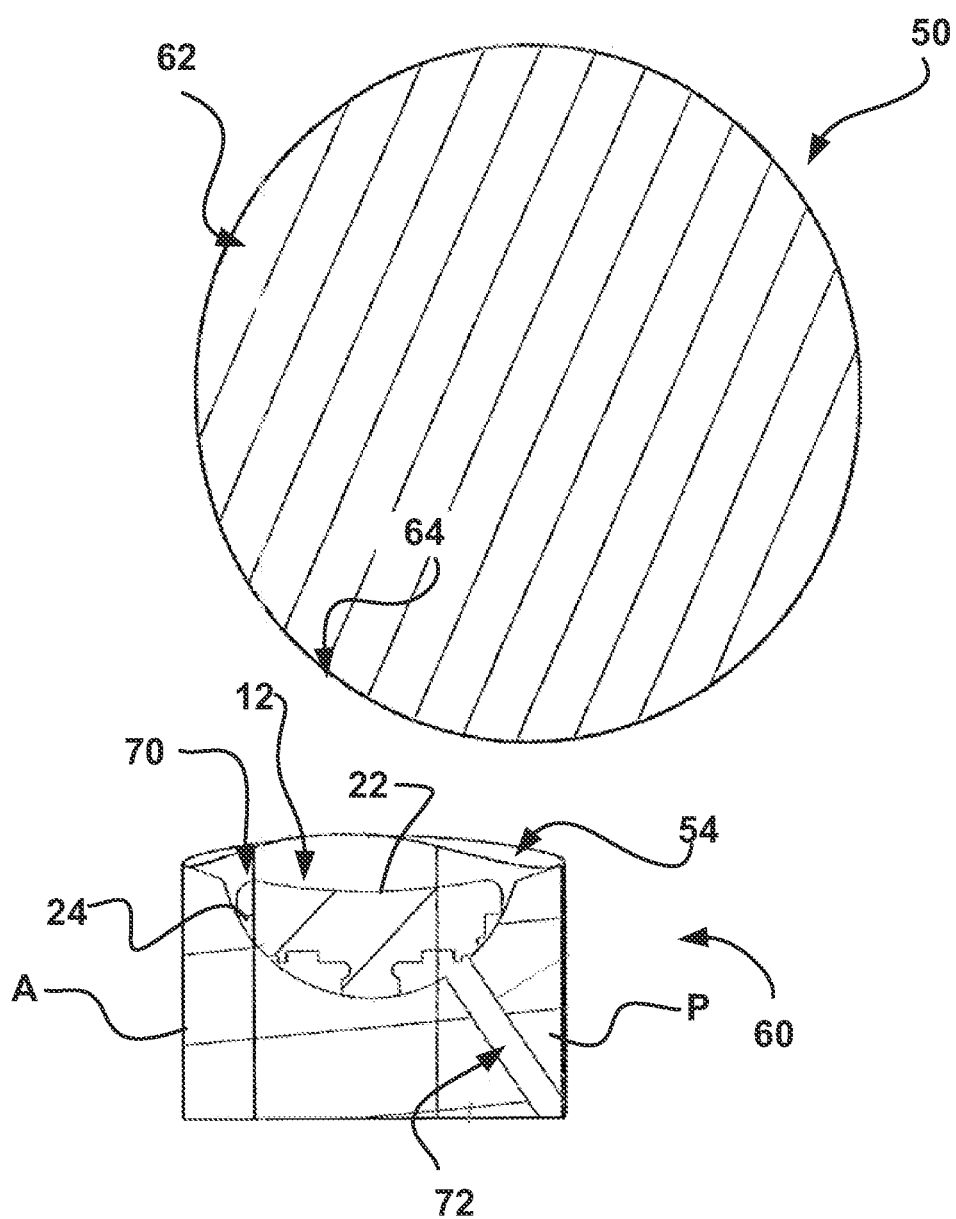
FIG. 10 illustrates a side-cross sectional view of an excision site including an implant.

Once the excision site 70 is formed within the articular surface 54, the excision device 10 and the guide pin 56 may be removed as generally illustrated in FIG. 10. The removal of the guide pin 56 may leave a cavity 72 formed by the distal tip of the guide pin 56. The implant 12 may then be received in the excision site 70. The spherical configuration of the excision site 70 may normalize the implant 12 with respect to the remaining articular surface 54. The load bearing surface 22 of the implant 12 may substantially match the original contour of the patient's articular surface 54 which was removed.

Figure 11:
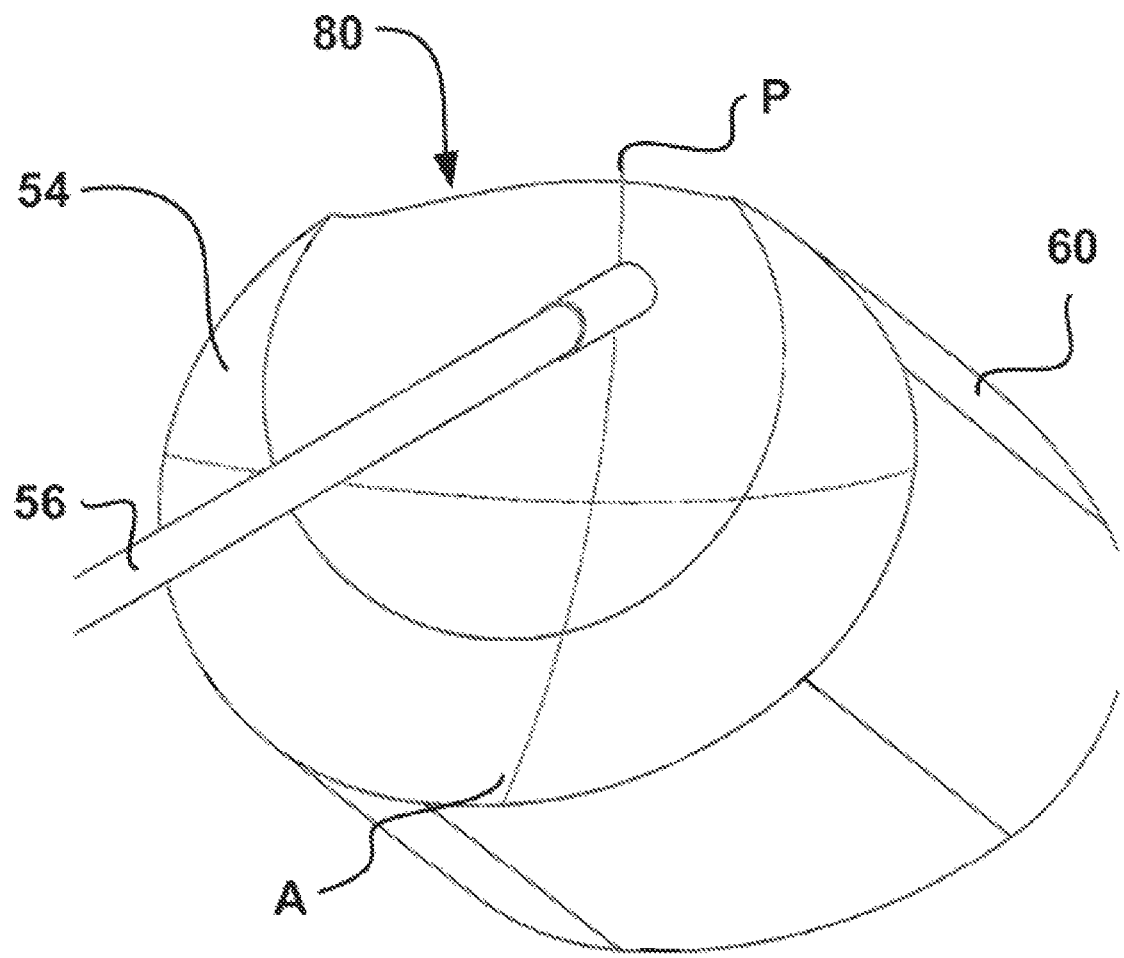
FIG. 11 illustrates an example wherein a portion of the perimeter of the articular surface is damaged and the guide pin is positioned such that a repair may be made at or near the perimeter of the articular surface.

As illustrated in FIG. 11, the system and method according to the present disclosure may also repair a defect 80 on the articular surface 54 in which a portion of the perimeter of the articular surface 54 is damaged or missing. For example, the posterior portion P of the articular surface 54 may have a defect 80 wherein a portion of the perimeter of the articular surface 54 is missing which may be caused by advanced chronic shoulder dislocation and/or early onset arthritis. To repair a defect 80 proximate the perimeter of the articular surface 54, the guide pin 56 may be moved further towards the posterior end P of the articular surface 54. The exact location of the guide pin 56 with respect to the articular surface 54 may depend on the location and size of the defect 80 as well as the size of the cutters 16a, 16b of the excision device 10.

Figure 12:
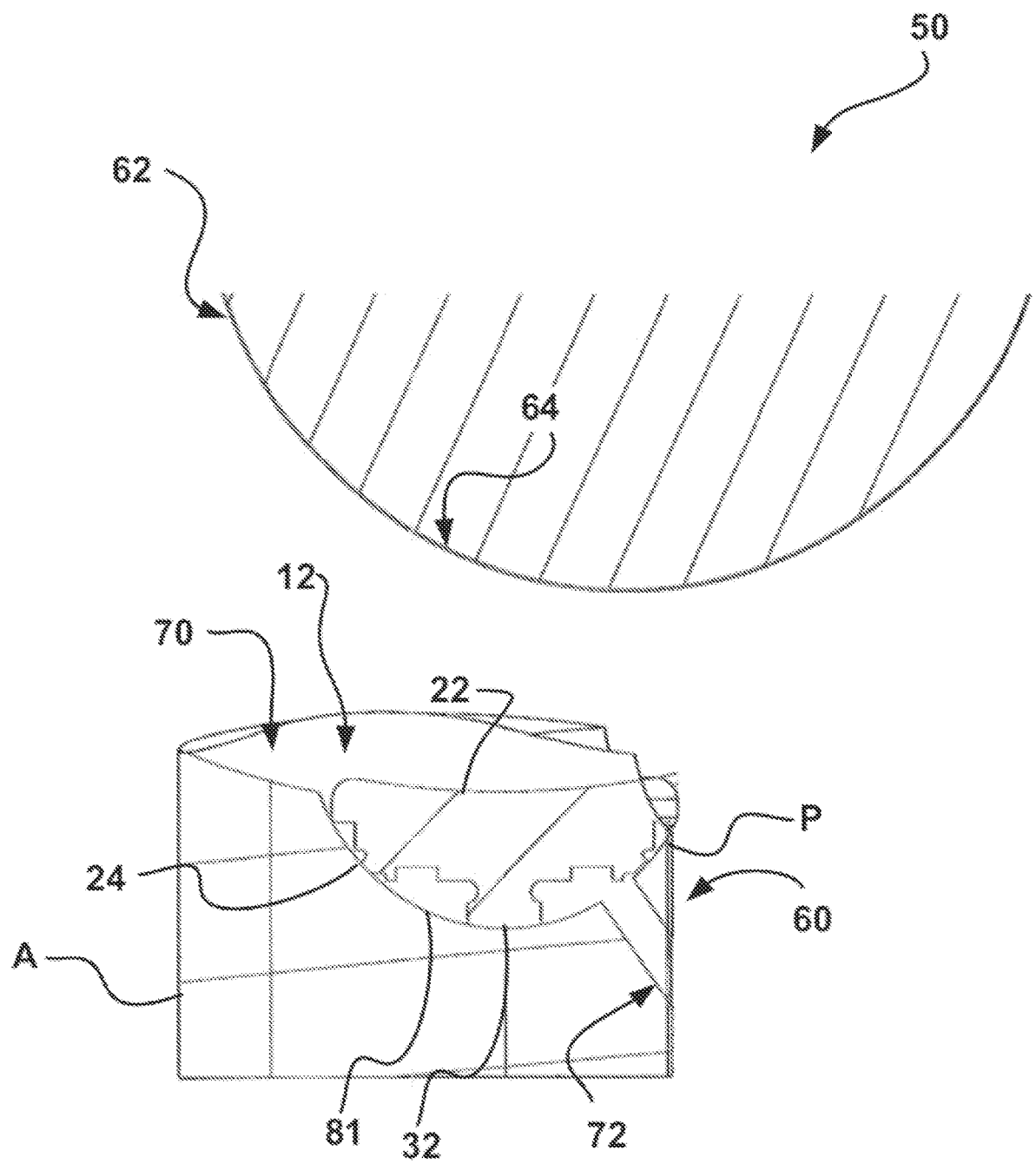
FIG. 12 illustrates a side-cross sectional view of an excision site including an example of an implant positioned at or near the perimeter of the articular surface.

According to one embodiment, the guide pin 56 may be located a distance away from the perimeter of the articular surface 54 which generally corresponds to the radius $R_e$ of the cutters 16a, 16b. The excision device 10 may be advanced over the guide pin 56 and rotated as described herein. Accordingly, the cutters 16a, 16b may remove a portion of the articular surface 54 to form an excision site 81 disposed about the perimeter of the articular surface 54 as generally illustrated in FIG. 12. The excision device 10 and the guide pin 56 may then be removed and the implant 12 may be received within the excision site 81. As may be seen in FIG. 12, a portion of the implant 12 may replace the perimeter of the articular surface 54 which was damaged and/or missing.

Figure 13:
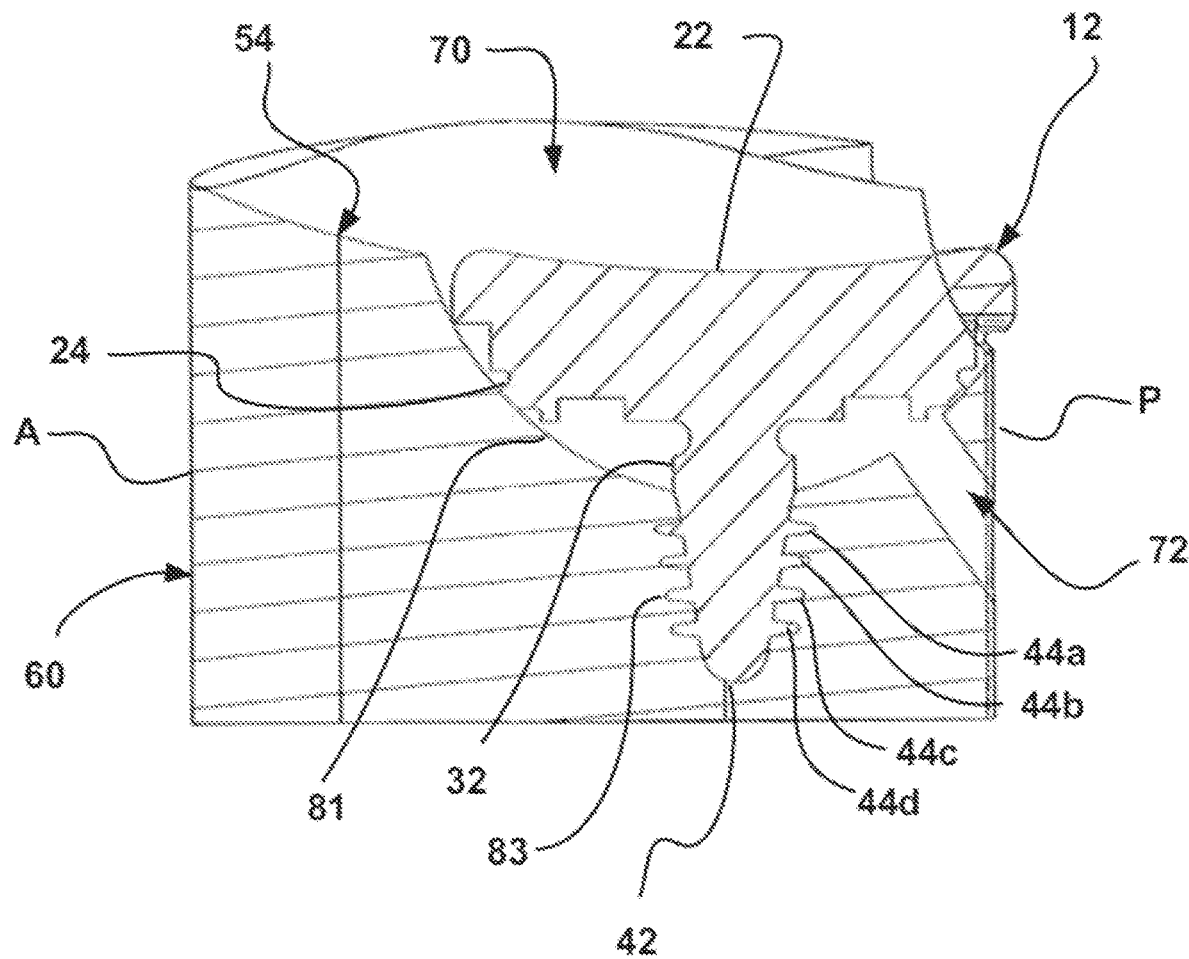
FIG. 13 illustrates an example of a side-cross sectional view of an example of an excision site including an example of an implant positioned at or near the perimeter of the articular surface.

The implant 12 may also include a keel 32 as generally illustrated in FIGS. 12 and 13. The keel 32 may facilitate alignment of the implant 12 with respect to the articular surface 54 and/or may provide an increased mechanical connection between the implant 12 and the bone. As discussed herein, the excision site 81 may also include one or more cavities 83, FIG. 13, configured to received at least a portion of the keel 32 (for example, but not limited to, one or more radial lips 44a-44n of the protrusion 42.

Once the position/orientation of the implant 12 has been confirmed (i.e., the contour of the load bearing surface 22 has been confirmed along the AP and/or SI planes to generally correspond to the original contour of the articular surface), the implant 12 may be secured to the bone. The implant 12 may be held in place by the lips, protrusions, ribs or the like 28a-28n of the bone facing surface 24, the keel 32, and/or bone cement or the like.

Turning to FIGS. 14-21, one system and/or method for locating an implant 12 consistent with the present disclosure is generally illustrated. The description of the system and methods herein are not limited to the treatment of any single articular surface of the glenoid and may apply not only to the one or more articular surfaces that may be present in the glenoid but to other articular surfaces through out the body as well.

Figure 14A:
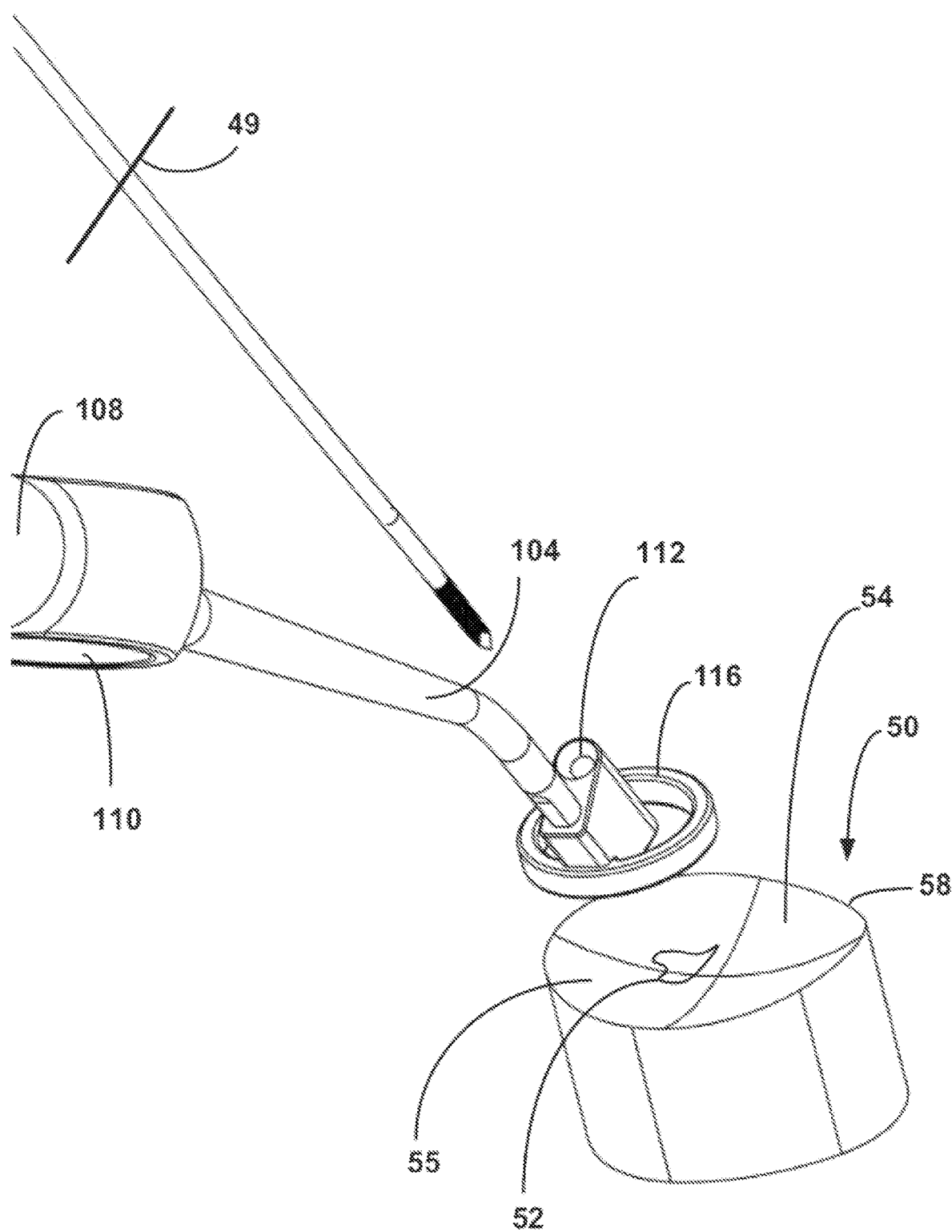
FIG. 14A illustrates an example of perspective view of an example of an excision guide and guide pin relative to an articular surface of a glenoid.

One or more incisions 49 may be created proximate to the patient's shoulder 50 to provide access to the defect on the patient's articular surface 54, using, for example, a scalpel or the like. As may be appreciated, the glenoid may include one or more articular surfaces 54. Each of the articular surfaces may define a concavity as illustrated in FIG. 14a.

Figure 14B:
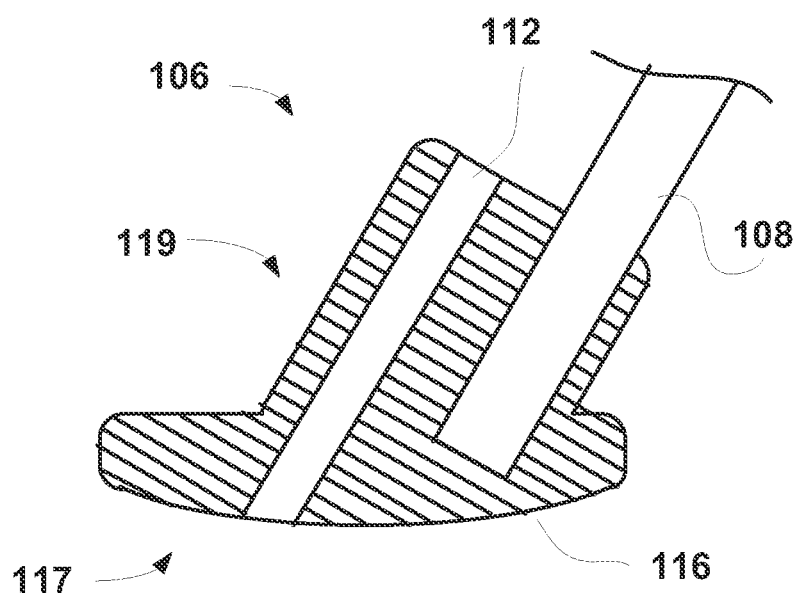
FIG. 14B illustrates a cross-section view of a side view of an embodiment of an excision guide.
Figure 14C:
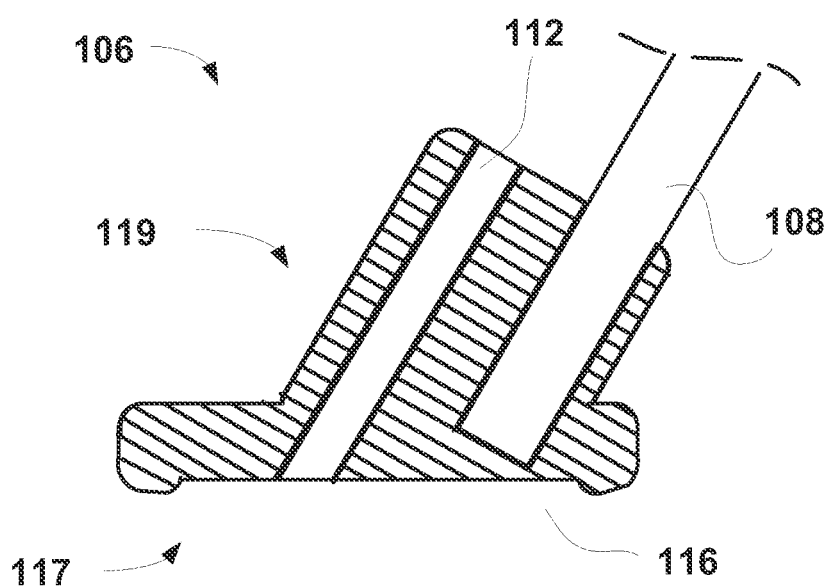
FIG. 14C illustrates a cross-sectional view of a side view of another embodiment of an excision guide.

A portion of an excision guide 102 may be positioned within the incision and located between the humerus 62 and the articular surface 54 of the glenoid 58. The excision guide may include an arm 104 and a head 106, which may, in some embodiments, be inserted through the incision in such a manner to avoid contact with the humerus 62. FIGS. 14b and c illustrate embodiments of the excision guide head 106 and, in particular, variations in the contact surfaces 116 of the excision guide head 106 located on the lower portion 117 of the excision guide head 106. For example, in one embodiment, illustrated in FIG. 14b, the contact surface 116 may generally conform to the articular surface 54. In another embodiment, illustrated in FIG. 14c, the contact surface 116 may be a ring near the periphery of the lower portion 117 of the excision guide head 106. As may be appreciated in some embodiments, when in the shape of a ring, the contact surface may be continuous or may, in other embodiments, be discontinuous forming ridges around the contact surface 116. The excision guide 102 may also include a handle 108, which may or may not include one or more indentations 110 to assist in manipulation and/or stabilization of the excision guide 102. The handle may be affixed to the upper portion of the excision guide head 119.

The head 106 of the excision guide 102 may be located over a defect 52 of an articular surface 54. The head 106 may locate the excision guide 102 relative to the articular surface 54. In some embodiments, the head 106 may be generally centered on the articular surface 54 including the defect 52. For example, in one embodiment, the head 106 may be located generally centered in the concavity 55 of the articular surface 54. Once the head 106 is positioned over the defect 52, the guide pin 56 may be received into and pass through a guide sleeve 112 disposed on the head 106. As illustrated in FIGS. 14b and c, the guide sleeve 112 may define an opening from the upper surface 119 of the excision guide head 106 through the lower surface 117 of the excision guide head 106. The guide sleeve 112 may position the guide pin 56 relative to the defect 52 on the articular surface. In addition, the guide sleeve 112 may be formed in and/or integral to the head 106 or may be formed in an insert connected to the head 106.

Figure 15:
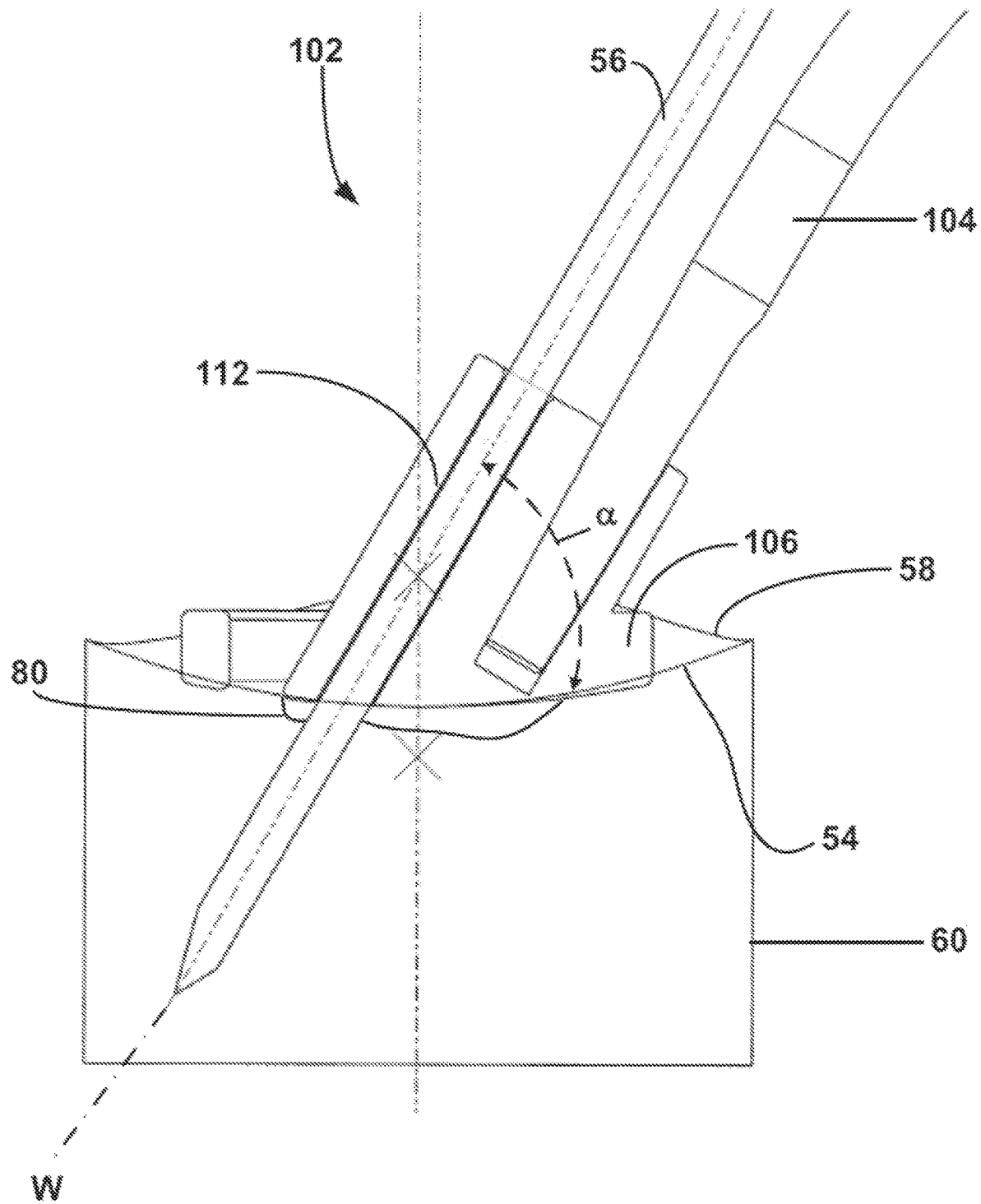
FIG. 15 illustrates a cross-sectional view of the side view of an example of an excision guide having a guide pin positioned therethrough, wherein at least a portion of the guide pin is disposed in an articular surface.

As illustrated in FIG. 15, the excision guide 102 may orient the working axis (W) of the guide pin 56 in one or more planes. For example, in one aspect, the guide sleeve 112 may angle the guide pin 56, such that the guide pin may be positioned at an angle α that may be 90 degrees or less from the articular surface, including all values and increments in the range of 10 degrees to 90 degrees, such as in one embodiment 45 degrees to 75 degrees or in a further embodiment 60 degrees from the articular surface 54.

Figure 16:
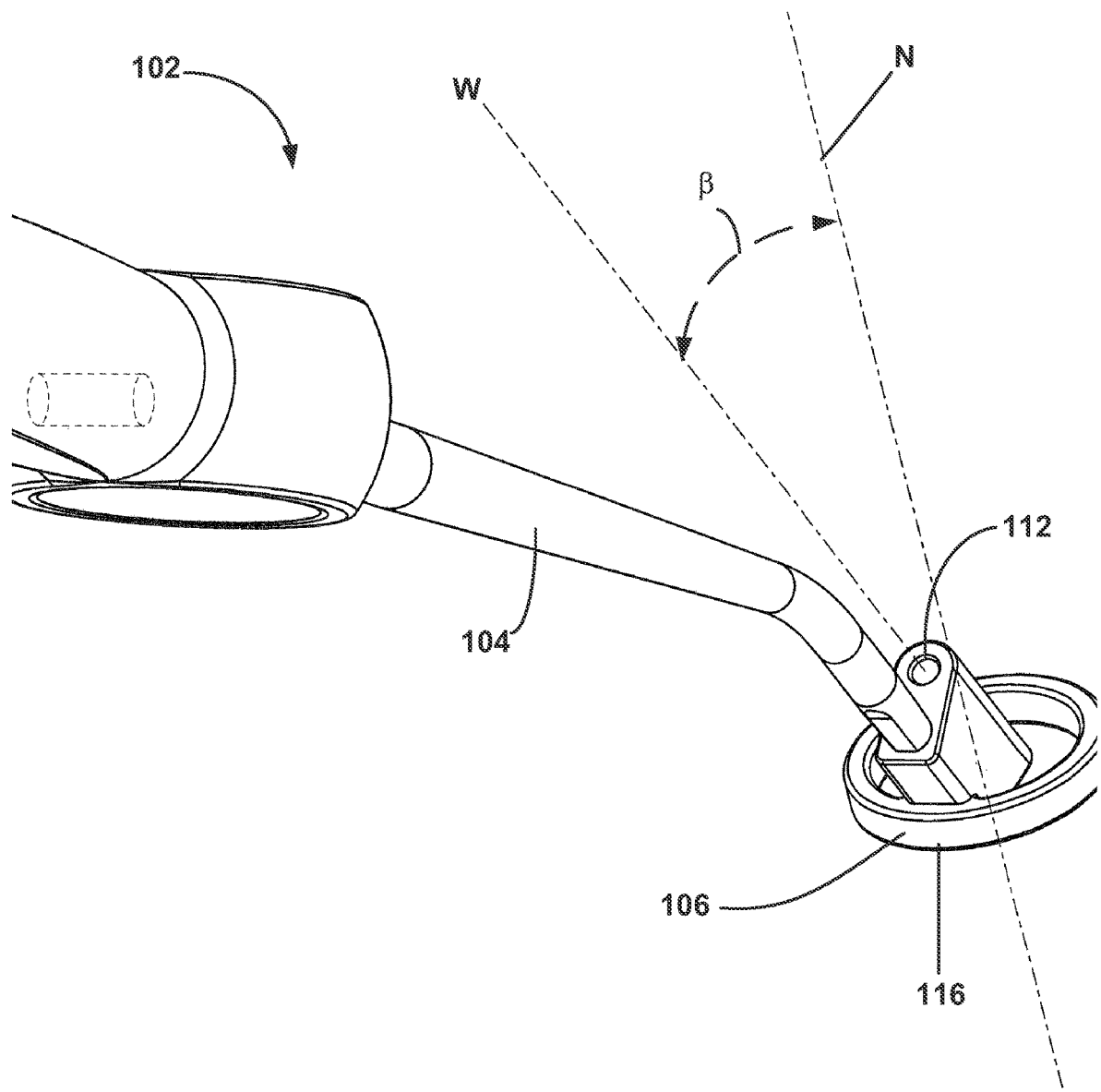
FIG. 16 illustrates a perspective view of an example of an excision guide.

In another aspect, the guide sleeve 112 of the excision guide 102 may orient the working axis (W) of the guide pin 56 at an angle β relative to a normal axis (N). The normal axis (N) may, in some embodiments, be generally normal and central to a defect 80 in the articular surface 54. Angle β may be 90 degrees or less and in some examples, including all values and increments in the range of 5 degrees and 80 degrees, such as in the range of 10 degrees to 30 degrees. FIG. 16 illustrates another example of the working axis (W) defined by the guide sleeve 112 to an axis (N) generally central and normal to the lowest point of the contact surface 116 of the excision guide head 106, which may correspond to the axis generally normal and centrally located to defect 80 or to the deepest point of the excision site 70.

Figure 17:
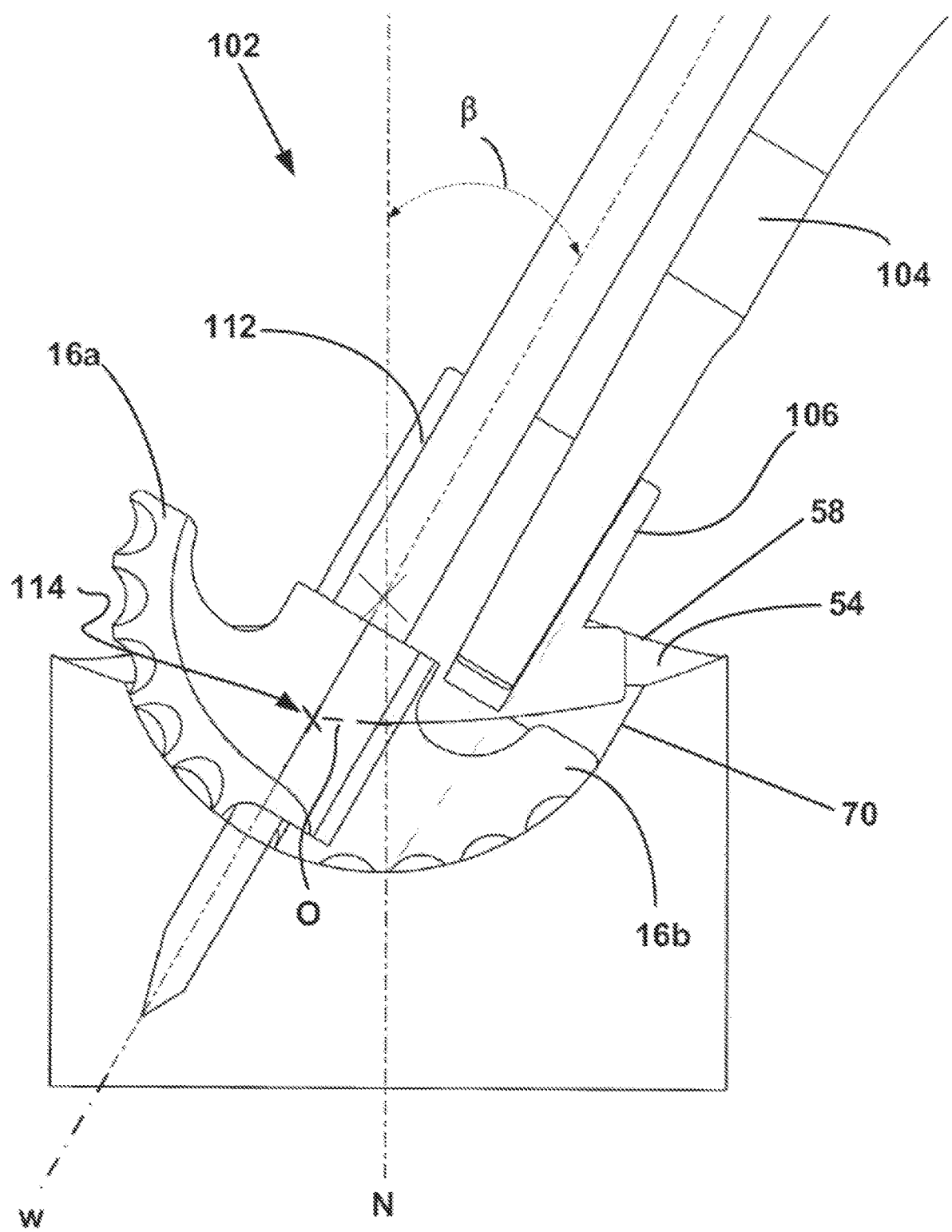
FIG. 17 illustrates a cross-sectional side view of an example of a excision device including at least one cutter portioned over a guide pin and relative to the excision guide.

The guide sleeve 112 may also offset the intended entry point 114 of the guide pin 56 in the articular surface 54 radially outward from the axis (N) normal and generally central to the excision site and/or the articular surface 54. FIG. 17 illustrates an embodiment of the positioning of the at least one cutter 16a, 16b relative to the positioning of the excision guide 102. In one embodiment, the offset (O) may be determined based on the angle of entry of the guide pin 56 ($\alpha$ or $\beta$) into the articular surface 54 and/or the depth of the desired excision site, or the height of the desired implant. For example, the offset (O) may be proportional to the angle $\alpha$ of the guide pin 56 to the articular surface 54 or angle $\beta$ of the guide pin 56 to the normal axis (N).

The working axis (W) may be positioned at an angle $\beta$ in the range of 10 degrees to 90 degrees, such as in one embodiment, 15 degrees to 45 degrees, or in a further embodiment 60 degrees from the normal axis (N). As may be appreciated, in some embodiments, the surface of the excision guide head 116 may exhibit some degree of curvature and may be convex. The curvature of the surface of the excision guide head 116 may be configured to generally match the curvature of at least a portion of the articular surface 54. In some embodiments, it may be appreciated, that the curvature of the articular surface 54 and the surface of the excision guide head may not match exactly but may provide a "close fit" sufficient to locate the excision guide head 106 within the glenoid 58. In some non-limiting embodiments, the curvature of the excision guide head surface 116 may be generally hemispherical, including pyriform or teardrop in shape.

Figure 18:
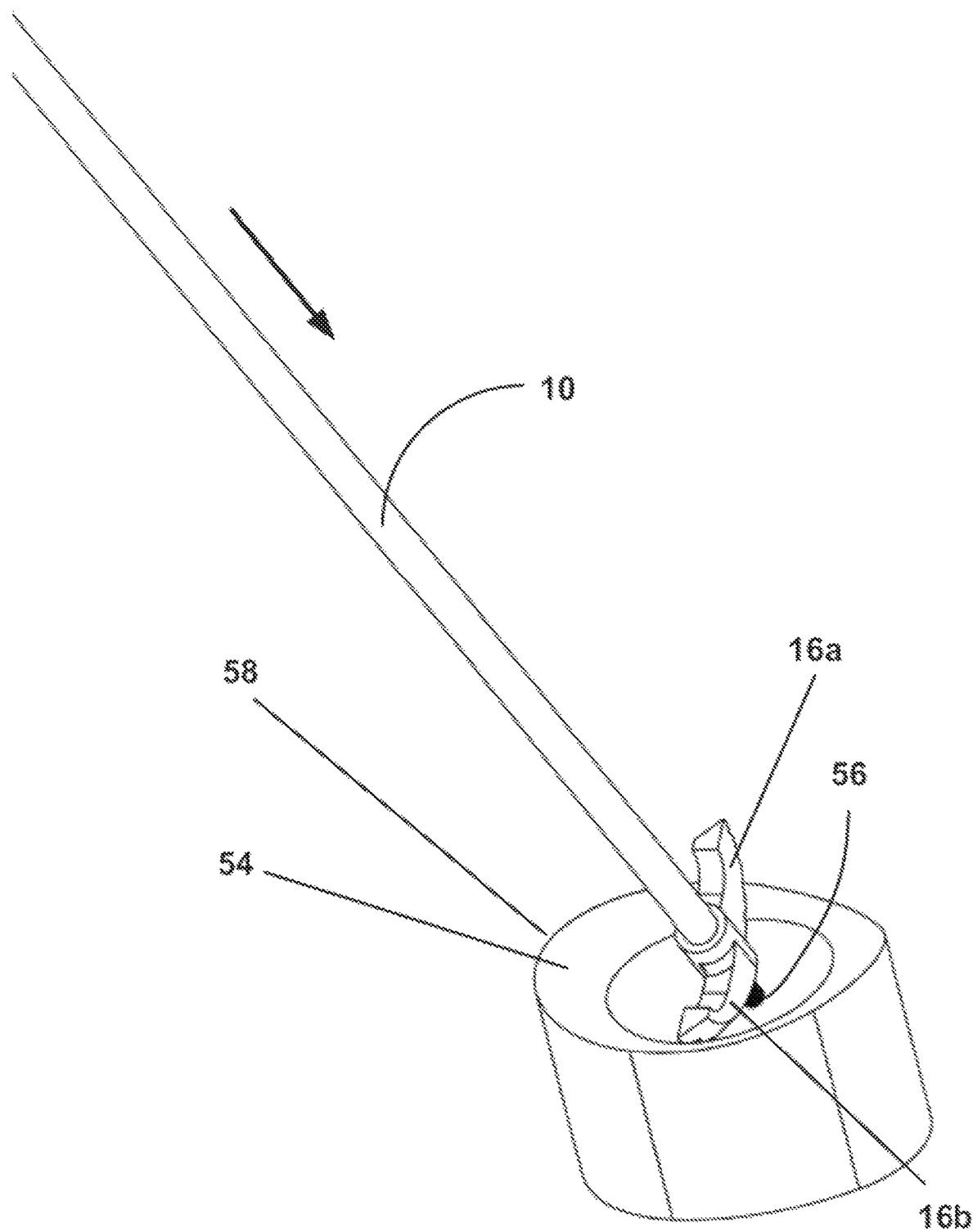
FIG. 18 illustrates a perspective view of an example of an excision device advance over a guide pin.

Once the guide pin 56 is positioned in the articular surface 54 of the glenoid 58, as illustrated in FIG. 15, the excision guide 102 may be removed from the glenoid 58 by sliding the excision guide 102 up the guide pin 56 away from the glenoid 58. As illustrated in FIG. 18, the excision device 10, including one or more cutters 16a and 16b, may be slid (in direction of arrow) over the guide pin 56 and, as described above, the excision device 10 may be rotated forming an excision site 70 in the articular surface 54.

Figure 19A:
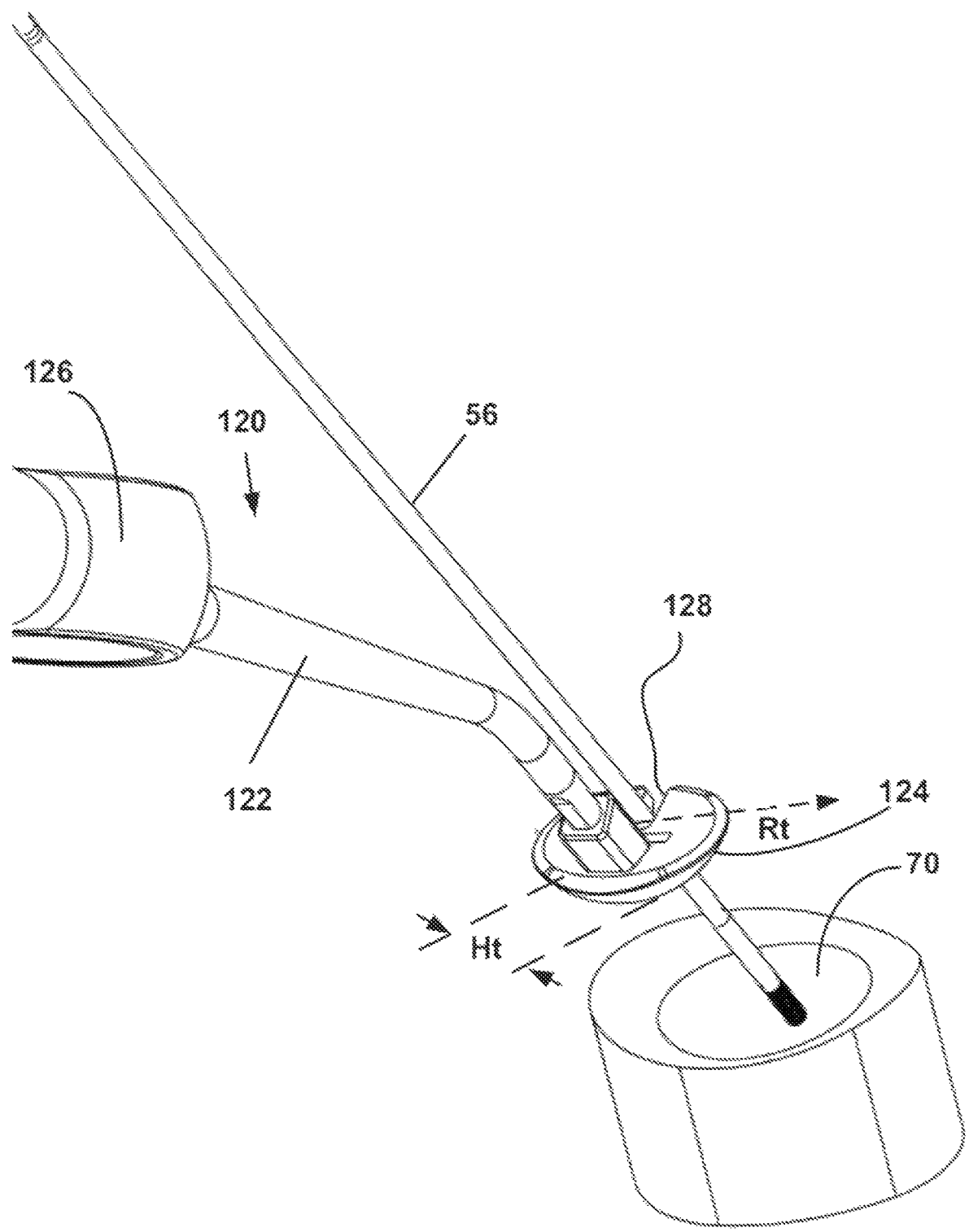
FIG. 19a illustrates a perspective view of an example of an impact guide received by a guide pin.
Figure 19B:
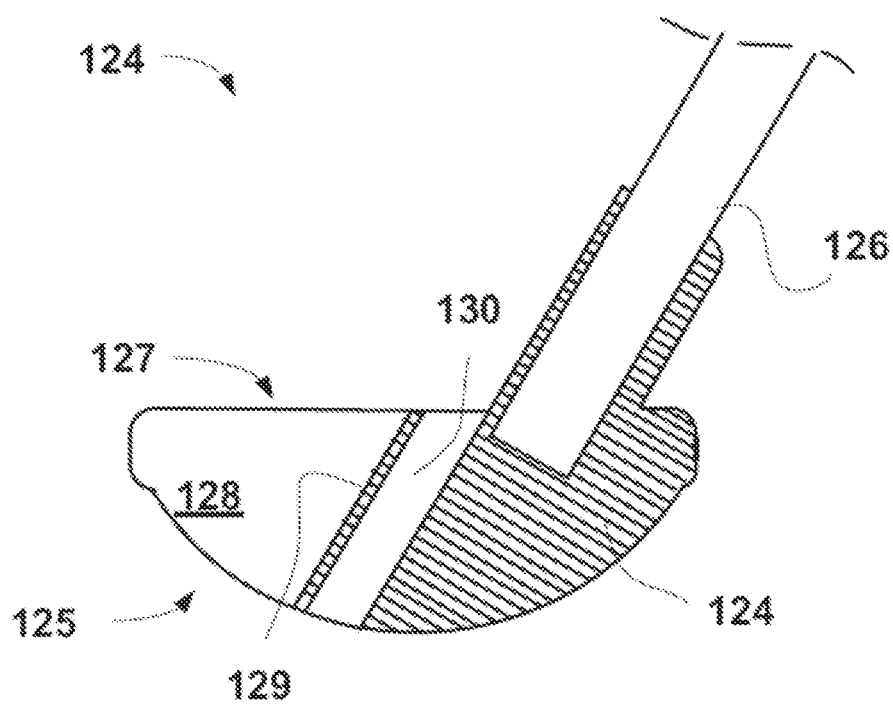
FIG. 19b illustrates a cross-sectional view of one embodiment of an impact guide.
Figure 19C:
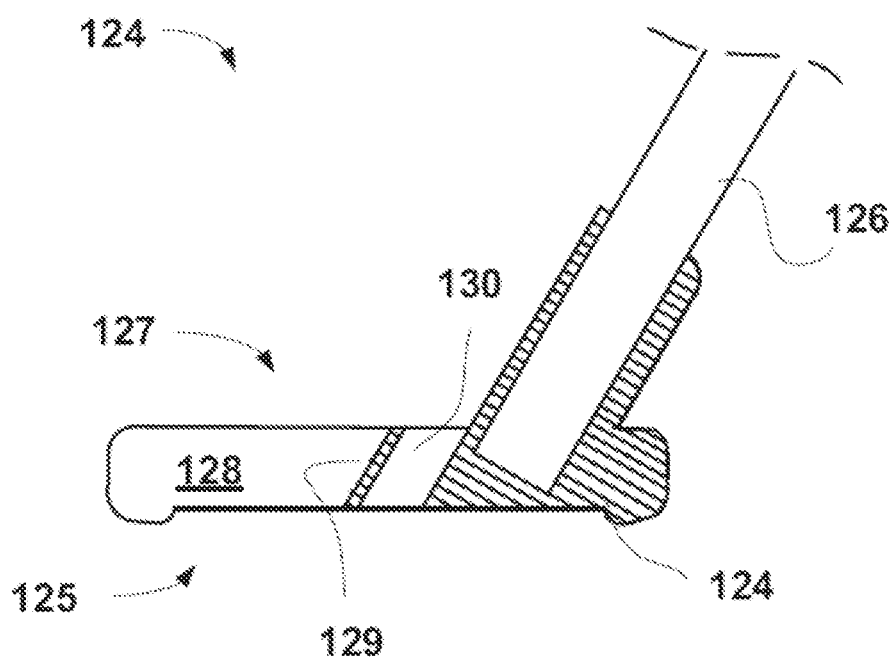
FIG. 19c illustrates a cross-sectional view of another embodiment of an impact guide.

The excision device 10 may then be removed from the guide pin 56 and an impact guide 120 may be inserted through the incision 49 and over the guide pin 56, an embodiment of which is illustrated in FIGS. 19a through 19c. The impact guide 120 may include an impact guide arm 122, an impact guide head 124 and an impact guide handle 126. In one embodiment, the impact guide 120 may be the same as the excision guide 102, wherein the head 106 of the excision guide 102 may be interchangeable with the one or more impact guide heads 124. In another embodiment, the impact guide 120 may be separately provided from the excision guide 102.

As may be appreciated, the impact guide heads 124 may generally correspond to or mimic the size and shape of an implant, described above. An embodiment of an impact guide head is illustrated in FIG. 19b, wherein the impact guide head 124 may include a lower portion 125 that substantially conforms to the generally hemispherical excision site. The impact guide head may exhibit a given height $H_t$ and radius $R_t$ matching that of an implant to be provided in the excision site 70 (see FIG. 19a). In another embodiment, illustrated in FIG. 19c, the impact guide may include a lower portion 127 that includes a ring or bevel around the periphery that may conform to the excision site. The remainder of the lower portion 125 may be recessed.

The impact guide head 124 may include a guide notch 128, which may be inserted over the guide pin 56 or around the guide pin 56 (as illustrated in FIG. 19a). It may be appreciated that while a notch is illustrated defining an opening in the periphery of the impact guide head 124, i.e., extending to the periphery of the impact guide head 124, the guide notch 128 may also include a sleeve defined in the impact guide head 124. As illustrated in FIGS. 19b and 19c, the guide notch 128 may generally define an opening from the upper portion 127 through the lower portion 125 of the impact guide head 124. In addition, the guide notch 128 may include at least one surface 129 that may accommodate the angle and offset of the guide pin 56 relative to the articular surface 54, such that the impact guide head 124 may be positioned generally central within the excision site 70 and the guide pin 56 may rest on the surface 129.

Upon placement of the impact guide head 124 by the impact guide 120 into the excision site 70, a determination may be made as to whether the excision site 70 is sufficiently deep enough to accommodate the implant that may eventually be placed within the excision 70. As may be appreciated, if the excision site 70 is not sufficient deep, or properly formed, the impact guide 120 may be removed from the excision site 70 and the guide pin 56. The excision device 10 may again be placed over the guide pin 56 and further excision may be provided to deepen or further form the excision site 70. This procedure of checking the excision site 70 using the impact guide head 124 may be repeated until it is determined that an implant will fit within the excision site 70. In some embodiments, the use of the impact guide 120 may be to prevent the implant from being too proud in the excision site and from rising above the articular surface 54. In other embodiments, the impact guide head 124 and/or the impact guide 120, may be interchanged with one or more impact guide heads and/or impact guides to determine which implant may better fit or accommodate the excision site in terms of the implant radius or height. Accordingly, one or more impact guide heads 124 may be provided. In some embodiments, the impact guide heads 124 may be interchangeable and removable from the impact guide 120. In other embodiments, a number of impact guides 120 may be provided including different sized impact guide heads 124 fixed to the impact guide 120.

Figure 20:
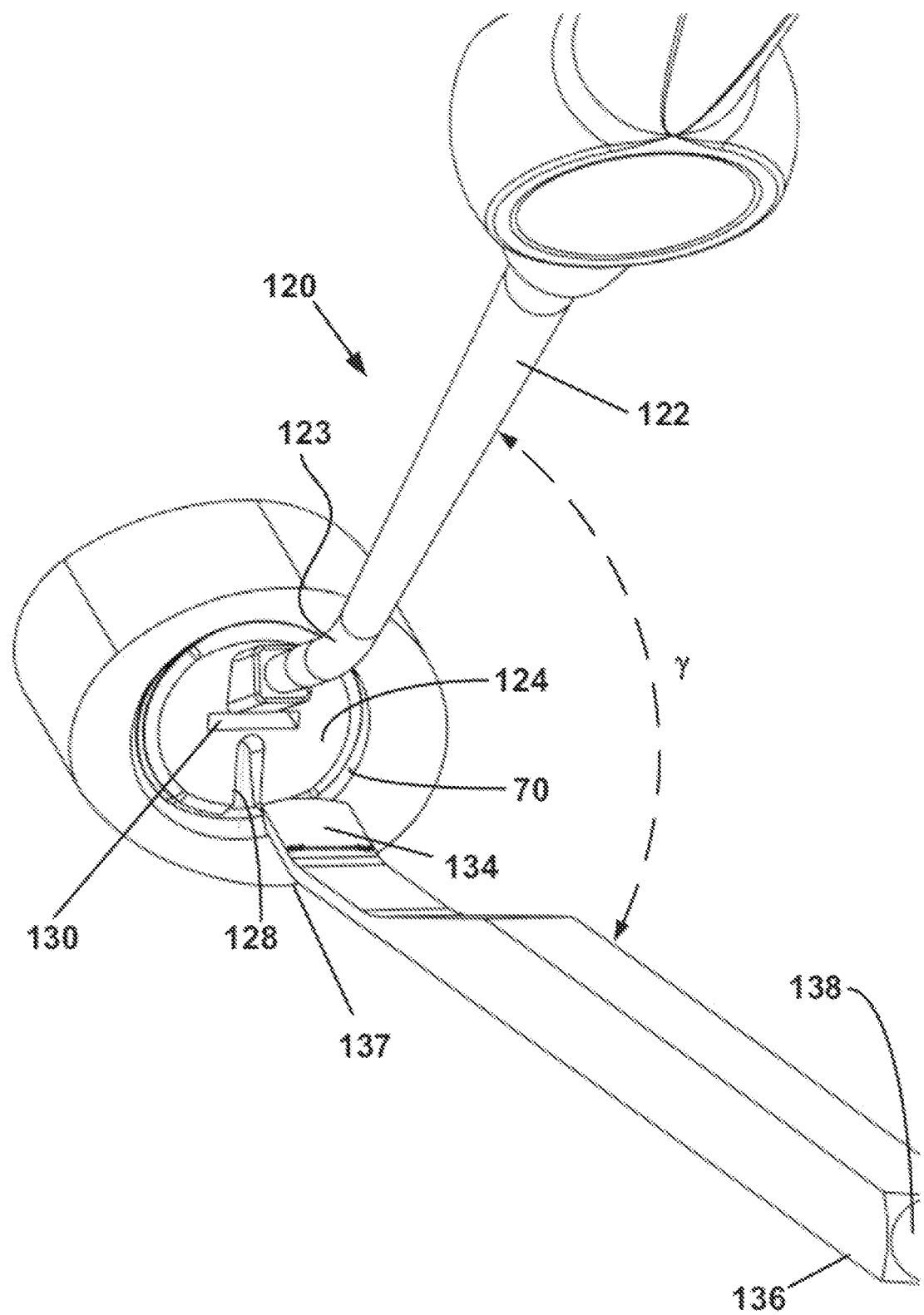
FIG. 20 illustrates a perspective view of an example of an impact guide positioned in an excision site and an impact device.
Figure 21:
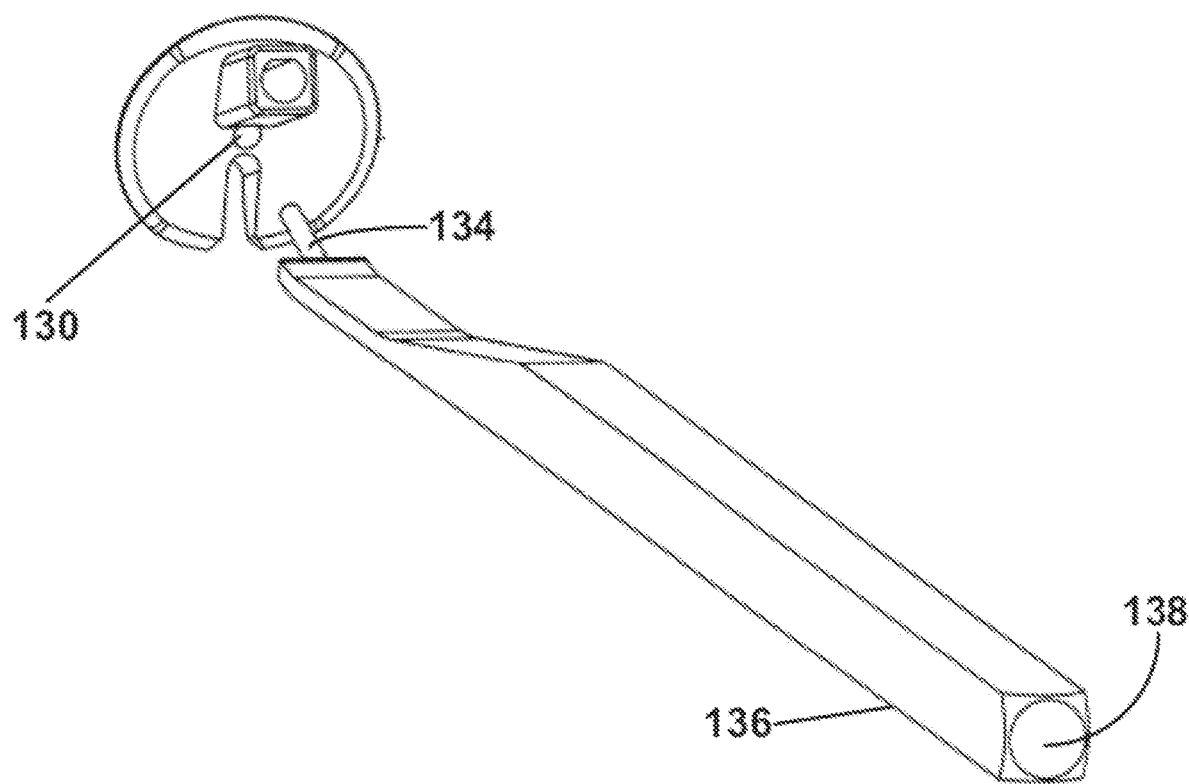
FIG. 21 illustrates a perspective view of another embodiment of an impact guide and an impact device.

Once an impact guide has been selected based on, for example, the size of the excision site, the impact guide head 124 may be seated in the excision site 70 as illustrated in the embodiment of FIG. 20. In one embodiment, the guide pin 56 may optionally be removed before or after seating the selected impact guide head 124. The impact guide head 124 may include an impact slot 130 defined therein. As illustrated in FIG. 20, the impact slot 130 is generally rectangular in cross-section; however, as may be appreciated, other cross-sectional geometries may be provided, such as circular, as illustrated in FIG. 21, as well as elliptical shaped, square shaped, etc. An impact device 132, such as a chisel, punch or awl may be provided, the distal end 134 of which may fit in and extend through the impact slot 130. Therefore, in some embodiments, the distal end may be longer than the length of the impact slot. In addition, the distal end of the impact device 132 may exhibit a cross-sectional area that may be slightly smaller than that of the impact slot 130. The proximal end 136 of the impact device 132 may provide a striking surface 138, which may be hit by hand, or with a hammer or other device, causing the impact device 132 to extend through the impact slot 130 creating a secondary excision site 140 in the primary or first excision site 70. In some embodiments, the impact device may include a sagittal saw or other cutting device, which may be inserted through the impact slot 130. If the guide pin 56 has not yet been removed, it may be removed at this time.

While the proximal end 136 of the impact device 132 is illustrated in FIG. 20 as being provided at an angle γ to the arm 122 of the impact guide 120, wherein angle γ may be in the range of 15 degrees to 120 degrees, including all values and increments therein, in some embodiments, the impact device 132 may be inserted closer to the impact guide 120, wherein angle γ may be in the range of 0 degrees to 45 degrees, including all values and increments therein. In other embodiments, the proximal portion 136 of the impact device may be generally parallel to the arm 122 of the impact guide 120. In such a manner, the impact device 132 may be inserted into incision 49 in the patient (FIG. 6) without the need for expanding the size of the incision 49 greater than necessary to accommodate the head of the excision guide or the head of the impact guide. Further, the impact device 132 may include a curvature 137, which may generally fit over the curvature 123 of the arm 122 of the impact guide 120.

Figure 22:
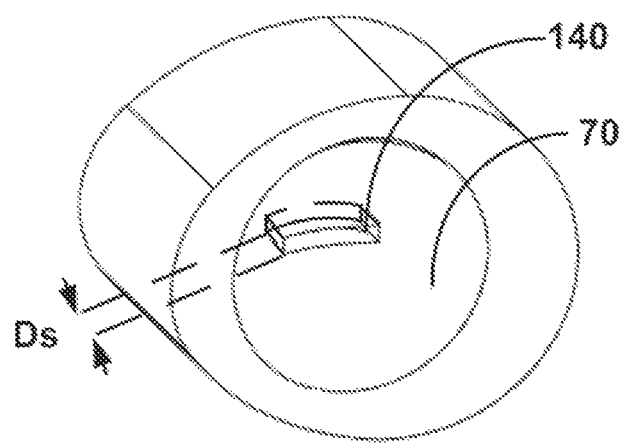
FIG. 22 illustrates a perspective view of an example of a secondary excision site provided in the bottom of a first or primary excision site.
Figure 23:
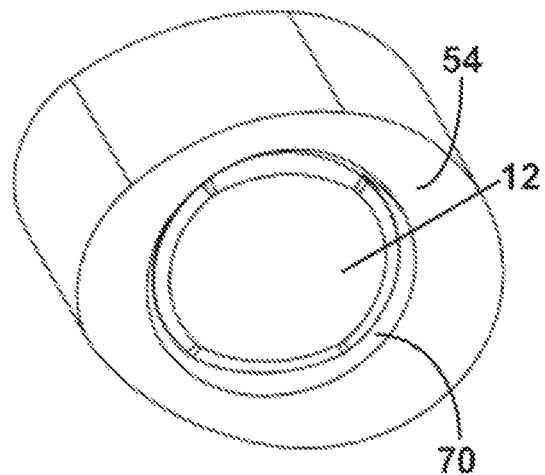
FIG. 23 illustrates an example of a perspective view of an implant positioned in an excision site.

FIG. 22 illustrates an embodiment of a secondary excision site 140 provided in an excision site 70 and FIG. 23 illustrates one embodiment of an implant 12 received in an excision site 70. The secondary excision site 140 is illustrated as being generally rectangular; other cross-sectional geometries may be provided as well. In addition, the depth $D_s$ of the secondary excision site (illustrated in broken lines) may be formed to generally correspond with protrusions 34, 42, 44a-d that may extend from the keel 32 of the bone facing surface of the implant 12, illustrated in the embodiments of FIGS. 4 and 5a-f.

While the implant 12 may be held in place in some examples through a mechanical fit, such as through an interference fit bone adhesive may be used to secure the implant 12 in place in other embodiments. In such a manner a layer of bone adhesive may be delivered to the excision site 70, and optionally to the secondary excision site 140 and the implant 12 may be situated over the adhesive and positioned within the excision site.

Turning to FIGS. 24-30, another apparatus, system, and/or method for resurfacing at least a portion of an articular surface 54 having a defect 52 by replacing a portion of the articular surface 54 with an implant 12, as well as for locating an implant 12, consistent with the present disclosure, is generally illustrated. Again, the description of the apparatuses, systems and methods herein are not limited to the treatment of any single articular surface 54 of the glenoid 58, and may apply, not only to the one or more articular surfaces 54 that may be present in the glenoid 58, but to other articular surfaces through out the human body as well. Stated another way, the present disclosure describes apparatuses, systems, and/or methods for replacing a portion of the articular surface 54 of the glenoid 58, however, it should be understood that the apparatuses, systems, and/or methods according to the present disclosure may also be used to resurface articular surfaces other than the glenoid 58.

Similar to the previous embodiment, one or more incisions 49 may be created proximate to the patient's shoulder 50 to provide access to one or more defect sites 52 on articular surface 54 of the glenoid 58, using, for example, a scalpel or the like with an anterior approach. Thereafter, a portion of an excision guide 102 may be positioned within the incision and located between the humerus 62 and the articular surface 54 of the glenoid 58.

Figure 24:
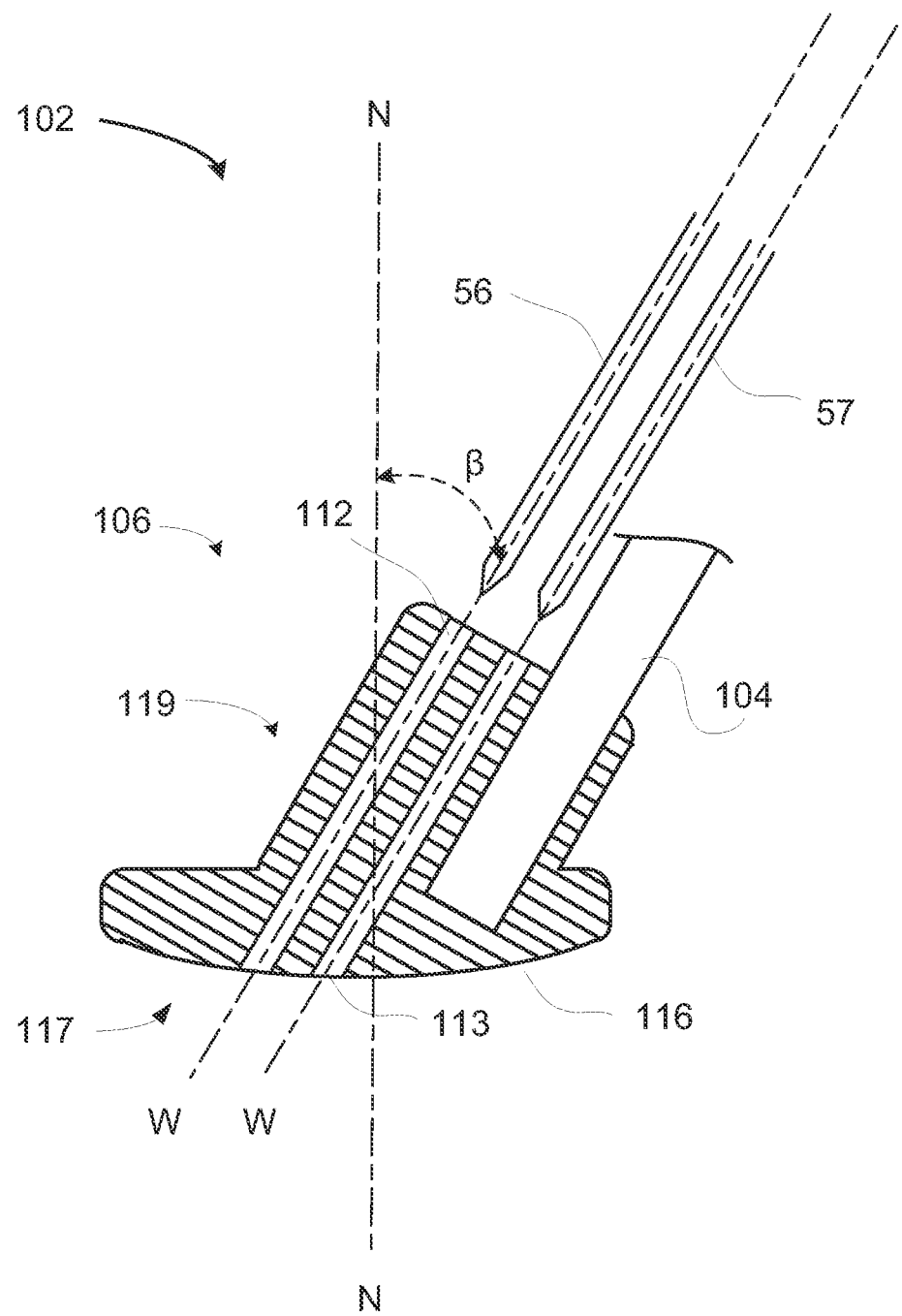
FIG. 24 illustrates a cross-sectional view of the side view of another example of an excision guide having a plurality of guide pins to be positioned therethrough.

According to one embodiment, any one of the excision guides 102 described herein may be used to establish at least one (e.g., a first) guide pin 56 extending from the articular surface 54 at angle β. Referring now to FIG. 24, yet another embodiment of an excision guide 102 is generally illustrated. The excision guide 102 of FIG. 24 may be similar to the previous embodiments described herein and may include an arm 104 and a head 106, which may, in some embodiments, be inserted through the incision 49 in such a manner to avoid contact with the humerus 62. One or more contact surfaces 116 located on the lower portion 117 of the excision guide head 106 may generally conform to the articular surface 54 (see FIG. 14B.). In other embodiments, the contact surface 116 may be a ring or partial ring (e.g., one or more arcuate regions) near the periphery of the lower portion 117 of the excision guide head 106. As may be appreciated in some embodiments, when in the shape of a ring, the contact surface 116 may be continuous or may, in other embodiments, be discontinuous forming ridges around the contact surface 116 (see FIG. 14C). The excision guide 102 may also include a handle 108 (seem for example, a handle as generally illustrated in FIG. 14A) to assist in manipulation and/or stabilization of the excision guide 102. The handle 108 may be affixed to the upper portion of the excision guide head 119.

The head 106 of the excision guide 102 may be positioned in overlying relationship onto the articular surface 54, which may or may not be located over the defect site 52 of the articular surface. For example, in some embodiments, the head 106 may be generally centered in the concavity 55 (glenoid cavity) of the articular surface 54, including the defect 52. However, in other embodiments, the head 106 may be located generally centered in the concavity 55 (glenoid cavity) of the articular surface 54, but not over the defect site 52, which may be located on the glenoid rim.

The head 106 may locate the excision guide 102 relative to the articular surface 54. Once the head 106 suitably positioned, at least one cylindrical guide pin 56 may be received into and pass through a cylindrical guide pin sleeve 112 disposed on the head 106 as generally described herein. As illustrated in FIG. 24, the guide pin sleeve 112 may define an opening from the upper surface 119 of the excision guide head 106 through the lower surface 117 of the excision guide head 106. The guide pin sleeve 112 may position the guide pin 56 relative to the defect 52 on the articular surface. In addition, the guide pin sleeve 112 may be formed in and/or integral to the head 106 or may be formed in an insert connected to the head 106.

As with the previous embodiment (e.g. see FIG. 16 and FIG. 17), the guide pin sleeve 112 of the excision guide 102 may orient the working axis (W) of the guide pin 56 at an angle β relative to a normal axis (N). The working axis (W) may be defined by the guide pin sleeve 112 to an axis (N) generally central and normal to the lowest point of the contact surface 116 of the excision guide head 106. Angle β may be 90 degrees or less and in some examples, including all values and increments in the range of 5 degrees and 80 degrees, such as in the range of 10 degrees to 30 degrees.

The guide pin sleeve 112 may also offset the intended entry point of the guide pin 56 in the articular surface 54 radially outward from the normal axis (N). The offset (O) may be determined based on the angle β of entry of the guide pin 56 into the articular surface 54 and/or the depth of the desired excision site, or the height of the desired implant. For example, the offset (O) may be proportional to the angle β of the guide pin 56 to the normal axis (N).

The working axis (W) may be positioned at an angle β in the range of 10 degrees to 90 degrees, such as in one embodiment, 15 degrees to 45 degrees, or in a further embodiment 60 degrees from the normal axis (N). As may be appreciated, in some embodiments, the contact surface(s) 116 of the excision guide head 106 may exhibit some degree of curvature and may be convex. The curvature of the contact surface 116 of the excision guide head 106 may be configured to generally match the curvature of at least a portion of the articular surface 54. In some embodiments, it may be appreciated, that the curvature of the articular surface 54 and the contact surface 116 of the excision guide head 106 may not match exactly but may provide a "close fit" sufficient to locate the excision guide head 106 within the glenoid 58. In some non-limiting embodiments, the curvature of the contact surface 116 may be generally hemispherical, including pyriform or teardrop in shape.

As may be appreciated, any of the excision guides 102 described herein may be used to establish the first guide pin 56 at the angle θ. Once the first guide pin 56 is established, at least a second guide pin 57 may also be secured extending from the articular surface 54.

According to one embodiment, the excision guide 102 of FIG. 24 may also be used to establish the second or more guide pins 57, or, alternatively as disclosed below, the guide body 204 disclosed herein may be used to establish the second or more guide pins 57.

For example, once the first guide pin 56 is positioned in the articular surface 54 of the glenoid 58, the second (or more) cylindrical guide pin 57 may be received into and pass through a cylindrical guide pin sleeve 113 disposed on the head 106. As illustrated in FIG. 24, the guide pin sleeve 113 may define an opening from the upper surface 119 of the excision guide head 106 through the lower surface 117 of the excision guide head 106. The guide pin sleeve 113 may position the guide pin 57 relative to the defect 52 on the articular surface. In addition, the guide pin sleeve 113 may be formed in and/or integral to the head 106 or may be formed in an insert connected to the head 106.

As shown, guide pin sleeve 113 is substantially parallel to guide pin sleeve 112 such that guide pin 57 will be substantially parallel to guide pin 56 (e.g. within plus or minus 5 degrees). It may be appreciated, however, that the second guide pin 57 may also be non-parallel relative to first guide pin 56, or any other guide pin (not shown) secured to the articular surface 54. Also, while second guide pin 57 is shown to have a length substantially equal to the length of first guide pin 56, the second guide pin 57 may be shorter than first guide pin 56.

Once the guide pin 56, and in certain embodiments guide pin 57, are positioned in the articular surface 54 of the glenoid 58, the excision guide 102 may be removed from the glenoid 58 by sliding the excision guide 102 up the guide pin 56, and in certain embodiments guide pin 57, away from the glenoid 58. Once excision guide 102 is removed, an excision apparatus 200 may be installed thereon.

As shown in FIGS. 25-28, excision apparatus 200 may comprise an elongated guide body 204, for example, having a generally T-shaped cross-sectional profile. Guide body 204 has a proximal end 206 and a distal end 208, and comprises a plurality of cylindrical guide pin sleeves 210, 212, 214 and 216 configured to contain/receive guide pins 56 and 57. As shown, cylindrical guide pin sleeves 210, 212, 214 and 216 have a diameter substantially equal to guide pins 56 and 57 (e.g. greater in diameter by less than or equal to 0.04 inches, and more particularly by less than or equal to 0.02 inches). Also as shown, the guide pin sleeves 210, 212, 214 and 216 are substantially parallel (e.g. within plus or minus 10 degrees, and more particularly within plus or minus 5 degrees)

Guide body 204 also includes an excision device sleeve 220 to receive/contain an excision device 240. Excision device 240 may comprises a shaft 244 and a cutting head 250 located at a distal end of the shaft 244. As such, it may be understood that excision device sleeve 220 holds shaft 244. As shown, cutting head 250 is a reamer and more particularly a hemispherical (acorn) reamer.

As shown, excision device sleeve 220 terminates proximal to any of guide pin sleeves 210, 212, 214, or 216. In such manner, the distal end 208 of the guide body 204 may be stepped with a raised shoulder portion 209a which provides a contact face/surface (to contact articular surface 54) 208a. Distal end 208 further comprises a recessed face/surface (non-contact) 208b, and a recess/pocket 209b adjacent the shoulder 209a to contain the cutting head 250 with the distal end thereof proximal to distal end contact surface 208a.

The proximal end of guide body 204, and more particularly, the entrance to excision device sleeve 220 may be stepped with a notch 230 which may allow a clinician using excision apparatus 200, to use one or more cylindrical scribe markings or indicia (e.g., laser markings) 248 formed on shaft 244 to determine cutting depth. For example, first excision apparatus 200 may be first arranged such the cutting head 250 is in contact with recessed surface 208b and indicia 248 is proximal to the top of the notch 230 defined by proximal end surface 206a. Then as shaft 244 and cutting head are moved distally, cutting head 250 may come into contact with the articular surface, for example, when indicia 248 is parallel with proximal end surface 206a. Thereafter, a clinician may move excision device 240 distally until indicia 248 becomes parallel with proximal end surface 206b at the bottom of the notch 230, at which time the clinician may be informed that the desired cutting depth has been achieved.

Figure 25:
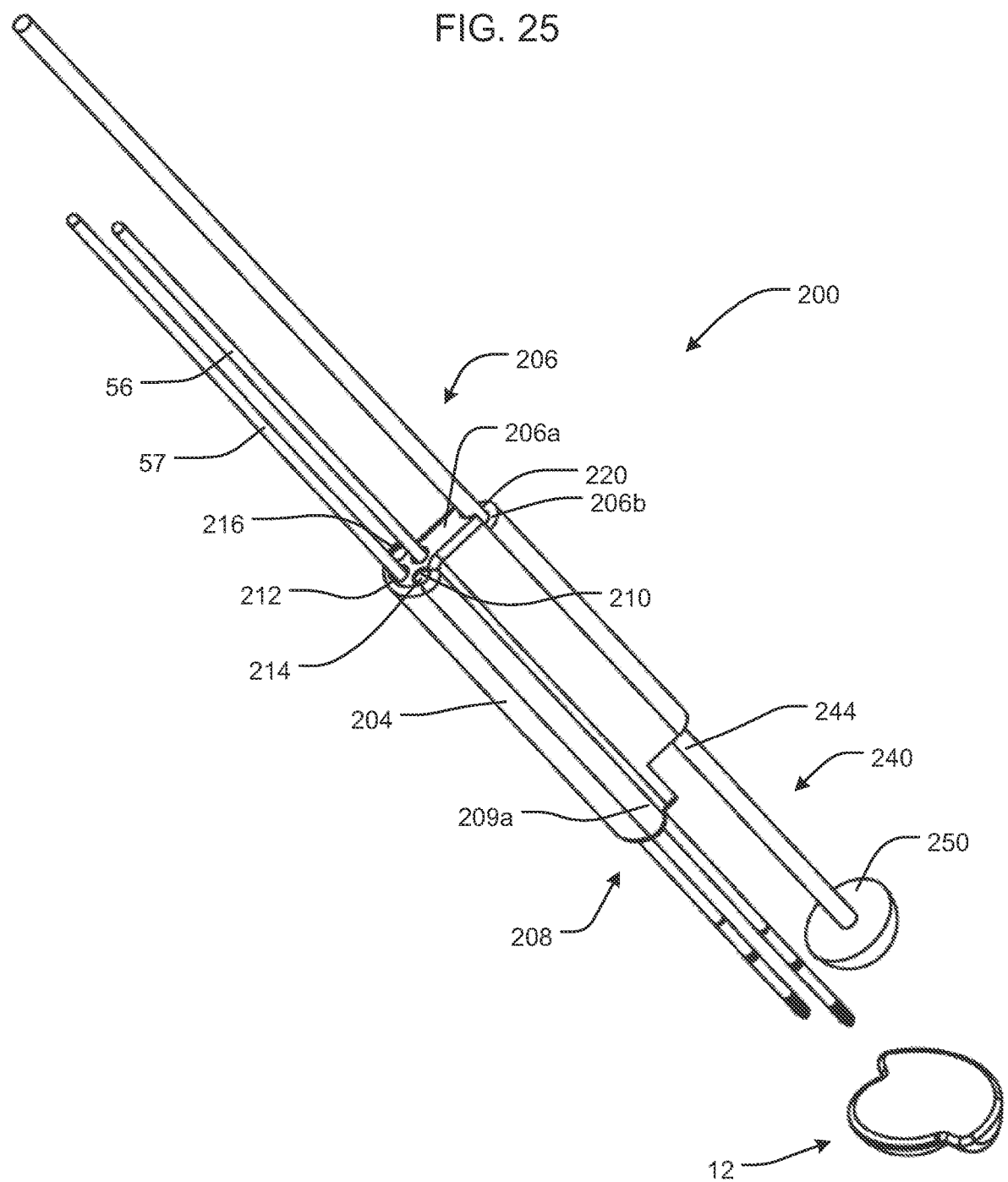
FIG. 25 illustrates a perspective view of excision apparatus comprising a guide body and an excision device, and an implant.

As best shown in FIG. 25, excision apparatus 200 is first assembled with shaft 244 of excision device positioned within excision device sleeve 220 of guide body 204. Thereafter, the excision apparatus 200 is installed on guide pins 56 and 57, particularly by locating guide pin 56 in guide pin sleeve 210 and guide pin 57 in any of guide pin sleeves 212, 214 or 216, and sliding guide body 204 distally down the length of guide pins 56 and 57. Alternatively, as set forth above, guide body 204 may be slid distally down the length of only guide pin 56, and the position of second guide pin 57 may then be established in the articular surface 54 using the guide body 204.

Figure 28A:
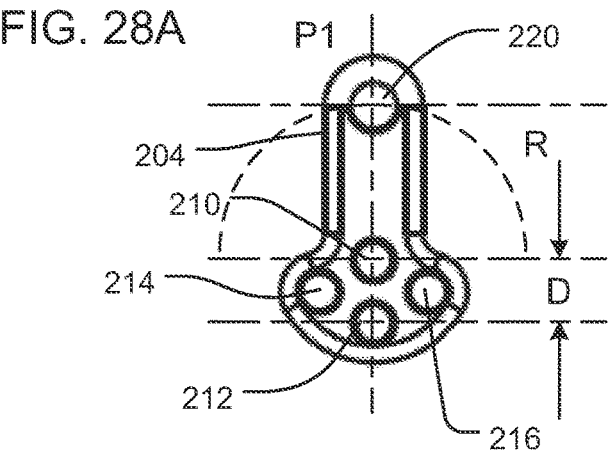
FIG. 28A illustrates a proximal end view of the guide body of the excision apparatus of FIG. 25 in a first excision position.
Figure 28B:
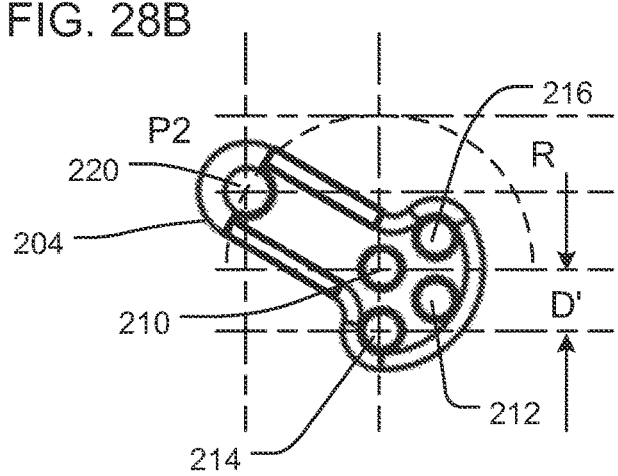
FIG. 28B illustrates a proximal end view of the guide body of the excision apparatus of FIG. 25 in a second excision position.
Figure 28C:
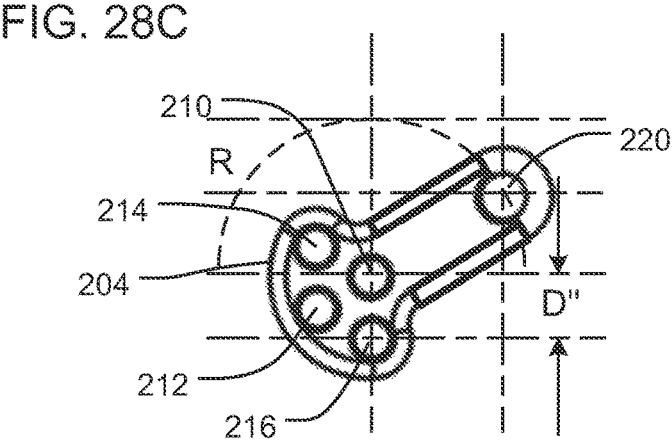
FIG. 28C illustrates a proximal end view of the guide body of the excision apparatus of FIG. 25 in a third excision position.
Figure 27:
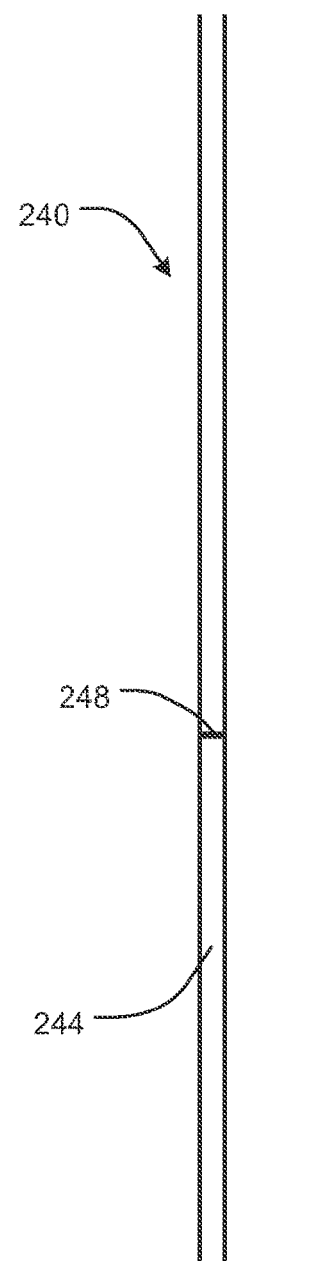
FIG. 27 illustrates a side view of the excision device of the excision apparatus of FIG. 25.

As shown in FIGS. 28A-28C, the center-to-center distance D between the center longitudinal axis of guide pin sleeve 210 and the center longitudinal axis of guide pin sleeve 212 (FIG. 28A), which is substantially equal (e.g. within 0.02 inch, and more particularly within 0.01 inch) to the center-to-center distance between the center longitudinal axis of guide pin 56 and the center longitudinal axis of guide pin 57, is substantially equal (e.g. within 0.02 inch, and more particularly within 0.01 inch) to the center-to-center distance D' between the center longitudinal axis of guide pin sleeve 210 and the center longitudinal axis of guide pin sleeve 214 (FIG. 28B), as well as the center-to-center distance D" between the center longitudinal axis of guide pin sleeve 210 and the center longitudinal axis of guide pin sleeve 216 (FIG. 28C).

During use of excision apparatus 200, guide pin sleeve 210 of guide body 204 may be rotated (e.g., indexed) on guide pin 56, which may be used as a pivot to rotate a position of the cutting head 250 of excision device 240 along radius R with respect to the articular surface 54. For example, a first excision site (e.g., first planetary excision site) may be formed in articular surface 54 in a first excision position P1 when guide pin 56 is positioned in guide pin sleeve 210 and guide pin 57 is positioned in guide pin sleeve 212 (as shown by FIG. 28A) to retain (lock) the guide body 204 against rotation.

Thereafter, guide body 204 may then be slid proximally upward on guide pins 56 and 57 until guide body 204 clears guide pin 57 (in the case where guide pin 57 is shorter than guide pin 56). After guide pin 57 is cleared, guide body 204 may be rotated counterclockwise on guide pin 56 to a second excision position P2 such that guide pin sleeve 214 is aligned axially with guide pin 57 (as shown by FIG. 28B), which retains the guide body 204 in fixed position against rotation, at which point guide body 204 may be slid distally downward with guide pins 56 and 57 in guide pin sleeves 210, 214, respectively, to form a second excision site (e.g., second planetary excision site) corresponding to the second excision position P2.

Thereafter, guide body 204 may then be slid proximally upward on guide pins 56 and 57 until guide body 204 clears guide pin 57 once again. After guide pin 57 is cleared, guide body 204 may be rotated clockwise on guide pin 56 to a third excision position P3 such that guide pin sleeve 216 is aligned axially on guide pin 57 (as shown by FIG. 28C), which retains the guide body 204 in fixed position against rotation, at which point guide body 204 may be slid distally downward with guide pins 56 and 57 in guide pin sleeves 210, 216, respectively, to form a third excision site (e.g., third planetary excision site) corresponding to the third excision position P3.

Alternatively, when guide body 204 is slid proximally on guide pins 56 and 57, guide body 204 may clear both guide pins 56 and 57, and be rotated by hand, without the aid of guide pin sleeve 210 on guide pin 56 as a pivot, from the first excision position P1 to the second excision position P2, and from the second excision position P2 to the third excision position P3. It also should be understood that while the present description describes three excision positions (e.g., corresponding to three planetary excision sites), the excision apparatus 200 (e.g., guide body 204) may be configured to form a plurality of planetary excision sites and that any reasonable number of excision positions may be utilized depending on the number of guide pin sleeves, as well as the radius of the reamer 240 and the length of the articular surface to be replaced. The planetary excision sites may partially overlap with an adjacent planetary excision site. Additionally, the planetary excision sites may be formed in any order, and the above description is merely for illustrative purposes only.

Figure 29A:
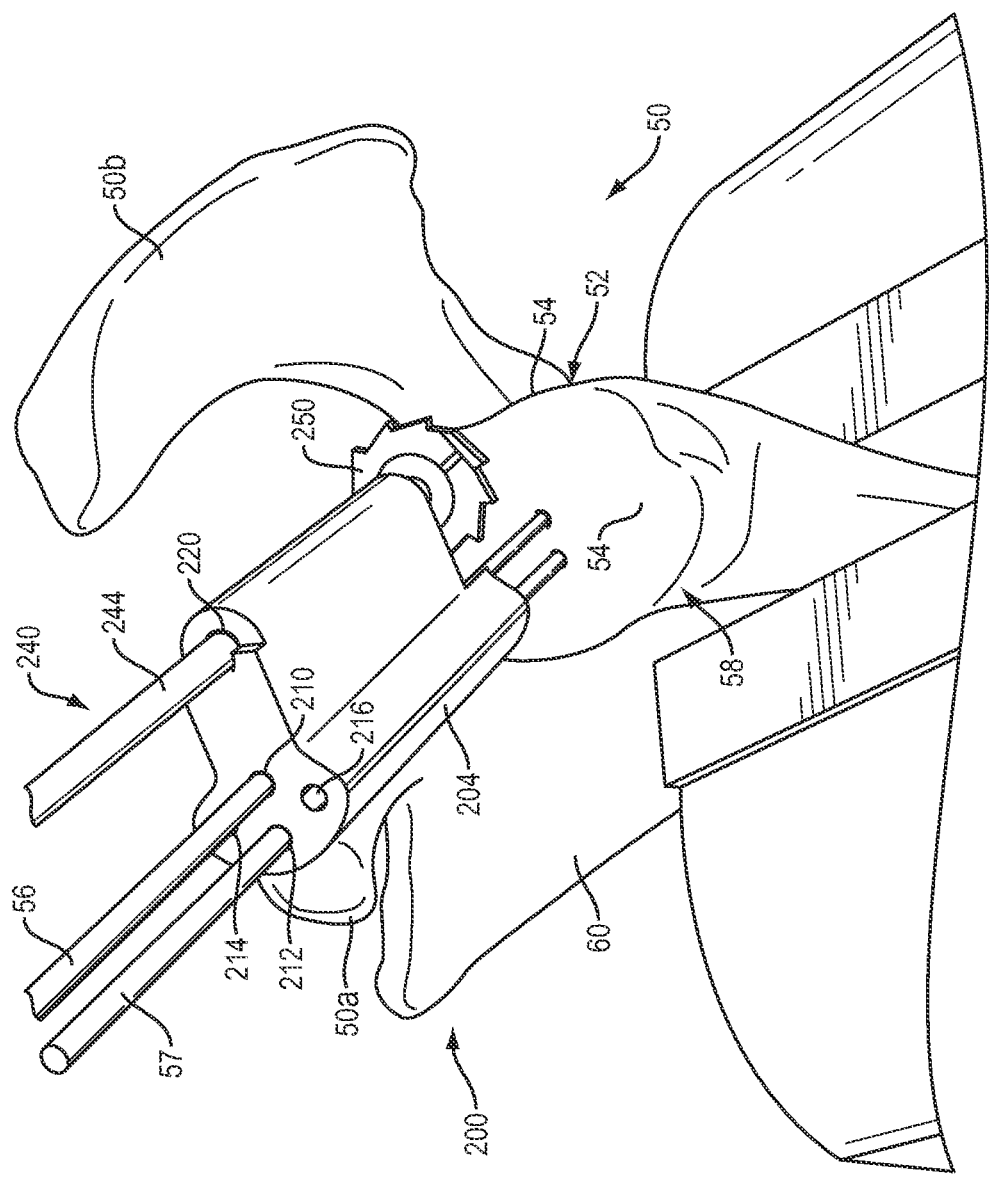
FIG. 29A illustrates a perspective view of the excision apparatus of FIG. 25 positioned overlying a glenoid.

Referring now to FIGS. 29A-29G, in FIG. 29A, guide body 204 is shown in a first excision position P1 with guide pins 56 and 57 within guide pin sleeves 210 and 212, respectively, and cutting head 250 of excision device 240 retracted into recess/pocket 209b of the guide body 204.

As shown, shoulder 50 may be understood to be the left shoulder, particularly given the positioning of the coracoid process 50a and the ancromion 50b. Defect site 52 may comprise a portion of the articular surface 54. As may be appreciated, the glenoid 58 may include one or more articular surfaces 54, which may define a concavity. As such, the defect site 52 may comprise a portion of the articular surface 54 of the glenoid 58, and more particularly the glenoid cavity (glenoid fossa and/or glenoid vault) and the glenoid rim (glenoid labrum).

Figure 29B:
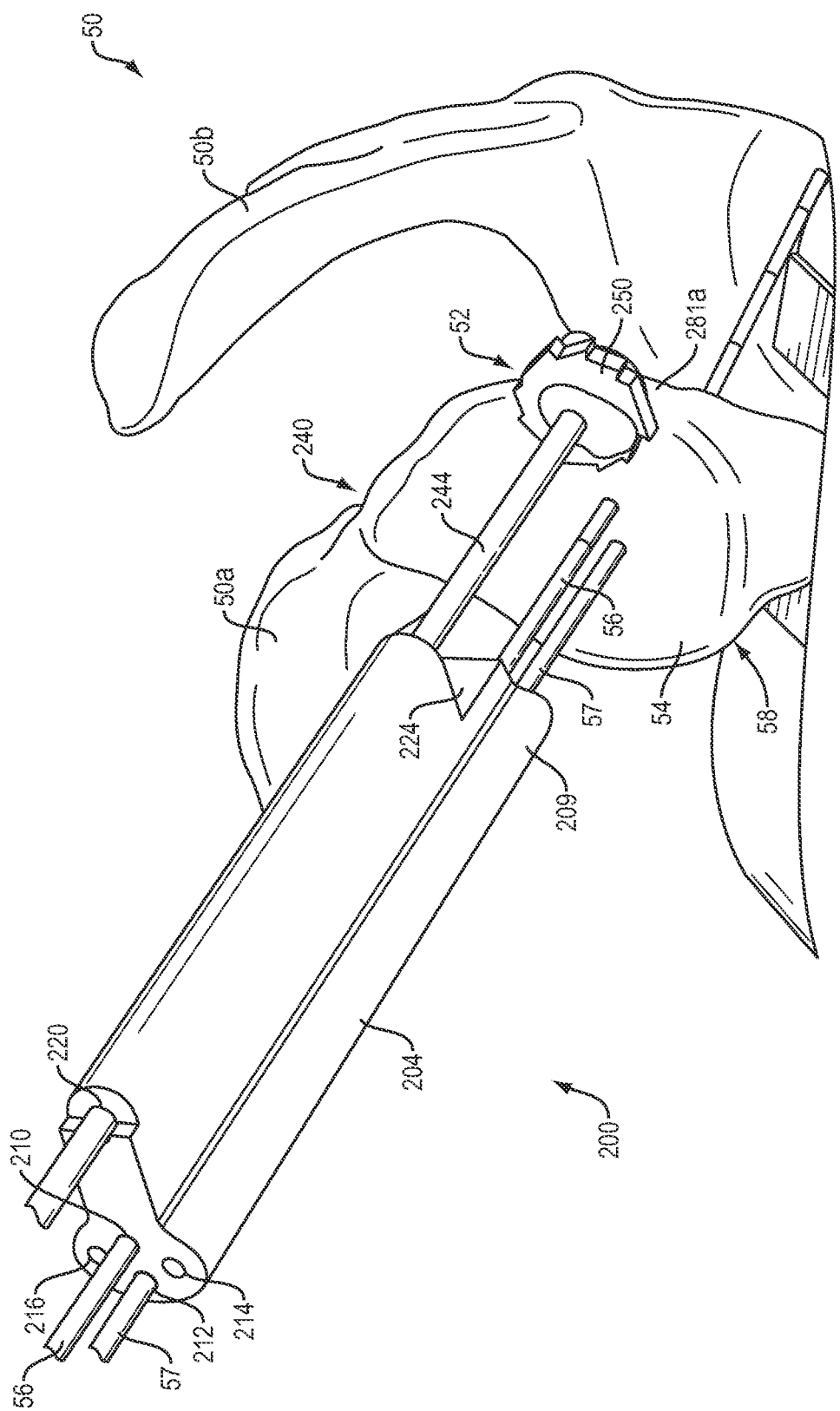
FIG. 29B illustrates a perspective view of the excision apparatus of FIG. 25 with the excision device forming a first excision site created in a glenoid.
Figure 29C:
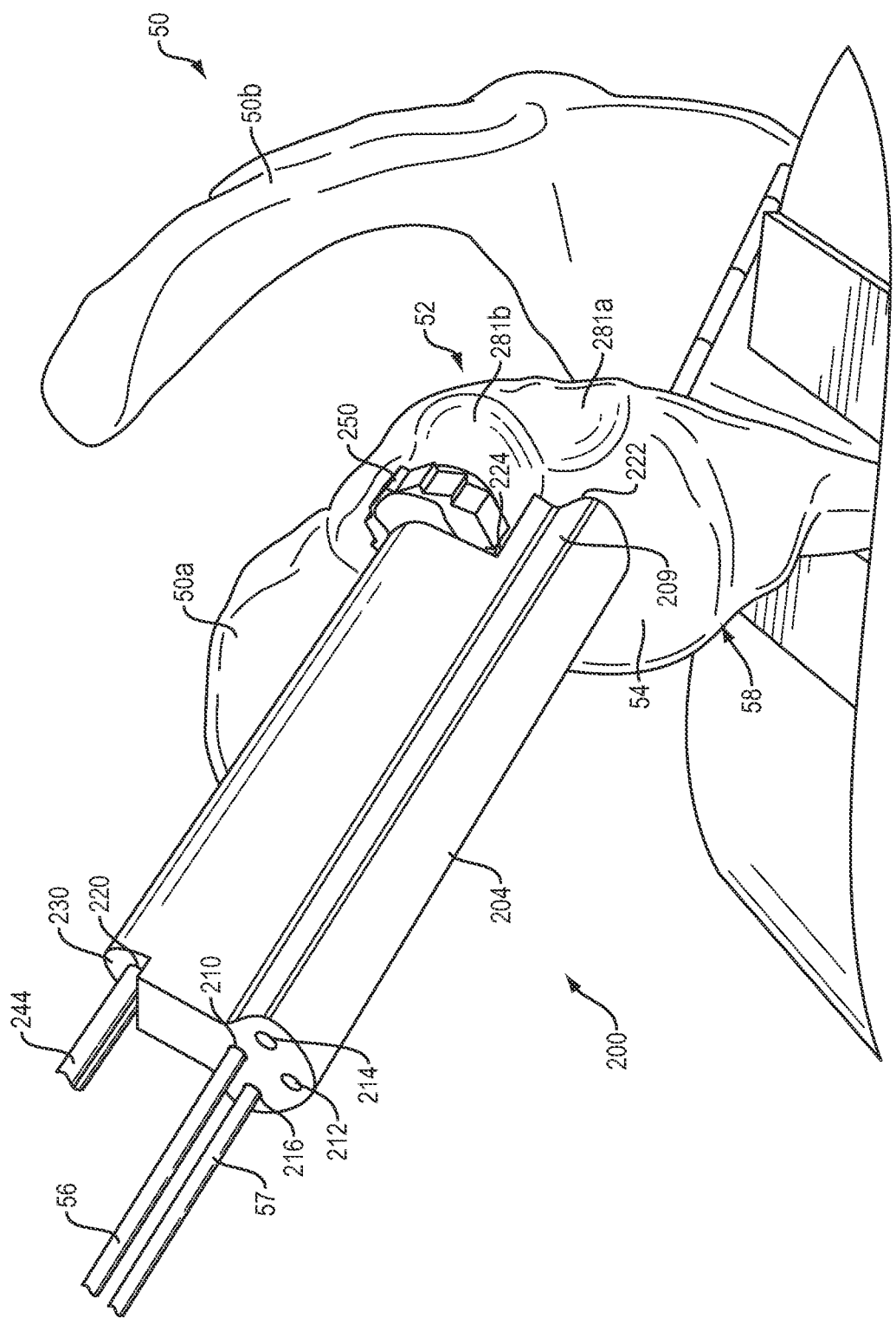
FIG. 29C illustrates a perspective view of the excision apparatus of FIG. 25 with the excision device forming a second excision site created in a glenoid.
Figure 29D:
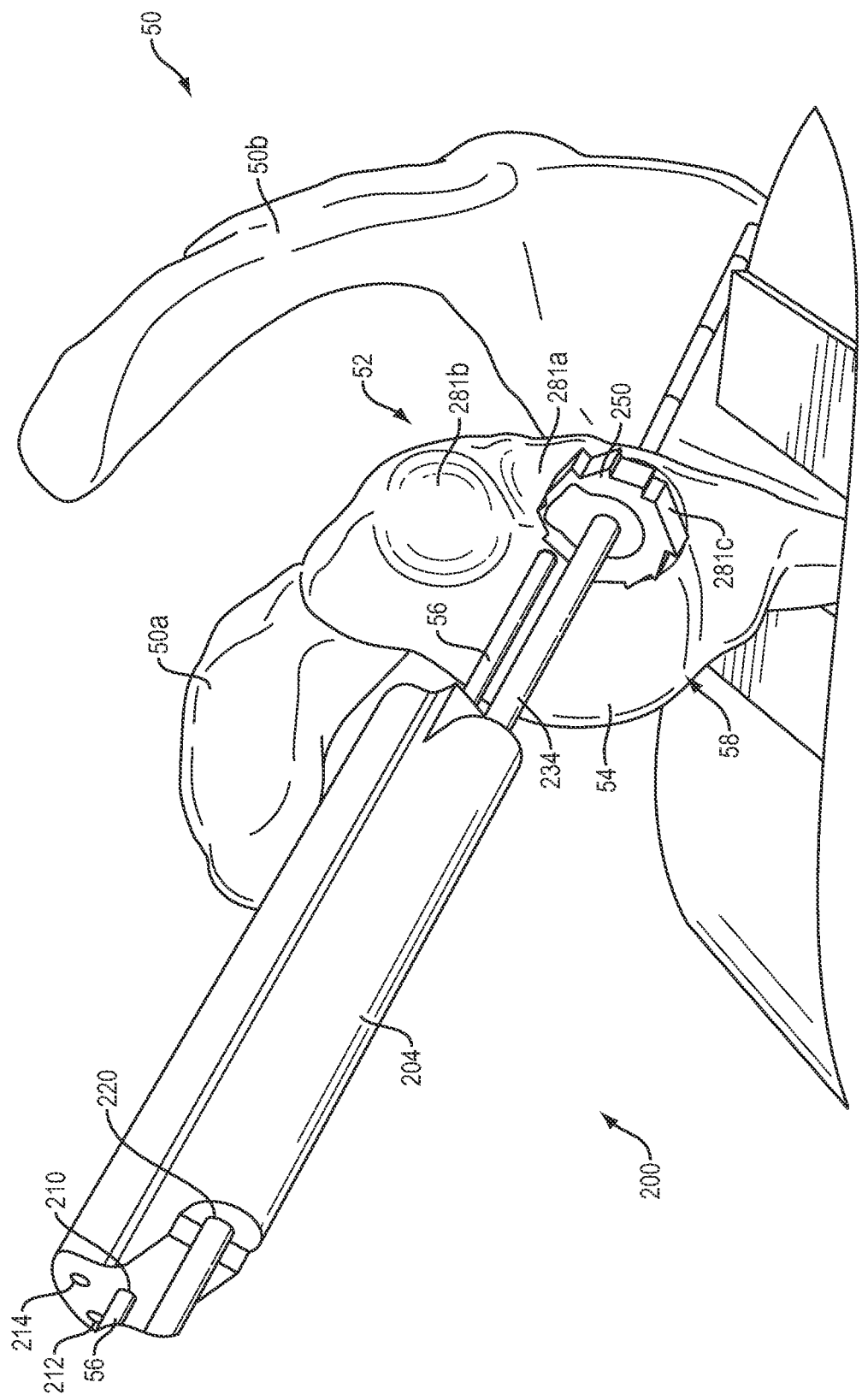
FIG. 29D illustrates a perspective view of the excision apparatus of FIG. 25 with the excision device forming a third excision site created in a glenoid.

In FIG. 29B, cutting head 250 on excision device 240 is extended into contact with articular surface 54 to make a first excision site 281a (e.g., first planetary excision site). Thereafter, as shown in FIG. 29C, after guide body 204 has been positioned such that guide pins 56 and 57 are within guide pin sleeves 210 and 214, respectively, as discussed above, cutting head 250 on excision device 240 is extended into contact with articular surface 54 to make a second excision site 281b (e.g., second planetary excision site). Thereafter, as shown in FIG. 29D, after guide body 204 has been positioned such that guide pins 56 and 57 are within guide pin sleeves 210 and 216, respectively, as discussed above, cutting head 250 on excision device 240 is extended into contact with articular surface 54 to make a third excision site 281c (e.g., third planetary excision site).

Figure 29E:
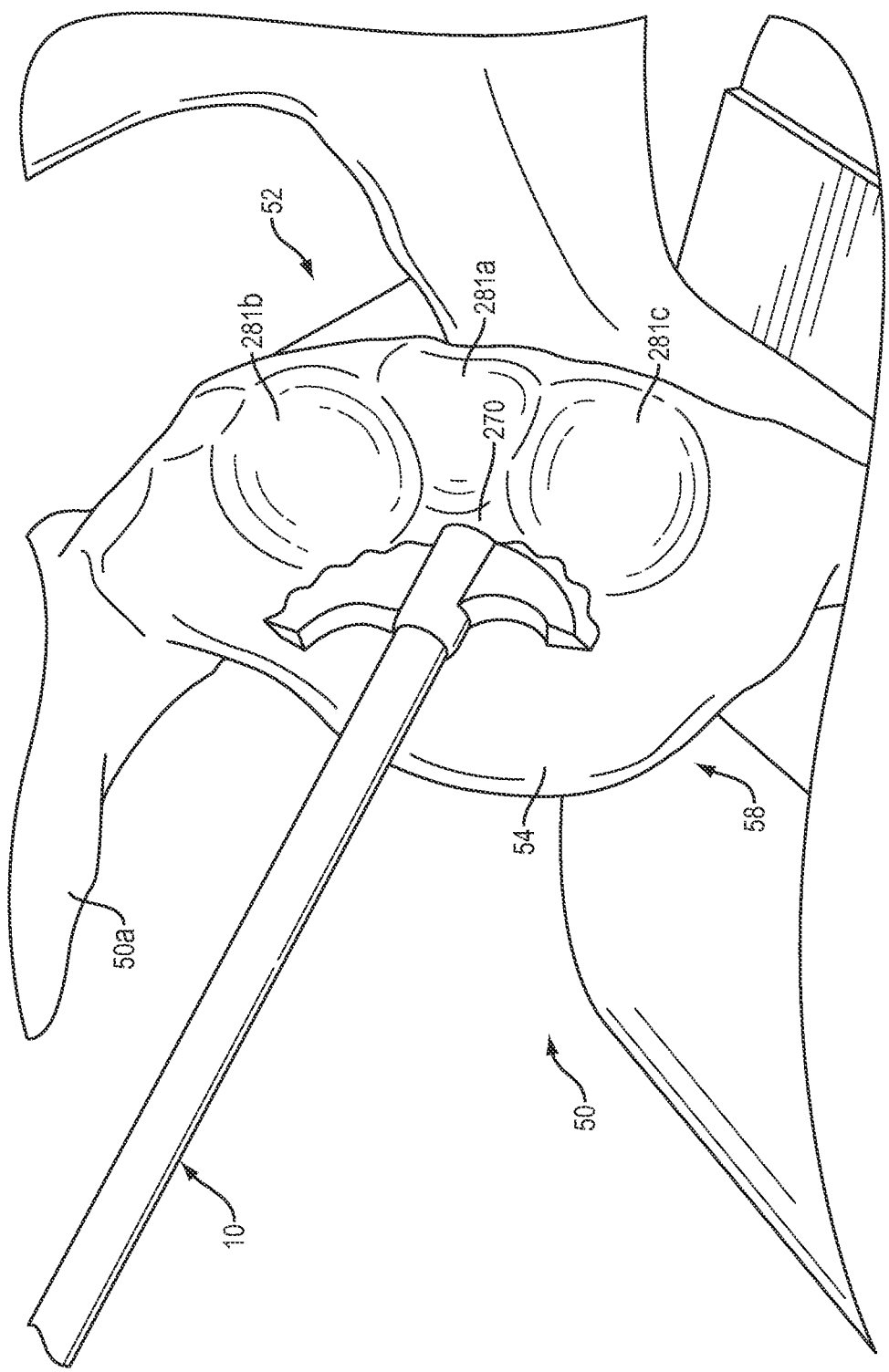
FIG. 29E illustrates a perspective view of an excision device advanced over a guide pin forming a fourth excision site created in a glenoid.

Once planetary excision sites 281a, 281b and 281c are formed, guide body 204, along with excision device 240, may be removed from the surgical site. Similarly, guide pin 57 may also be removed from the surgical site. Thereafter, as shown in FIG. 29E, excision device 10 may be introduced into the surgical site, particularly by passing guide pin 56 through cannulated shaft 14, to form a fourth excision site 270 (e.g., central or vault excision site). Excision device 10 may be used to form the excision site 270 as set forth with the previous embodiment. As may be appreciated, the vault excision site 270 partially overlaps with the plurality of planetary excision sites 281a, 281b, 281c.

Figure 29F:
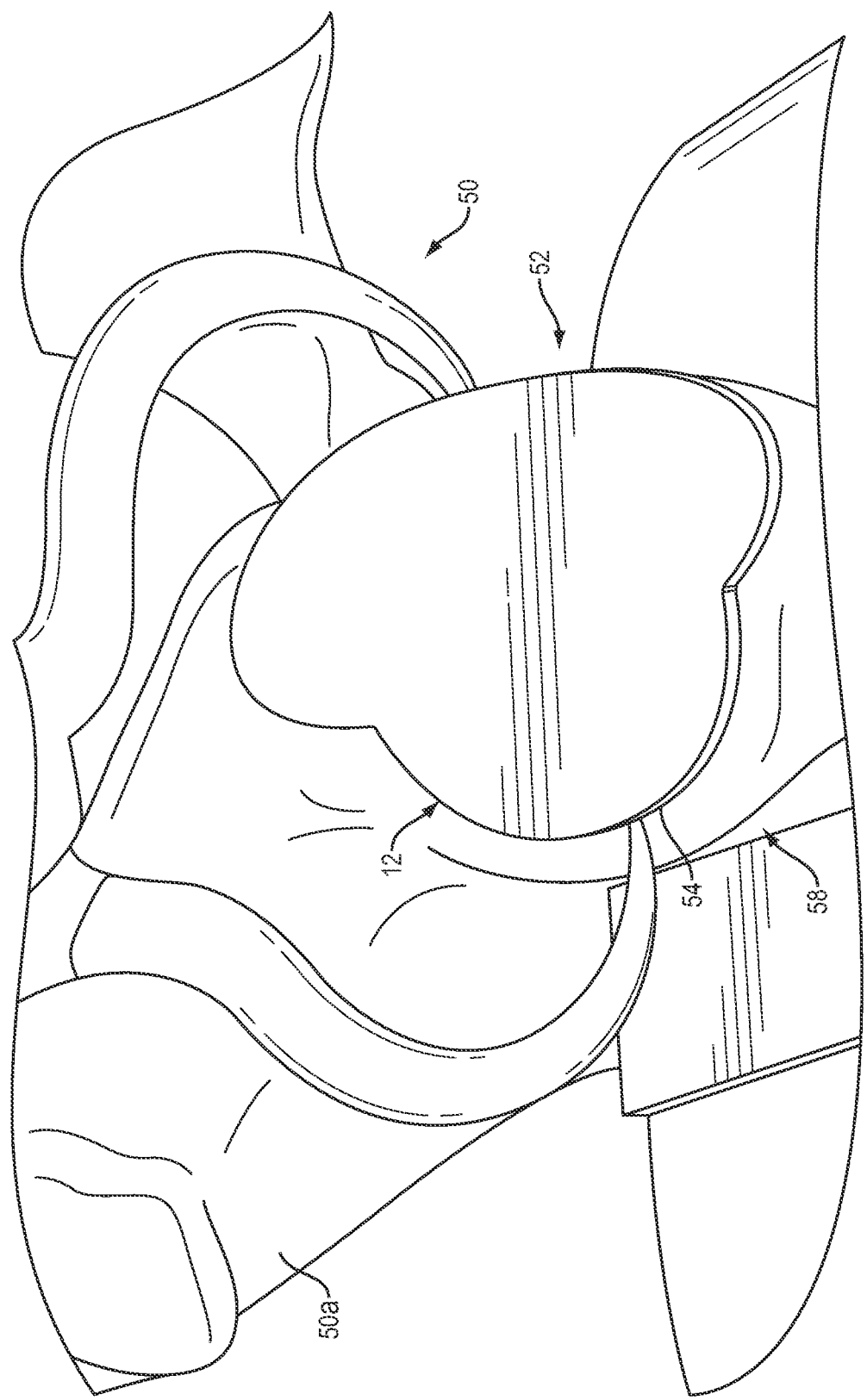
FIG. 29F illustrates an end view of an implant to be implanted in the excision site in the glenoid in FIGS. 29B-29E.
Figure 29G:
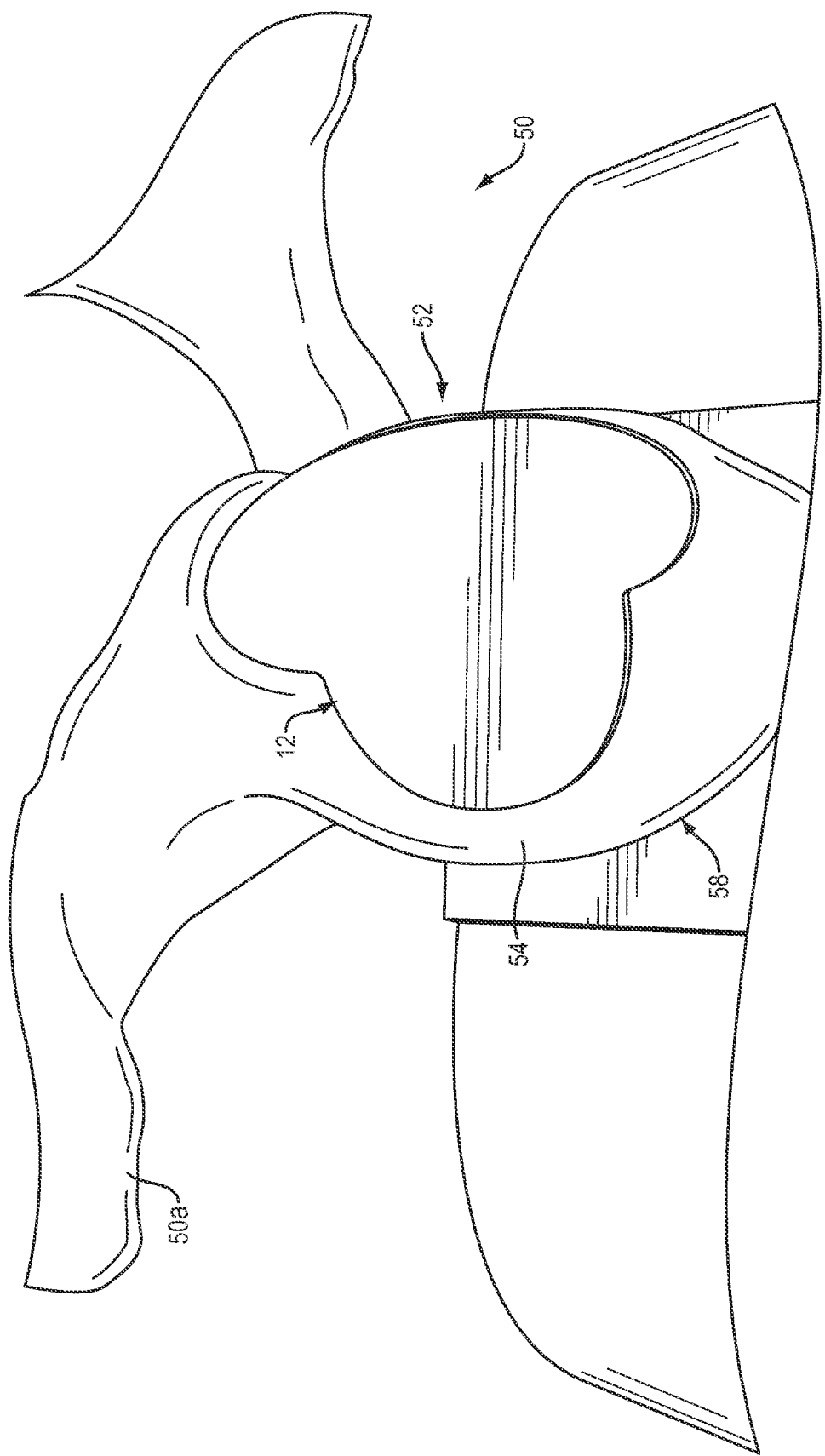
FIG. 29G illustrates an end view of an implant after being implanted in the excision created in a glenoid in FIGS. 29B-29E.

As shown in FIGS. 29F and 29G, with the above excision pattern/arrangement, central hemispherical or vault excision site 270 is located generally in the center of glenoid 52, while one or more of the adjacent hemispherical planetary excision sites 281a-281c surround the periphery of the central hemispherical or vault excision site 270. After forming the planetary excision sites 281a, 281b, 281c and vault excision site 270, implant 12 may be located thereon, and bonded to the glenoid 52, particularly with bone cement as discussed with previous embodiments.

As shown by FIG. 30A, implant 12 may include a load bearing surface 22. The load bearing surface 22 may have a contour substantially corresponding to or based on the contour of the patient's articular surface being replaced. The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior (AP) curvature and the superior-inferior (SI) curvature. One or more of the AP and/or SI curvatures may themselves be based on multiple curves, (for example, as generally described in U.S. patent application Ser. No. 12/027,121, filed Feb. 6, 2008 and entitled SYSTEM AND METHOD FOR JOINT RESURFACE REPAIR, which is fully incorporated herein by reference). The load bearing surface 22 may be generally concaved. For example, the load bearing surface 22 may have a generally hemi-spherical shape.

As shown in FIG. 30A, the load bearing surface 22 may be divided into two regions 22a and 22b. Also as shown, load bearing surface region 22 may comprise a circular glenoid cavity or vault region 22a and a semi-circular glenoid rim or planetary region 22b which surrounds approximately 180 degrees of the periphery of the circular cavity region 22a. However it should be understood that the glenoid cavity region 22a may be surrounded by a glenoid rim region 22b having other sizes. For example, in certain embodiments, the glenoid rim region 22b may surround from 10 degrees to 270 degrees of the glenoid cavity region 22a. In certain other embodiments, the glenoid rim region 22b may surround from 30 degrees to 240 degrees of the glenoid cavity region 22a. In other embodiments, the glenoid rim region 22b may surround from 50 degrees to 210 degrees of the glenoid cavity region 22a. In still other embodiments, the glenoid rim region 22b may surround from 60 degrees to 180 degrees of the glenoid cavity region 22a. In still other embodiments, the glenoid rim region 22b may surround from 80 degrees to 150 degrees of the glenoid cavity region 22a.

As shown in FIGS. 30B-30D, the bone facing surface 24 may be configured to be generally received in the excision formed by planetary excision sites 281a, 281b, 281c and vault excision site 270. As such, the bone facing surface 24 comprises a plurality of hemispherical regions 24a-24d which are configured to substantially match and correspond to the contour of the plurality of hemispherical planetary excision sites 281a, 281b, 281c and vault excision site 270.

For example, the vault region 24d of bone facing surface 24 corresponding to central hemispherical vault excision site 270, which may be in the glenoid cavity region including the glenoid vault region, may have generally hemi-spherical shape substantially corresponding to the contour of the cutting surfaces 20 of the cutters 16a, 16b. Similarly, the planetary regions 24a to 24c of bone facing surface 24 corresponding to hemispherical planetary excision sites 281a to 281c peripheral to the central hemispherical excision site 270, which may be in the glenoid rim region, may have generally hemi-spherical shape substantially corresponding to the contour of the cutting surfaces 250 of the cutting head 250.

The bone facing surface 24 may also include one or more lips, protrusions, ribs, or the like 28a-28n, shown in FIG. 3, configured to increase the mechanical connection between the implant 12 and the patient's bone within the excision site. Again, these lips or the like 28a-28n may generally correspond to the contours of the cutting surfaces 20 of the cutters 16a, 16b. The voids or space 30a-30n between the lips 28a-28n may create pockets for bone in-growth and/or bone cement. Moreover, the implant 12 may optionally include one or more keels or tails 32 extending generally outwardly from the bone facing surface 24 as shown in FIGS. 4 and 5A to 5G. For example, the keel or tail 32 may extend generally outward from the vault region 24d of the bone facing surface 24.

Figure 31A:
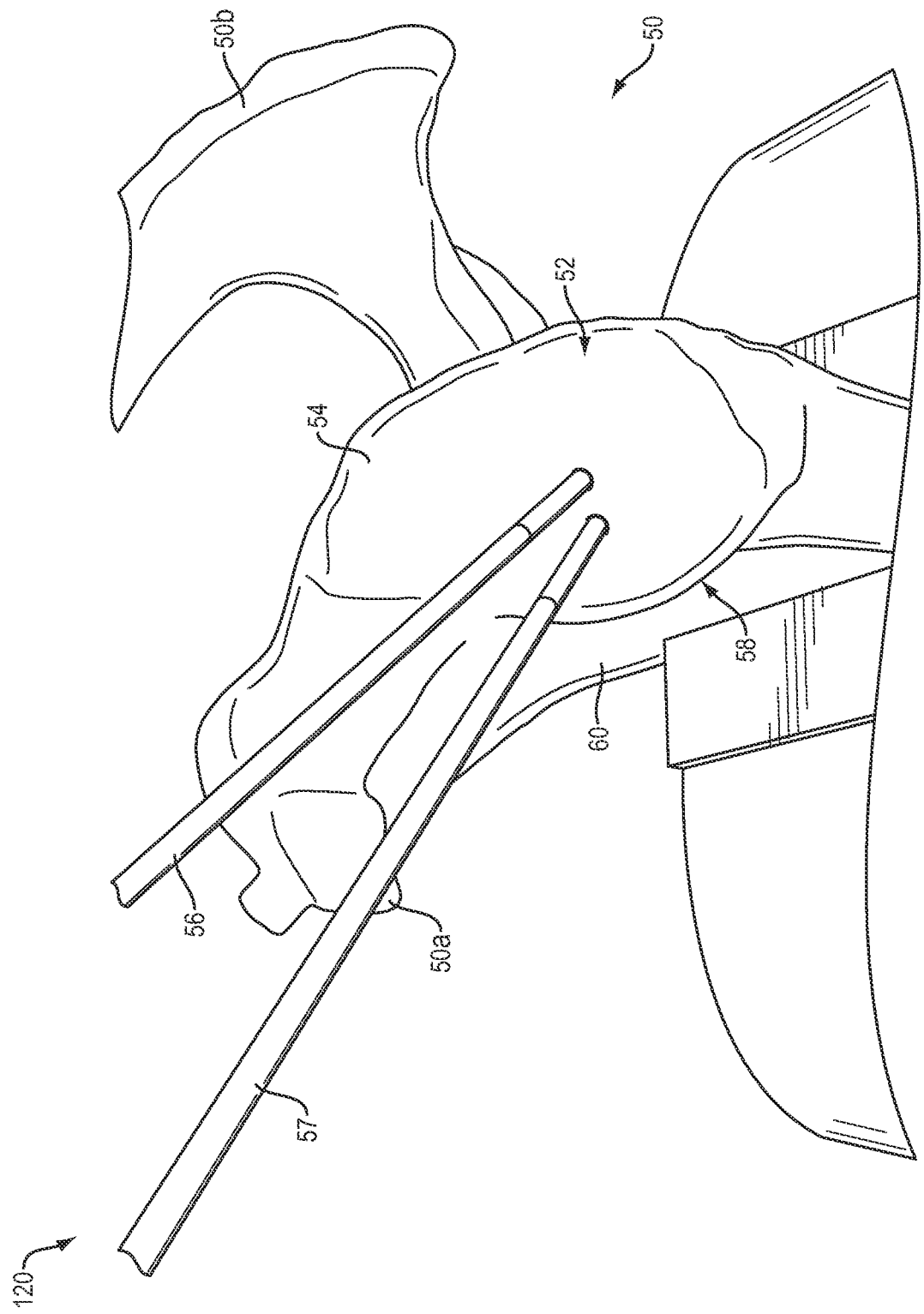
FIG. 31A illustrates a perspective view of two guide pins inserted into a glenoid.
Figure 31B:
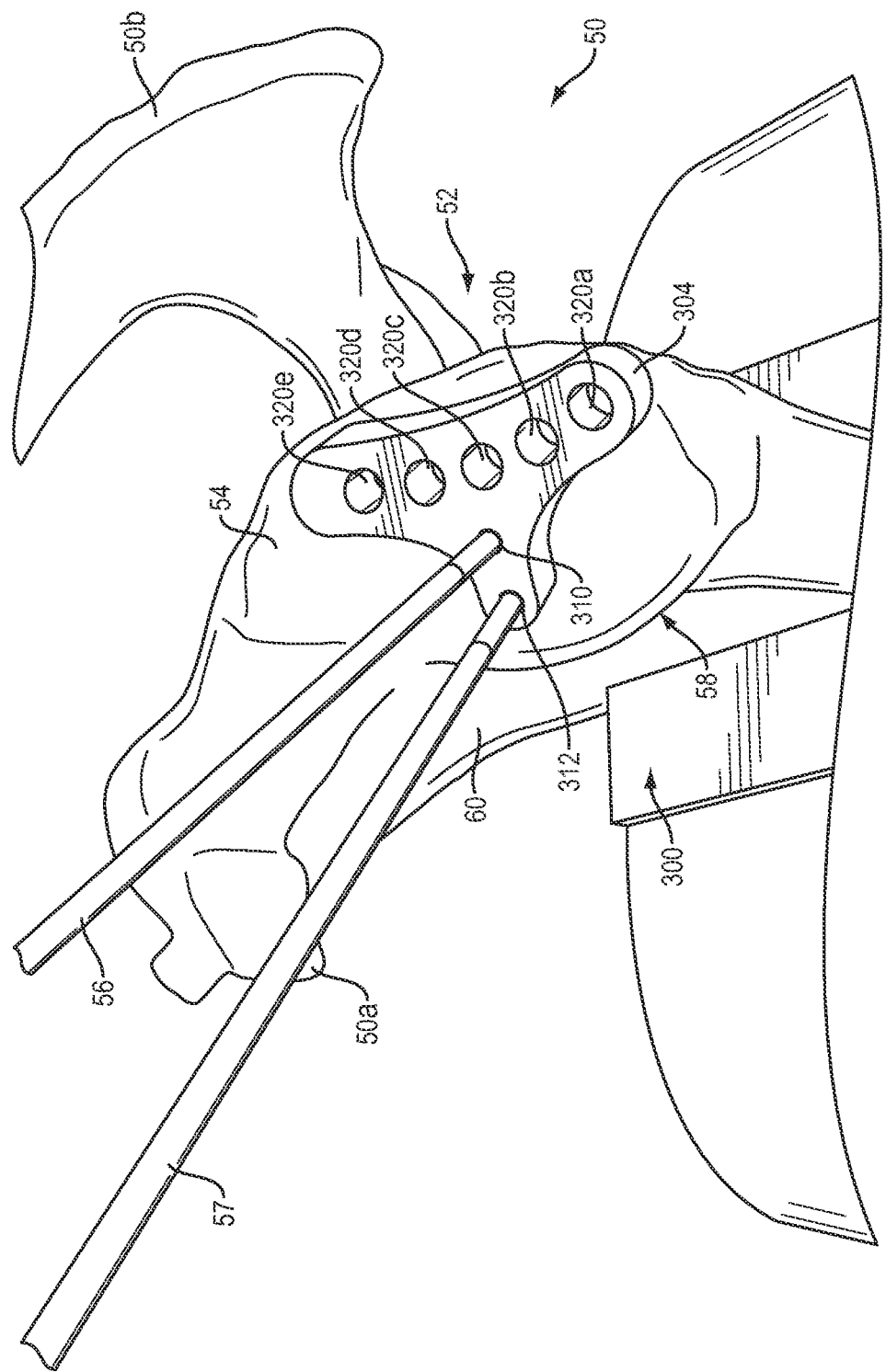
FIG. 31B illustrates a proximal end view of a first guide body of another excision apparatus.
Figure 31C:
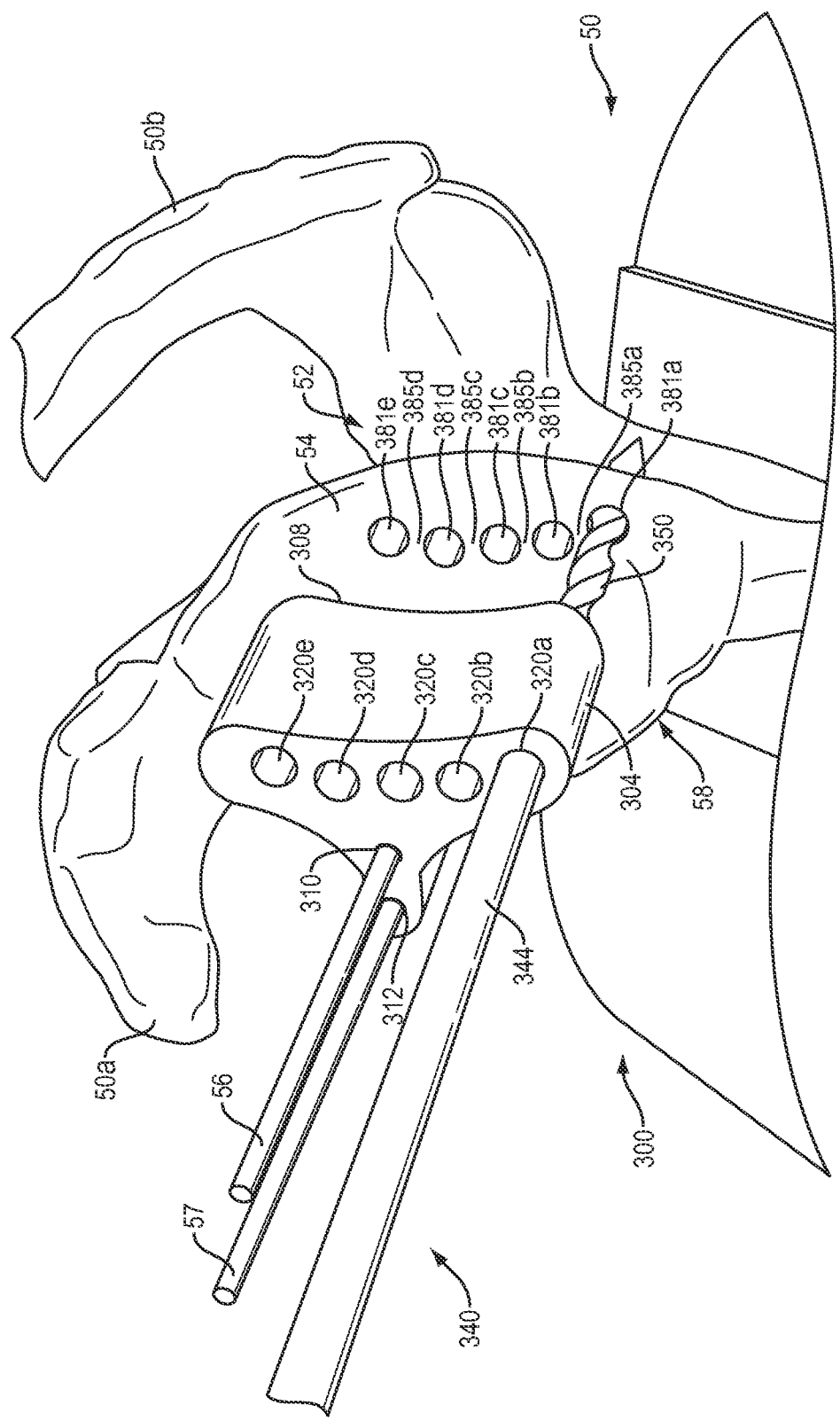
FIG. 31C illustrates a proximal end view of the first guide body of the excision apparatus of FIG. 31B making an excision.
Figure 31D:
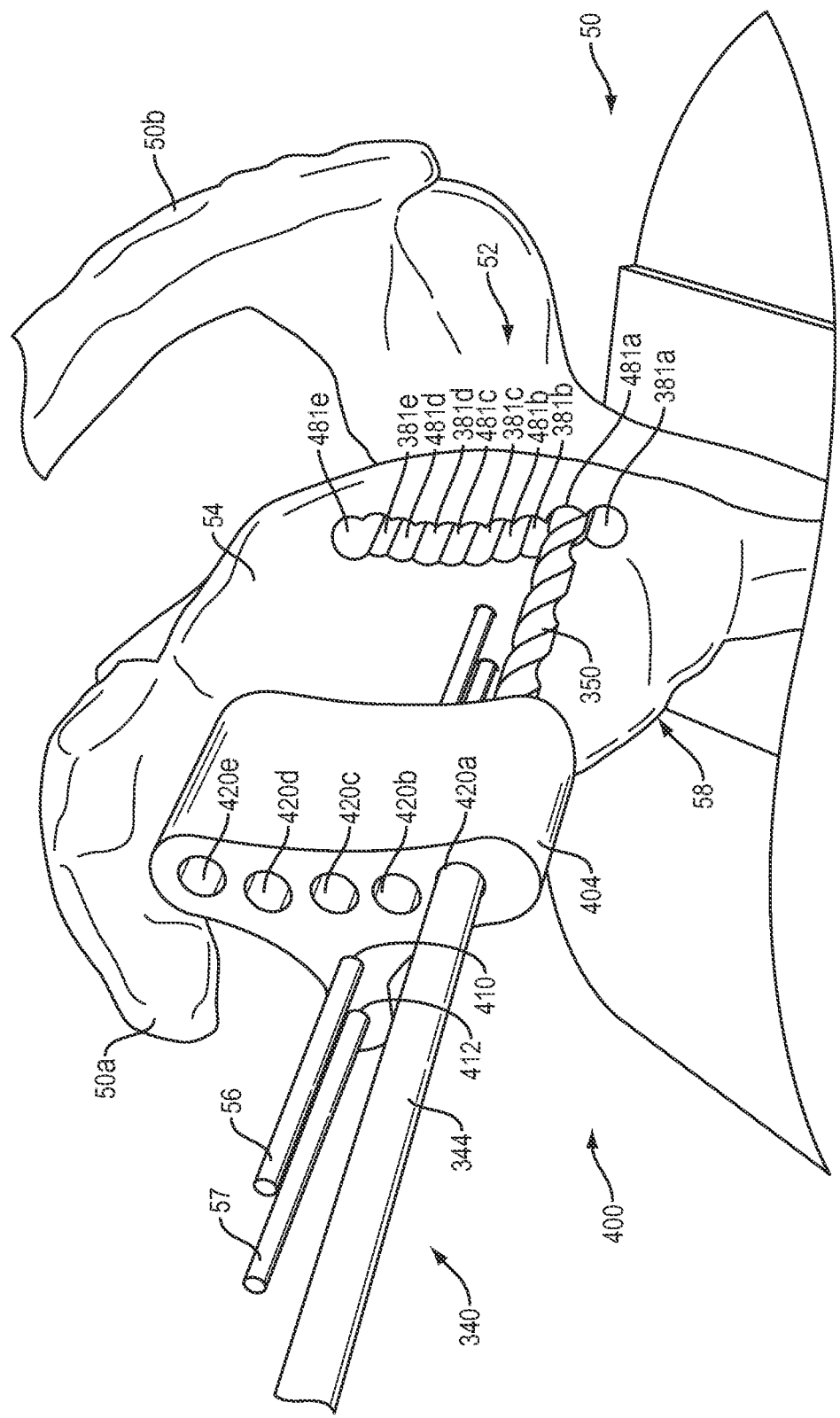
FIG. 31D illustrates a proximal end view of the second guide body of the excision apparatus of FIG. 31B making an excision.
Figure 31E:
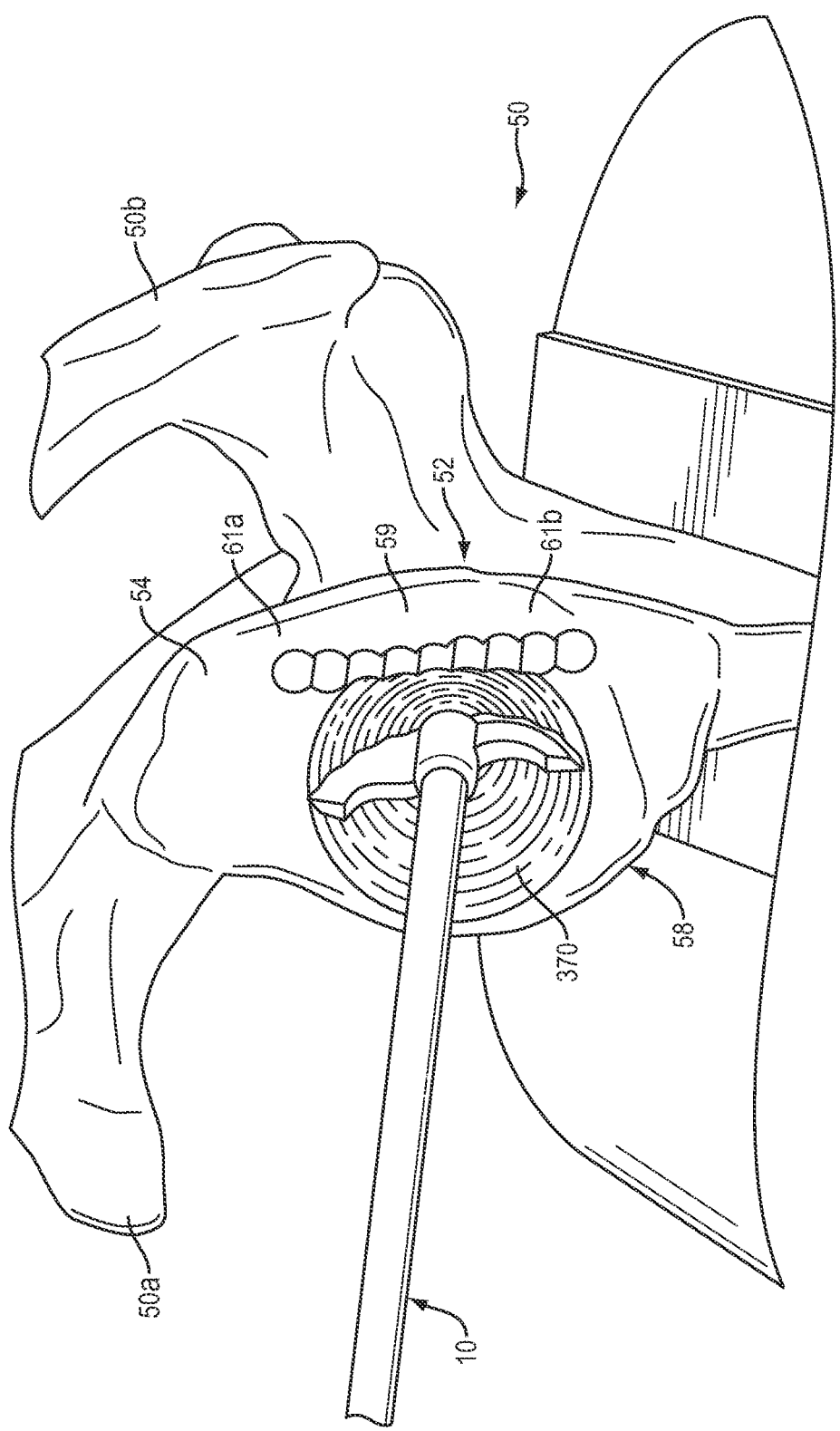
FIG. 31E illustrates a perspective view of an excision device advanced over a guide pin forming another excision site in the glenoid.
Figure 31F:
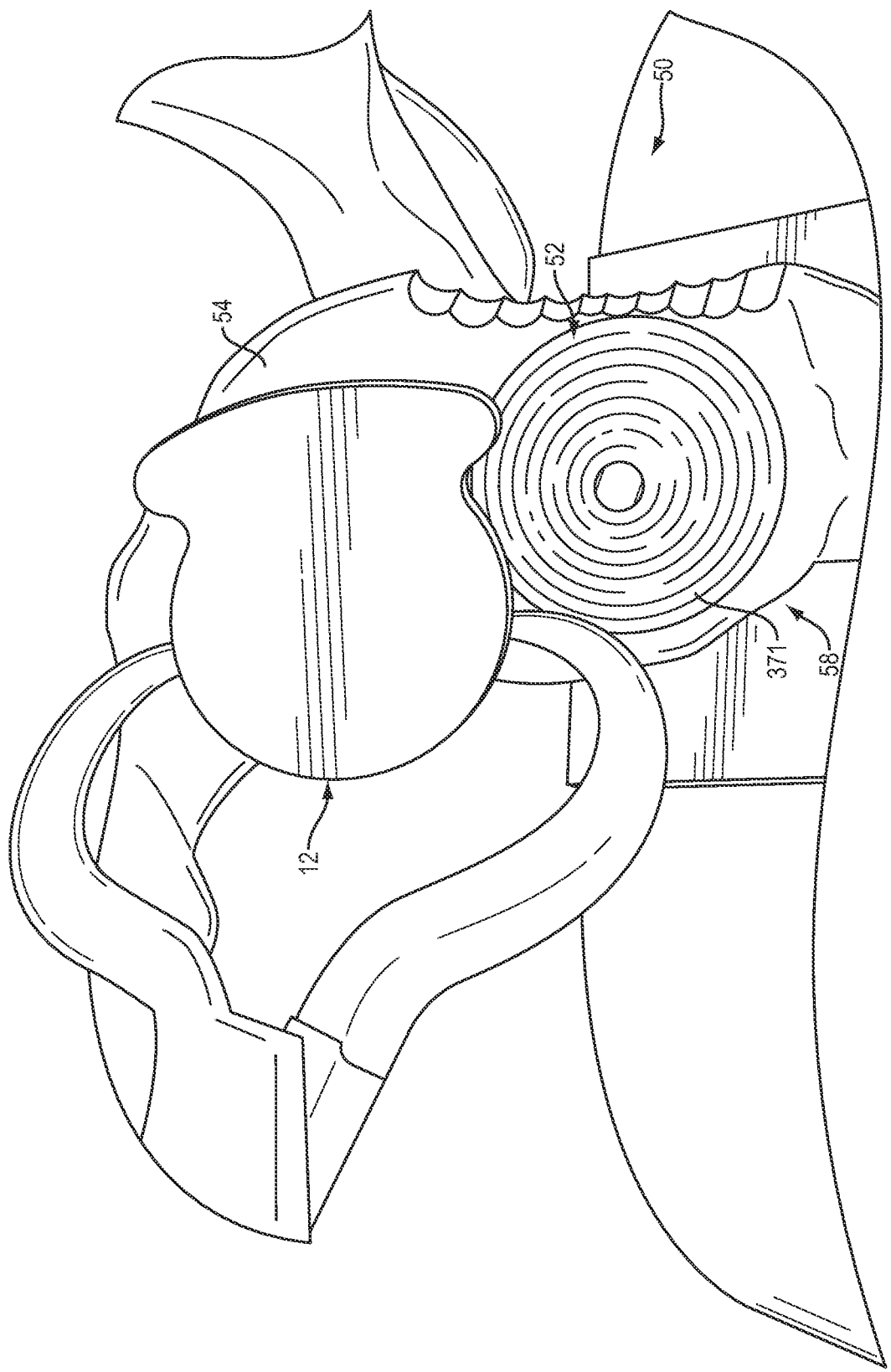
FIG. 31F illustrates an end view of an implant to be implanted in the excision site created in the glenoid in FIGS. 31C-31F.
Figure 31G:
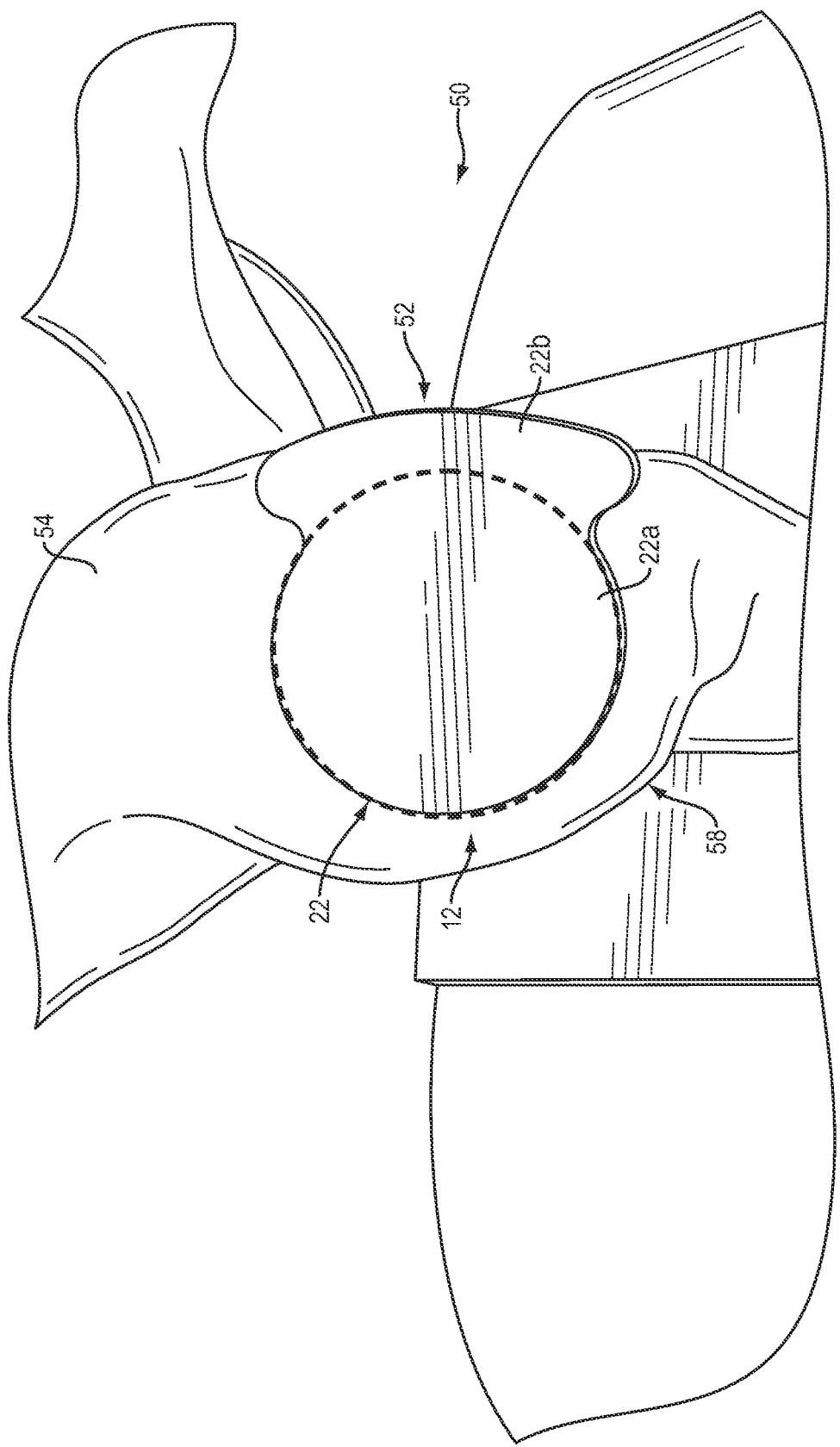
FIG. 31G illustrates an end view of an implant after being implanted in the excision created in a glenoid in FIGS. 31C-31F.
Figure 32:
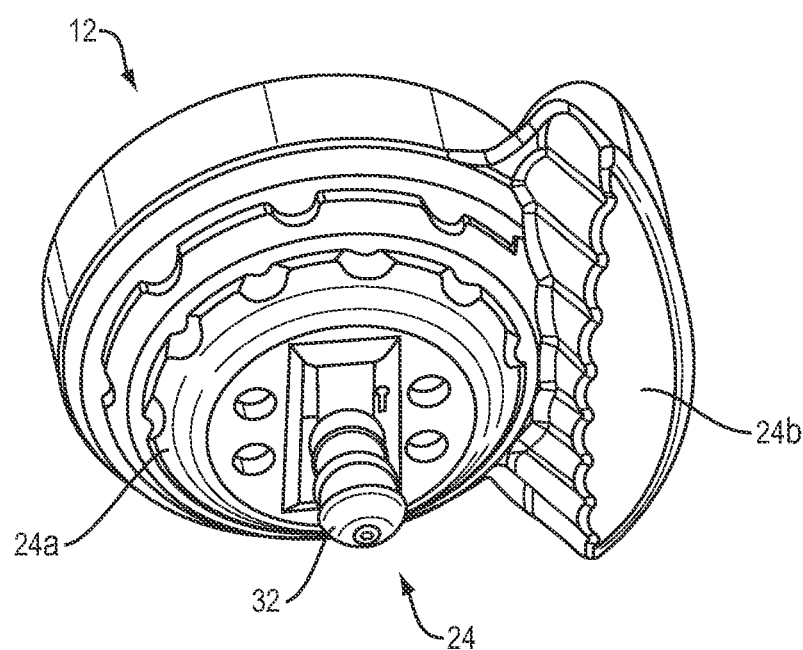
FIG. 32 illustrates a bottom view of the implant of FIGS. 31F and 31G.

Turning to FIGS. 31-32, yet another apparatus, system and/or method for resurfacing at least a portion of an articular surface 54 having a defect by replacing a portion of the articular surface 54 with an implant 12, as well as for locating an implant 12, consistent with the present disclosure, is generally illustrated. Again, the description of the apparatuses, systems, and/or methods herein are not limited to the treatment of any single articular surface of the glenoid 58 and may apply, not only to the one or more articular surfaces that may be present in the glenoid 58, but to other articular surfaces through out the human body as well. Stated another way, the present disclosure describes apparatuses, systems, and/or methods for replacing a portion of the articular surface 54 of the glenoid 58; however, it should be understood that the systems and methods according to the present disclosure may also be used to resurface articular surfaces other than the glenoid 58.

As shown in FIG. 31A, guide pins 56 and 57 are once again shown secured to the glenoid 58, particularly through the articular surface 54. Guide pins 56 and 57 may be secured thereto using any method discussed with the prior embodiments.

As shown in FIG. 31B, excision apparatus 300 may comprise an elongated guide body 304, for example, having a generally T-shaped cross-sectional profile. Guide body 304 comprises a plurality of cylindrical guide pin sleeves 310 and 312 configured to contain guide pins 56 and 57. Guide body 304 also includes a plurality of excision device sleeves 320a-320e to contain an excision device 340. Excision device 340 may comprises a shaft 344 and a cutting head 350 located at a distal end of the shaft 344. As such, it may be understood that excision device sleeve 320 holds shaft 244. As shown, cutting head 350 comprises a spiral groove formed in shaft 344 to provide a drilling tip.

As shown in FIG. 31B, guide body 304 of excision apparatus 300 may be installed on guide pins 56 and 57, particularly by locating guide pin 56 in guide pin sleeve 310 and guide pin 57 in guide pin sleeve 312, and sliding guide body 304 distally down the length of guide pins 56 and 57 until distal end 308 makes contact with the articular surface 54.

Thereafter, as shown in FIG. 31C, shaft 344 of excision device 340 may be extended distally and inserted through excision device sleeve 320a, and cutting head 350 may form a cylindrical planetary excision site 381a in the articular surface 54 of glenoid 58. Thereafter, excision device 340 may be retracted proximally and removed from excision device sleeve 320a, and extended distally and inserted through excision device sleeve 320b, and cutting head 350 may form a cylindrical planetary excision site 381b in the articular surface 54 of glenoid 58. In repetitive fashion, cutting head 350 may then be extended through excision device sleeves 320c to 320e to form a plurality of cylindrical planetary excision sites 381c to 381e, respectively. As shown, the cylindrical planetary excision sites 381c to 381e extend completely through the glenoid and exit through the dorsal surface of the glenoid/scapula, though it may be understood that one or more of the plurality of planetary excision sites do not have to extend all the way through the bone.

As shown in FIG. 31C, cylindrical planetary excision sites 381a to 381e are formed in a substantially linear row with the axis of each cylindrical planetary excision site 381c to 381e extending substantially transverse to the midsagittal plane, and the row extending substantially parallel to the coronal plane. It should be appreciated, however, that the plurality of planetary excision sites do not have to be linearly arranged, and may be arranged in an arcuate and/or nonlinear configuration. Also as shown, a narrow intermediate portion 385a to 385d of the glenoid 58 may be located between adjacent planetary excision sites 381a to 381e after planetary excision sites 381a to 381e are formed. Thereafter, guide body 304 may be slid proximally upward on guide pins 56 and 57 until it is removed from the guide pins 56 and 57.

As shown in FIG. 31D, once guide body 304 is removed, a second elongated guide body 404 may be installed in guide pins 56 and 57. As shown, similar to guide body 304, guide body 404 comprises a plurality of cylindrical guide pin sleeves 410 and 412 configured to contain guide pins 56 and 57. Guide body 404 also includes a plurality of excision device sleeves 320a-320e to contain excision device 340.

As shown, guide body 404 may be installed in guide pins 56 and 57, particularly by locating guide pin 56 in guide pin sleeve 410 and guide pin 57 in guide pin sleeve 412, and sliding guide body 404 distally down the length of guide pins 56 and 57 until distal end 408 makes contact with the articular surface 54.

Thereafter, as shown in FIG. 31D, shaft 344 of excision device 340 may be extended distally and inserted through excision device sleeve 420a, and cutting head 350 may form a partially cylindrical planetary excision site 481a in the articular surface 54 of glenoid 58, and, in doing so, eliminate intermediate portion 385a of the glenoid 58 between planetary excision site 381a and planetary excision site 381b. Thereafter, excision device 340 may be retracted proximally and removed from excision device sleeve 420a, and extended distally and inserted through excision device sleeve 420b, and cutting head 350 may form a partially cylindrical planetary excision site 481b in the articular surface 54 of glenoid 58. In doing so, the planetary excision site 481a 481b eliminates intermediate portion 385b of the glenoid 58 between planetary excision site 381b and planetary excision site 381c. As shown, the planetary excision sites 481a and 481b extend completely through the glenoid and exit through the dorsal surface of the glenoid/scapula as above. Again, as discussed above, one or more of the planetary excision sites 481a-481e may not extend all the way through the bone. In repetitive fashion, cutting head 350 may then be extended through excision device sleeves 320c and 320d to eliminate intermediate portions 385c and 385d, respectively.

In eliminating the intermediate portions 385a to 385d between cylindrical planetary excision sites 381a to 381e, a substantially linear planetary excision site may be formed in glenoid 58 which extends substantially parallel to the coronal plane. As shown, the planetary excision site is adjacent the posterior glenoid rim. In addition, another partially cylindrical excision 481e may be made after excision 381e to increase the overall length of the excision. Again, it should be appreciated that the resulting planetary excision site does not have to be linear, and may be arcuate and/or non-linear depending on the intended application.

While eliminating the intermediate portions 385a to 385d has been described as being performed with a second guide body 404, it may be possible to only use first guide body 304, such as by flipping guide body 304 over such that the proximal end becomes the distal end, and vice-versa.

As a result of the planetary excision sites 381a to 381e and 481a to 481e, which form a substantially linear elongated (slot) planetary excision site, posterior rim segment 59 of the glenoid may be separated from a remainder of the glenoid 58 except for connection to the glenoid 58 by a superior attachment point 61a and an inferior attachment point 61b each having a cross-sectional thickness approximately equal or less than a maximum cross-sectional thickness of the posterior rim segment 59, particularly in the transverse plane.

Thereafter, guide body 404 may be slid proximally upward on guide pins 56 and 57 until it is removed from the guide pins 56 and 57. Furthermore, guide pin 57 may be removed. Thereafter, as shown in FIG. 31E, excision device 10 may be introduced into the surgical site in a manner as set forth in previous embodiments. In order to properly locate excision device 10, guide pin 56 may be passed through cannulated shaft 14, or another guide pin introduced to the glenoid as set forth herein, to form excision site 370. Excision device 10 may be used to form the vault excision site as set forth with the previous embodiments.

As shown in FIG. 31F, thereafter the posterior rim segment 59 may be removed, from the glenoid 58 by cutting the superior attachment point 61a and an inferior attachment point 61b, such as with a pair of snips, particularly in an orientation parallel the transverse plane. After removal of posterior rim segment 59, and forming of the excision site, implant 12 may be inserted into the resulting excision sites as shown in FIG. 31G, and bonded to the glenoid 52, particularly with bone cement as discussed with previous embodiments.

As best shown in FIG. 31F, similar to the previous embodiment, implant 12 may include a load bearing surface 22, which may be divided into two regions 22a and 22b. Also as shown, load bearing surface region 22 may comprise a circular glenoid vault cavity region 22a and a semi-circular glenoid planetary rim region 22b which surrounds approximately 90 degrees of the periphery of the circular cavity region 22a. However it should be understood that the glenoid vault cavity region 22a may be surrounded by a glenoid planetary rim region 22b having other sizes. For example, in certain embodiments, the glenoid planetary rim region 22b may surround from 10 degrees to 120 degrees of the glenoid vault cavity region 22a. In certain other embodiments, the glenoid planetary rim region 22b may surround from 30 degrees to 110 degrees of the glenoid vault cavity region 22a. In other embodiments, the glenoid planetary rim region 22b may surround from 50 degrees to 100 degrees of the glenoid vault cavity region 22a. In still other embodiments, the glenoid planetary rim region 22b may surround from 60 degrees to 90 degrees of the glenoid vault cavity region 22a.

Similar to the prior embodiment, as shown in FIG. 32, the bone facing surface 24 may be configured to be generally received in the excision formed by plurality of planetary excision sites 381a-381e, 481a-481e, vault excision site 370 and the removal of posterior rim segment 59. As shown, the bone facing surface 24 comprises a hemispherical region 24a which is configured to substantially match and correspond to the contour of the hemispherical vault excision site 370, and a flange region 24b which corresponds to the remaining planetary excision sites. Moreover, the implant 12 may optionally include one or more keels or tails 32 extending generally outwardly from the bone facing surface 24 as shown in FIGS. 4 and 5A to 5G. For example, the keel or tail 32 may extend generally outward from the vault region 24d of the bone facing surface 24.

Accordingly, an aspect of the present disclosure relates to a system for repairing a defect on a patient's articular surface. The system may include a guide pin configured to be secured into an articular surface of a glenoid, an excision guide and an excision device.

The excision guide may include a guide head wherein the guide head includes a contact surface configured to locate the excision guide relative to the articular surface. In some embodiments, the guide head may be configured to be positioned generally central on the articular surface. The excision guide may also include a guide sleeve disposed on the guide head. The guide sleeve may be configured to receive the guide pin therethrough and position the guide pin at an angle β relative to an axis generally normal and central to a defect on the articular surface, wherein angle β is less than 90 degrees. In some embodiments, angle β may be in the range of 10 degrees to 90 degrees. In further embodiments, angle β may be in the range of 10 degrees to 30 degrees. The guide sleeve may also be configured to radially offset a point of entry the guide pin into the articular surface from the axis. The excision guide may further include an excision guide arm affixed to the guide head and a handle affixed to the guide arm.

The excision device may include a cannulated shaft and at least one cutter. The cannulated shaft may be configured to be advanced over the guide pin. The at least one cutter may be configured to form a generally hemi-spherical excision site in the articular surface.

A further aspect of the present disclosure relates to a system for repairing a defect on a patient's articular surface. The system may include a guide pin configured to be secured into an articular surface of a glenoid, an impact guide and an impact device.

The impact guide may include an impact guide head having an upper portion and a lower portion. In some embodiments, the impact guide head may have a height Ht that corresponds to a height H of an implant configured to be received in the excision site. In some embodiments, the impact guide head may have a radius Rt that corresponds to a radius Ri of an implant configured to be received in the excision site. In further embodiments, the impact guide head may be releasably coupled to an impact guide arm.

The impact guide head may also have a guide notch defining a first opening through the impact guide head from the upper portion to the lower portion of the impact guide head. The impact guide head may also include a periphery and the first opening may extend to the periphery. The guide notch may be configured to receive the guide pin.

The impact guide may also include an impact slot defining a second opening through the impact guide head from the upper portion of the impact guide head to the lower portion of the impact guide head. The lower portion of the guide head may be configured to be received in an excision site of the articular surface.

The impact device may be configured to be received in and extend through the impact slot. The impact device may include a proximal end and a distal end, wherein the proximal end includes a striking surface and the distal end is configured to be received in and extend through the impact slot. In some embodiments, the impact device may include a chisel. The impact device may be positioned at an angle γ relative to the impact guide arm, wherein angle γ is in the range 0 degrees to 45 degrees. The impact guide may also include an impact guide arm and the impact device may include a proximal end and a distal end, and the proximal end of the impact device may be configured to be disposed generally parallel to the impact guide arm when the distal end is received in the impact slot.

Another aspect of the present disclosure relates to a method for repairing a defect on a patient's articular surface. The method may include positioning on an articular surface an excision guide, wherein the excision guide includes a guide head and a guide sleeve disposed on the guide head, wherein the guide head may include a contact surface configured to locate the excision guide relative to the articular surface. The method may also include advancing a guide pin through the guide sleeve, wherein the guide sleeve is configured to receive the guide pin therethrough and position the guide pin at an angle β relative to an axis generally normal and central to a defect on the articular surface, wherein angle β is less than 90 degrees. The guide pin may then be secured to the articular surface.

The method may also include advancing an excision device over the guide pin, wherein the excision device includes a cannulated shaft and at least one cutter. A generally hemi-spherical excision site may be formed in the articular surface with the cutter. A secondary excision site may also be formed within the generally hemi-spherical excision site in which a portion of the implant may be positioned.

In some embodiments, the method may include advancing an impact guide over the guide pin, wherein the impact guide includes an impact guide head, a guide notch defined in the impact guide head and an impact slot defined in the impact guide head, wherein the guide notch may be configured to receive the guide pin. The impact guide head may then be located in the excision site.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

The invention claimed is:

1. An implant configured to be disposed in a patient's glenoid bone, the implant comprising:
   a load bearing surface including a circular region and a semi-circular rim region at least partially surrounding the circular region along a periphery of the circular region, wherein the load bearing surface is concave having two or more curvatures; and
   a bone facing surface generally configured to correspond to an excision site in the patient's glenoid bone, so as the bone facing surface is configured to dispose entirely within the excision site;
   wherein the bone facing surface comprises a first region generally opposite the circular region having a first shape configured to correspond to a first bone excision site, and a second region generally opposite the semi-circular rim region, the second region configured to extend from the first region and away from the load bearing surface, the second region at least partially surrounding the first region along a periphery of the first region, the second region comprising a plurality of hemispherical segments, each hemispherical segment configured to correspond to a second portion of the excision site.

2. The implant of claim 1, wherein the semi-circular rim region partially surrounds the circular region from about 10 degrees to about 270 around the periphery of the circular region.

3. The implant of claim 1, wherein the second region partially surrounds the first region from about 10 degrees to about 270 around the periphery of the first region.

4. The implant of claim 1, wherein the first region has a generally hemispherical shape and substantially configured to correspond to a first portion of the excision site.

5. The implant of claim 4, wherein the first region includes at least one of a protrusion, a lip or a rib configured to engage bone of the first portion of the excision site.

6. The implant of claim 4, wherein the first region includes at least one of a threaded base, a keel, or a tail configured to engage bone of the first portion of the excision site.

7. A system for repairing a defect on at least a portion of an articular surface of a glenoid bone, said system comprising:
   at least two guide pins, said at least two guide pins comprising a first guide pin and a second guide pin, said first guide pin and said second guide pin configured to be secured to said glenoid;

an excision apparatus to form an excision site on at least a portion of an articular surface of the glenoid bone, the excision apparatus comprising a guide body and an excision device; said guide body comprising a plurality of guide pin sleeves to contain said at least two guide pins, said plurality of guide pin sleeves comprising at least a first guide pin sleeve and a second guide pin sleeve; wherein, when said first guide pin is contained in said first guide pin sleeve and said second guide pin is contained in said second guide pin sleeve, said guide body is retained in a first excision position for said excision device and; said guide body further comprises a third guide pin sleeve; and wherein, when said first guide pin is contained in said first guide pin sleeve and said second guide pin is contained in said third guide pin sleeve, said guide body is retained in a second excision position for said excision device; said guide body is rotatable on at least one of said first guide pin and said second guide pin from said first excision position to said second excision position; and an implant comprising a load bearing surface including a circular region and a semi-circular rim region at least partially surrounding the circular region along a periphery of the circular region, wherein the load bearing surface is concave having two or more curvatures; the implant also comprising a bone facing surface generally corresponding to the excision site, so as to dispose the bone facing surface entirely within the excision site; the bone facing surface having a first region generally opposite the circular region having a first shape corresponding to a first bone excision site, and a second region generally opposite the semi-circular rim region, the second region also extending from the first region and away from the load bearing surface, the second region also at least partially surrounding the first region along a periphery of the first region, the second region also comprising a plurality of hemispherical segments, each hemispherical segment configured to correspond to a second portion of the excision site.

8. The system of claim 7, wherein said guide body is slidable along said first guide pin and said second guide pin when said first guide pin is contained in said first guide pin sleeve and said second guide pin is contained in said second guide pin sleeve.

9. The system of claim 7, wherein said first guide pin sleeve and said second guide pin sleeve are substantially parallel.

10. The system of claim 9, wherein said first guide pin sleeve has a diameter substantially equal to a diameter of said first guide pin and said second guide pin sleeve has a diameter substantially equal to a diameter of said second guide such that, when said first guide pin is contained in said first guide pin sleeve and said second guide pin is contained in said second guide pin sleeve, said first guide pin and said second guide pin are substantially parallel.

11. The system of claim 9, wherein said excision device has an axis of rotation which is substantially parallel to said first guide pin sleeve and said second guide pin sleeve.

12. The system of claim 7, wherein said first guide pin sleeve and said third guide pin sleeve are substantially parallel.

13. The system of claim 12, wherein said first guide pin sleeve has a diameter substantially equal to a diameter of said first guide pin and said third guide pin sleeve has a diameter substantially equal to a diameter of said second guide such that, when said first guide pin is contained in said first guide pin sleeve and said second guide pin is contained in said third guide pin sleeve, said first guide pin and said second guide pin are substantially parallel.

14. The system of claim 12, wherein said excision device has an axis of rotation which is substantially parallel to said first guide pin sleeve and said third guide pin sleeve.

15. The system of claim 7, wherein said guide body further comprises a fourth guide pin sleeve; and wherein, when said first guide pin is contained in said first guide pin sleeve and said second guide pin is contained in said fourth guide pin sleeve, said guide body is retained in a third excision position for said excision device.

16. The system of claim 15, wherein said first guide pin sleeve and said fourth guide pin sleeve are substantially parallel.

17. The system of claim 16, wherein said first guide pin sleeve has a diameter substantially equal to a diameter of said first guide pin and said fourth guide pin sleeve has a diameter substantially equal to a diameter of said second guide such that, when said first guide pin is contained in said first guide pin sleeve and said second guide pin is contained in said fourth guide pin sleeve, said first guide pin and said second guide pin are substantially parallel.

18. The system of claim 17, wherein said excision device has an axis of rotation which is substantially parallel to said first guide pin sleeve and said fourth guide pin sleeve.

19. The system of claim 15, wherein said guide body is rotatable on at least one of said first guide pin and said second guide pin from said second excision position to said third excision position.

20. The system of claim 7, wherein said excision device comprises a rotating cutter.

21. The system of claim 7, wherein said excision device is a reamer.

22. The system of claim 7, wherein the semi-circular region partially surrounds the circular region from about 10 degrees to about 270 around the periphery of the circular region.

23. The system of claim 7, wherein the wherein the second region partially surrounds the first region from about 10 degrees to about 270 around the periphery of the first region.

24. The system of claim 7, wherein the first region has a generally hemispherical shape and substantially corresponding to a first portion of the excision site.

25. The system of claim 7, wherein the first region includes at least one of a protrusion, a lip or a rib to engage bone of the first portion of the excision site.

26. The system of claim 7, wherein the first region includes at least one of a threaded base, a keel, or a tail to engage bone of the first portion of the excision site.

* * * * *